(12) United States Patent
Kirkpatrick et al.

(10) Patent No.: US 12,178,634 B2
(45) Date of Patent: Dec. 31, 2024

(54) ELECTRONIC STETHOSCOPE AND DIAGNOSTIC ALGORITHM

(71) Applicant: Korion Health Inc., Pittsburgh, PA (US)

(72) Inventors: Galen Charles Pershing Kirkpatrick, Carrboro, NC (US); Anna Li, Pittsburgh, PA (US); Thomas Hastings Greer, IV, Durham, NC (US); Akshaya Poorani Anand, Ellicott City, MD (US); Nicholas Chen, Chicago, IL (US); Eunice Chee-Kay Chan, San Ramon, CA (US)

(73) Assignee: Korion Health Inc., Pittsburgh, PA (US)

( * ) Notice: Subject to any disclaimer, the term of this patent is extended or adjusted under 35 U.S.C. 154(b) by 0 days.

(21) Appl. No.: 18/632,981

(22) Filed: Apr. 11, 2024

(65) Prior Publication Data

US 2024/0252139 A1    Aug. 1, 2024

Related U.S. Application Data

(63) Continuation of application No. PCT/US2023/018741, filed on Apr. 14, 2023.
(Continued)

(51) Int. Cl.
*A61B 7/04* (2006.01)
*A61B 5/00* (2006.01)
(Continued)

(52) U.S. Cl.
CPC .............. *A61B 7/04* (2013.01); *A61B 90/08* (2016.02); *G16H 50/20* (2018.01); *A61B 2090/0807* (2016.02); *A61B 2562/0204* (2013.01)

(58) Field of Classification Search
None
See application file for complete search history.

(56) References Cited

U.S. PATENT DOCUMENTS

| 5,852,263 | A  | 12/1998 | Dieken |
| 8,583,207 | B2 | 11/2013 | Tsai et al. |

(Continued)

FOREIGN PATENT DOCUMENTS

| WO | WO-2013184437 A2 * | 12/2013 | .............. A61B 5/002 |
| WO | WO-2021/229600 A1 | 11/2021 | |

(Continued)

OTHER PUBLICATIONS

Kong et al, "PANNs: Large-Scale Pretrained Audio Neural Networks for Audio Pattern Recognition". pp. 1-15. 2020. (Year: 2020).*

(Continued)

*Primary Examiner* — Qin Zhu
(74) *Attorney, Agent, or Firm* — Choate, Hall & Stewart LLP; Peter A. Flynn; Sahar Elahi

(57) ABSTRACT

Sounds produced by internal organs of the body can be used to monitor health conditions related to, for example, the heart and lungs. The present disclosure includes an electronic stethoscope that may be positioned by a user on locations of the body to record sounds from organs. The present disclosure also includes visual algorithms to guide positioning of the electronic stethoscope and audio diagnostic algorithms for providing analysis of recorded sounds.

21 Claims, 45 Drawing Sheets

Related U.S. Application Data

(60) Provisional application No. 63/358,086, filed on Jul. 1, 2022, provisional application No. 63/331,861, filed on Apr. 17, 2022.

(51) Int. Cl.
*A61B 7/00* (2006.01)
*A61B 90/00* (2016.01)
*G16H 40/67* (2018.01)
*G16H 50/20* (2018.01)
*G16H 50/70* (2018.01)
*H04R 1/46* (2006.01)

(56) References Cited

U.S. PATENT DOCUMENTS

| | | | |
|---|---|---|---|
| 9,973,847 B2 | 5/2018 | Wong | |
| D930,163 S | 9/2021 | Turkieltaub et al. | |
| 11,484,283 B2 | 11/2022 | Shekhar et al. | |
| 2015/0164340 A1* | 6/2015 | Bedingham | A61B 5/282 600/513 |
| 2016/0100817 A1 | 4/2016 | Hussain | |
| 2016/0287207 A1* | 10/2016 | Xue | A61B 5/743 |
| 2018/0303343 A1* | 10/2018 | Dubin | A61B 8/14 |
| 2019/0221310 A1* | 7/2019 | Bates | G16H 20/00 |
| 2019/0279768 A1 | 9/2019 | Bates et al. | |
| 2020/0337794 A1 | 10/2020 | Hall et al. | |
| 2020/0388287 A1* | 12/2020 | Anushiravani | G16H 20/10 |
| 2021/0145306 A1 | 5/2021 | Karankevich et al. | |
| 2021/0236056 A1 | 8/2021 | Dubin et al. | |
| 2021/0282739 A1 | 9/2021 | Eshel et al. | |
| 2021/0330189 A1 | 10/2021 | Rose et al. | |
| 2021/0345934 A1 | 11/2021 | Landgraf et al. | |
| 2021/0345985 A1 | 11/2021 | Cunningham | |
| 2022/0293273 A1 | 9/2022 | Bates et al. | |
| 2022/0335696 A1* | 10/2022 | Shelton, IV | H04W 12/50 |
| 2022/0354451 A1 | 11/2022 | Venkatraman et al. | |
| 2023/0096006 A1* | 3/2023 | Blair | G08B 21/0211 600/586 |
| 2023/0270389 A1* | 8/2023 | Randall | H04R 1/46 600/586 |
| 2023/0270402 A1 | 8/2023 | Lou et al. | |
| 2023/0293137 A1 | 9/2023 | Dockendorf et al. | |
| 2023/0371843 A1 | 11/2023 | McLane | |
| 2024/0000381 A1 | 1/2024 | Andino et al. | |
| 2024/0032887 A1 | 2/2024 | Zaboronok et al. | |

FOREIGN PATENT DOCUMENTS

| | | |
|---|---|---|
| WO | WO-2023/134253 A1 | 7/2023 |
| WO | WO-2023/205059 A1 | 10/2023 |

OTHER PUBLICATIONS

International Search Report for PCT/US23/18741, filed Apr. 14, 2023, 6 pages, (mailed Sep. 7, 2023).
Invitation to Pay Additional Fees for PCT/US23/18741, filed Apr. 14, 2023, 4 pages, (mailed Jun. 9, 2023).
Jani, V. et al., The discerning ear: cardiac auscultation in the era of artificial intelligence and telemedicine, Eur. Heart J. Digit. Health, 2(3):456-466 (2021).
Written Opinion for PCT/US23/18741, filed Apr. 14, 2023, 9 pages, (mailed Sep. 7, 2023).

* cited by examiner

| Heart listening location | Vertical position | Horizontal position |
|---|---|---|
| A (aortic valve area) | 15-31% of RS→RH distance | 20-36% of RS→LS distance |
| P (pulmonic valve area) | 15-31% of LS→LH distance | 20-36% of LS→RS distance |
| T (tricuspid valve area) | 33-49% of LS→LH distance | 17-33% of LS→RS distance |
| M (mitral valve area) | 37-35% of LS→LH distance | 2-18% of LS→RS distance |

ELECTRONIC STETHOSCOPE AND DIAGNOSTIC ALGORITHM

CROSS-REFERENCE TO RELATED APPLICATIONS

This application is a continuation of International Application No. PCT/US23/18741, filed Apr. 14, 2023, entitled "Electronic Stethoscope and Diagnostic Algorithm," which claims priority to U.S. Provisional Patent Application No. 63/331,861, filed Apr. 17, 2022, entitled "Electronic Stethoscope with Analysis," and U.S. Provisional Patent Application No. 63/358,086, filed Jul. 1, 2022, entitled "Electronic Stethoscope and Diagnostic Algorithm," the contents of each of which are incorporated herein by reference in their entireties.

FIELD

The present disclosure relates generally to electronic stethoscopes and computer-aided auscultation, and in particular to electronic stethoscopes combined with visual and audio algorithms.

BACKGROUND

Cardiovascular diseases (CVDs) are the leading cause of death worldwide, responsible for approximately 17.9 million deaths annually, which represents approximately one in every three deaths (World Health Organization, https://www.who.int/news-room/fact-sheets/detail/cardiovascular-diseases-(cvds)). CVDs include several disorders that affect the heart or the blood vessels. Around the world, there are significant disparities in risks and outcomes for CVDs, with people at lower income levels disproportionately affected. Heart disease can be mitigated by changes in diet, environment, and physical activity, and by regular monitoring and screening, but there are many barriers to accessing regular heart monitoring due to cost, logistics, and lack of medical providers especially for populations at lower socio-economic levels.

A heart murmur is a sound produced by blood flow in the heart that deviates from normal flow patterns, and can be used to diagnose various heart conditions. Several heart conditions involve the improper flow of blood through heart valves such that turbulent blood flow occurs, resulting in audible sounds that can be heard using a stethoscope. Heart murmurs may also occur due to various physiological conditions outside the heart and are not associated with heart diseases. Distinguishing between benign murmurs and murmurs resulting from heart valve defects and other heart conditions can be done by auscultation, or listening to heart sounds using a stethoscope, but usually requires a skilled practitioner; diagnosis of heart conditions by auscultation by general practitioners may be less accurate than by specialists.

Respiratory diseases are another leading cause of death worldwide, responsible for over 3 million deaths annually (World Health Organization, https://www.who.int/news-room/fact-sheets/detail/chronic-obstructive-pulmonary-disease-(copd)). These conditions impact the function of airways and lungs, and can be caused by smoking, air pollution, environmental contamination, and infections by bacteria and viruses. Similar disparities exist for respiratory diseases as for cardiovascular diseases, with people at lower income levels disproportionately affected. Regular access to medical care, including auscultation with a stethoscope by a qualified clinician, are important for diagnosing respiratory diseases, providing treatments to improve breathing, and prevent deaths.

Auscultation is the act of listening to sounds from internal organs, usually using a stethoscope, in order to non-invasively examine and diagnose a patient. It is generally an inexpensive and widely used method, but the level of accuracy of diagnosis of particular conditions or diseases depends greatly on the skill level, experience, and expertise of the individual performing the auscultation. This can be particularly challenging in communities where many people lack regular access to medical practitioners or are unable to reach medical care due to barriers related to cost, transportation, and time. Even for patients who can receive medical care from practitioners, doctor visits may be infrequent and regular monitoring may not be possible.

There have been multiple efforts to develop electronic stethoscopes and electronic devices and software programs, with the goals of enhancing the ability to hear the sounds and to improve the diagnoses using computer algorithms (Jani et al., *Eur. Heart J. Digital Health*, 2021, 2 (3), 456-466, https://doi.org/10.1093/ehjdh/ztab059). However, many of these products are expensive because the stethoscopes contain complex processing hardware, or the accompanying software requires costly ongoing subscriptions. Other products are targeted toward medical practitioners rather than the broader community of users at home or in local non-medical establishments such as pharmacies or stores, and thus will not help increase access to auscultation-based screening. Furthermore, these products do not have a way to reliably help the user or patient position the stethoscope on their body in the correct locations to listen for heart and lung sounds without the participation of a medical practitioner.

SUMMARY

The present disclosure provides an electronic stethoscope and associated software algorithms for recording and analyzing heart and lung sounds to provide diagnoses of heart and lung conditions. In some embodiments, the present disclosure provides an electronic stethoscope that comprises a light-emitting device that can be viewed and analyzed by computer vision algorithms to guide a user to position the stethoscope on the front and back of the user's chest at target locations in real time. In some embodiments, the electronic stethoscope further provides a microphone to record sounds from the front and back of the user's chest and back at the target locations. In some embodiments, the electronic stethoscope provides a membrane covering a concave face of a cylindrical bell that is pressed to the skin on the front or back chest to transmit sounds from the interior of the chest to the microphone. In some embodiments, the electronic stethoscope provides a processor to convert sounds received by the microphone into a digital signal.

In some embodiments, the present disclosure provides technologies for visually assessing a user's pose and positions of an electronic stethoscope on the user's pose in real time, and further directs the user to move the stethoscope toward a plurality of medically relevant target locations on the front and back of the user's chest. In some embodiments, the electronic stethoscope may record sounds at the plurality of medically relevant target locations. In some embodiments, the present disclosure provides technologies for processing and analyzing the recorded sounds. In some embodiments, the present disclosure provides technologies for using computer-based machine learning algorithms and methods to classify heart sounds according to various known heart conditions, and to classify lung sounds according to various known lung conditions. The present disclosure, in some embodiments, further provides technologies for computer-based machine learning algorithms and methods to process and analyze recordings of unknown sounds recorded by the electronic stethoscope and diagnose possible heart conditions and/or lung conditions.

In some embodiments, the present disclosure provides technologies for analyzing a plurality of anonymized sound recordings from users' hearts and/or lungs and diagnoses of heart and/or lung conditions. In some embodiments, the present disclosure provides technologies for storing, transmitting, and/or processing recordings of sounds, information related to users' health conditions, and diagnoses of heart and/or lung conditions.

The present disclosure further provides embodiments of an electronic stethoscope and components associated with the electronic stethoscope, embodiments of methods of using an electronic stethoscope, embodiments of software algorithms that may process and classify sounds and provide diagnoses of heart and/or lung conditions, embodiments of software algorithms that may process live video data to locate positions corresponding to a user's pose and to the location of an electronic stethoscope, embodiments of software algorithms that enable interaction with one or more users, embodiments of processing, storing, and transmitting data obtained from the diagnosis algorithms, and embodiments of the usage of the system in various configurations.

Advantages of the methods, devices, and systems described in the present disclosure include, for example, improved access to monitoring of heart and lung conditions, lower cost and ease of use compared to typical electronic stethoscopes, accurate positioning of the stethoscope using visual algorithms to capture sounds from medically relevant target locations, automated diagnosis of common heart and lung conditions, and connection to physicians, telemedicine providers, and electronic medical records.

In one aspect, the present embodiments are directed to an electronic stethoscope including: a chest piece, including: a bell portion including a hollow cylinder, concave face, and a flat face; and a circular membrane that is attached to the concave face of the cylindrical bell portion; a stem portion comprising a hollow cylinder attached at an outer surface of the bell portion, wherein a longitudinal axis of the stem portion is oriented perpendicular to the center axis of the bell portion; a microphone compartment disposed within a lumen of the stem portion; a microphone disposed within the microphone compartment; a microphone seal disposed circumferentially around the microphone and disposed within the microphone compartment to form a seal between the microphone and the microphone compartment; a light-emitting device disposed on the flat face of the bell portion; an analog-to-digital converter disposed within a lumen of the stem portion; a microcontroller disposed within a lumen of the stem portion; electrical wiring connecting the microphone, the analog-to-digital converter, and the microcontroller; and an electrical data connection from the microcontroller.

In some embodiments, the membrane encloses a volume of air at the concave end of the bell portion. In some embodiments, the membrane includes a sheet of plastic about 0.025 inches in thickness. In some embodiments, the membrane includes a polymer selected from the group consisting of acetate, polyester, polyethylene terephthalate (PET), polyethylene, polypropylene, polystyrene, epoxy fiberglass, resin, thermoset plastic, polyvinyl chloride (PVC), and polytetrafluoroethylene (PTFE). In some embodiments, the membrane is attached to the bell portion by an adhesive selected from the group consisting of glue, latex, cyanoacrylate, epoxy resin, a hot-melt glue, rubber cement, polyvinyl acetate, polyvinyl alcohol (PVA), polyvinyl chloride (PVC), and polyvinyl chloride emulsion.

In some embodiments, a circumference of the membrane is surrounded by a flexible ring to form a rim. In some embodiments, the flexible ring includes a polymer selected from the group consisting of silicone rubber and polyvinyl chloride (PVC). In some embodiments, the membrane is attached to the bell portion by mechanical clamping.

In some embodiments, the bell portion includes an internal bore that extends between the concave face of the bell portion and the microphone compartment, wherein the diameter of the internal bore is about 0.25 inches. In some embodiments, the stem portion includes a shoulder region that has a diameter that changes along the length of the stem portion to accommodate a microphone housed within the microphone compartment. In some embodiments, the bell portion and the stem portion include a plastic material selected from the group consisting of polylactic acid (PLA), acrylonitrile butadiene styrene (ABS), or polyethylene terephthalate glycol-modified (PET-G).

In some embodiments, the bell portion and the stem portion are formed using at least one of additive manufacturing, molding, casting, and extrusion. In some embodiments, the bell portion has a diameter of approximately 1.625 inches and a height of approximately 1.75 inches. In some embodiments, the concave face has an inverted conical profile with a diameter of approximately 1.25 inches and a depth of approximately 0.0625 inches.

In some embodiments, the electrical connection includes at least one of a wired connection and a wireless connection. In some embodiments, the wired connection includes at least one of a serial bus connection, a universal serial bus (USB) connection, a parallel bus connection, an audio connection, an Ethernet connection, and an optical fiber connection. In some embodiments, the wireless connection includes at least one of a close-range wireless connection, a Bluetooth connection, a Wi-Fi connection, and a cellular connection.

In some embodiments, the light-emitting device includes a light-emitting diode, an incandescent light, a fluorescent light, a halogen light, or a gas-discharge lamp. In some embodiments, the light-emitting device alternates between on and off states at a controllable repetition frequency between about 2 Hz and 30 Hz. In some embodiments, the light-emitting device alternates between on and off states in a controllable pattern. In some embodiments, the light-emitting device includes at least two light-emitting components each emitting light at a specified wavelength and each alternating between on and off states in a controllable pattern. In some embodiments, the light-emitting device emits light at a wavelength between 400 nm and 1000 nm.

In some embodiments, the electrical wiring connects the microphone to the analog-to-digital converter and connects the analog-to-digital converter to the microcontroller.

In some embodiments, the chest piece is attached to at least one of a rigid rod and a flexible strap, wherein the rigid rod may be manually held by a user to position the stethoscope against a user's back, and wherein the flexible strap may be used to attach the stethoscope around a user's torso to position the stethoscope against a user's front or back.

In some embodiments, the rigid rod includes an elongate rod and a handle. In some embodiments, the rigid rod includes at least one of a metal, a plastic, or a wood. In some embodiments, the flexible strap includes one or more lengths of strap and one or more clasp mechanisms. In some embodiments, the one or more lengths of strap include at least one of woven fabric, knitted fabric, leather, metal chain mail, elastic fabric, nylon, cotton, webbing, polyurethane, polyvinyl chloride, polyethylene, polypropylene, wool, linen, cork, rubber, neoprene, spandex, elastane, rayon, carbon fiber, a composite material, silicon, rope, hemp, bamboo, cellulose, or paper.

In some embodiments, the microphone includes at least one of a condenser microphone, a dynamic microphone, a ribbon microphone, a carbon microphone, a piezoelectric microphone, and a microelectromechanical systems (MEMS) microphone. In some embodiments, the microphone seal includes a material disposed circumferentially around and disposed in contact with an interior wall of a lumen of the microphone compartment, and further disposed in contact with an exterior surface of the microphone such that air does not pass between the interior wall of the lumen of the microphone compartment and the exterior surface of the microphone.

In some embodiments, the microphone seal includes at least one of silicone, rubber, adhesive, resin, epoxy, polymer, wax, acrylic, or rubber cement, thermoplastic adhesive, hot-melt adhesive, polytetrafluoroethylene, polyurethane, polycarbonate, polypropylene, nylon, nitrile, neoprene, polyvinyl chloride, fluorocarbon, and fluorosilicone.

In another aspect, the present embodiments are directed to an electronic stethoscope including: a chest piece including a cylindrical bell portion, a hollow stem portion, a bore disposed within the cylindrical bell portion and connecting to the interior lumen of the hollow stem portion, and a circular membrane covering one end of the cylindrical bell portion; a microphone disposed within the stem portion; a light-emitting device disposed on the exterior of the bell portion; and an electronic data connection between the microphone and an electronic device.

In some embodiments, the electronic stethoscope further includes a plurality of electrical wiring, a microcontroller, and an analog-to-digital converter. In some embodiments, the electrical data connection comprises at least one of a wired connection and a wired connection.

In another aspect, the present embodiments are directed to a method of training a machine learning algorithm to identify heart sounds including: obtaining heart sound recordings corresponding to known heart conditions and corresponding to normal healthy heart function; obtaining non-heart sound recordings; providing the heart sound recordings and non-heart sound recordings to an audio classifier model; and using the audio classifier model to train the machine learning algorithm to distinguish between the heart sound recordings and non-heart sound recordings, wherein the heart sound recordings are obtained from recordings performed by the electronic stethoscope of claim 1, by alternative electronic stethoscopes, by alternative microphones, and by smartphone microphones, wherein non-heart sound recordings may include sounds such as speech, vehicle traffic, dogs barking, children crying, noise, and music, wherein the audio classifier model comprises a pre-trained audio neural network (PANN), a dataset of known audio recordings, and information regarding health conditions and demographics of patients with known heart conditions, and wherein providing sound recordings to the audio classifier model occurs on a regular repeating schedule and comprises providing new sound recordings and new known health information.

In another aspect, the present embodiments are directed to a method of training a machine learning algorithm to identify lung sounds including: obtaining heart sound recordings corresponding to known lung conditions and corresponding to normal healthy lung function; obtaining non-lung sound recordings; providing the lung sound recordings and non-lung sound recordings to an audio classifier model; and using the audio classifier model to train the machine learning algorithm to distinguish between the lung sound recordings and non-lung sound recordings, wherein the heart sound recordings are obtained from recordings performed by the electronic stethoscope of claim 1, by alternative electronic stethoscopes, by alternative microphones, and by smartphone microphones, wherein non-lung sound recordings may include sounds such as speech, vehicle traffic, dogs barking, children crying, noise, and music, wherein the audio classifier model comprises a pre-trained audio neural network (PANN), a dataset of known audio recordings, and information regarding health conditions and demographics of patients with known lung conditions, and wherein providing sound recordings to the audio classifier model occurs on a regular repeating schedule and comprises providing new sound recordings and new known health information.

In another aspect, the present embodiments are directed to a system for diagnosing heart and/or lung conditions using sound including: an electronic stethoscope; an electronic device communicatively coupled to the electronic stethoscope via a data connection; a digital video camera communicatively coupled to the electronic device via a data connection; a visual localization algorithm to identify locations of key points on the body of a user and to identify locations of the electronic stethoscope; an audio classification algorithm to classify and identify sounds corresponding to heart and/or lung conditions; and a user interface configured to guide the user to position the electronic stethoscope and to record heart and/or lung sounds; wherein the electronic stethoscope comprises a bell and membrane, a light-emitting device, a microphone, and an analog-to-digital converter, wherein the electronic device is selected from one of a mobile device or a personal computer, and comprises a digital display, a physical user interface, digital processor, memory, and storage, wherein the digital video camera captures a video image that contains at least the torso of a user and light from the light-emitting device on the electronic stethoscope, and transmits the video image to the electronic device, wherein the data connection comprises a wireless connection or a wired connection, wherein the electronic device is communicatively connected via a network connection to a server.

In another aspect, the present embodiments are directed to a system for recording heart and/or lung sounds including: an electronic stethoscope; an electronic device communicatively coupled to the electronic stethoscope via a data connection; a digital video camera communicatively coupled to the electronic device via a data connection; a visual localization algorithm to identify locations of key points on the body of a user and to identify locations of the electronic stethoscope; and a user interface configured to guide the user to position the electronic stethoscope and to record sounds; wherein the electronic stethoscope comprises a bell and membrane, a light-emitting device, a microphone, and an analog-to-digital converter, wherein the electronic device is selected from one of a mobile device or a personal computer, and comprises a digital display, a physical user interface, digital processor, memory, and storage, wherein the digital video camera captures a video image that contains at least the torso of a user and light from the light-emitting device on the electronic stethoscope, and transmits the video image to the electronic device, wherein the data connection comprises a wireless connection or a wired connection, wherein the electronic device is communicatively connected via a network connection to a server.

In another aspect, the present embodiments are directed to a method for diagnosing heart conditions including: providing an electronic stethoscope comprising a chest piece with a bell covered by a membrane, a light-emitting device on a side opposite the membrane, a microphone, an analog-to-digital converter, a microcontroller, and an electronic connection; providing an electronic device comprising a digital video camera, at least one input mechanism and a digital display; connecting the electronic stethoscope to the electronic device via the electronic connection; turning the light-emitting device on and off in a specified pattern; using a visual localization algorithm to guide a user to position the electronic stethoscope at heart valve listening locations on the chest of the user; recording a duration of heart sounds at each of the heart valve listening locations; providing the heart sound recordings to a trained audio classification algorithm; outputting, by the trained audio classification algorithm, a classification of each of the heart sound recordings corresponding to at least one of normal heart function or one or more of a plurality of heart conditions.

In another aspect, the present embodiments are directed to a method for recording heart sounds including: providing an electronic stethoscope comprising a chest piece with a bell portion covered by a membrane, a light-emitting device on disposed on a side of the bell portion, a microphone, an analog-to-digital converter, a microcontroller, and an electronic connection; providing an electronic device comprising a digital video camera, at least one input mechanism and a digital display; connecting the electronic stethoscope to the electronic device via the electronic connection; turning the light-emitting device on and off in a specified pattern; using a visual localization algorithm to guide a user to position the electronic stethoscope at heart valve listening locations on the chest of the user; and recording a duration of heart sounds at each of the heart valve listening locations.

In another aspect, the present embodiments are directed to a method for diagnosing lung conditions including: providing an electronic stethoscope comprising a chest piece with a bell portion covered by a membrane, a light-emitting device on disposed on a side of the bell portion, a microphone, an analog-to-digital converter, a microcontroller, and an electronic connection; providing an electronic device comprising a digital video camera, at least one input mechanism and a digital display; connecting the electronic stethoscope to the electronic device via the electronic connection; turning the light-emitting device on and off at in specified pattern; using a visual localization algorithm to guide a user to position the electronic stethoscope at lung listening locations on the chest and back of the user; recording a duration of lung sounds at each of the lung listening locations; providing the lung sound recordings to a trained audio classification algorithm; outputting, by the trained audio classification algorithm, a classification of each of the lung sound recordings corresponding to at least one of normal lung function or one or more of a plurality of lung conditions.

In another aspect, the present embodiments are directed to a method for recording lung sounds including: providing an electronic stethoscope comprising a chest piece with a bell covered by a membrane, a light-emitting device on a side opposite the membrane, a microphone, an analog-to-digital converter, a microcontroller, and an electronic connection; providing an electronic device comprising a digital video camera, at least one input mechanism and a digital display; connecting the electronic stethoscope to the electronic device via the electronic connection; turning the light-emitting device on and off at in specified pattern; using a visual localization algorithm to guide a user to position the electronic stethoscope at lung listening locations on the chest and back of the user; and recording a duration of lung sounds at each of the lung listening locations.

In another aspect, the present embodiments are directed to a method for positioning an electronic stethoscope at target heart valve locations and recording heart sounds including: (a) acquiring a live video feed from a camera showing the head and the torso of a user and showing a variably switching light on an electronic stethoscope that follows a controlled switching program; (b) providing the live video feed to a pose estimation algorithm, which outputs the key points of a pose of the user, the key points including the locations of at least the left shoulder and the right shoulder of the user; (c) displaying the live video feed on the display screen and overlaying the key points on the corresponding locations on the live video feed displayed on the display screen; (d) providing the live video feed and the key points to a heart valve location estimation algorithm, which outputs a plurality of heart valve listening locations; (e) displaying the live video feed on the display screen and overlaying the key points and plurality of heart valve listening locations on the corresponding locations on the live video feed displayed on the screen; (f) providing the live video feed, the key points, the plurality of heart valve listening locations, and the controlled program of the variably switching light-emitting device to a stethoscope location estimation algorithm, which outputs a stethoscope location relative to the key points and to the heart valve listening locations; (g) providing the live video feed, the key points, the plurality of heart valve listening locations, the controlled program of the variably switching light-emitting device, and the stethoscope location to a guided stethoscope positioning and sound recording algorithm; (h) determining, by the guided stethoscope positioning and sound recording algorithm, whether the electronic stethoscope is correctly positioned at a first heart valve listening location of the plurality of heart valve listening locations; (i) sending, by the guided stethoscope positioning and sound recording algorithm, a first signal indicative of incorrect stethoscope positioning to aid the user in positioning the electronic stethoscope; (j) repositioning, by the user, the electronic stethoscope; (k) sending, by the guided stethoscope positioning and sound recording algorithm, a second signal indicative of correct stethoscope positioning; (l) sending, by the guided stethoscope positioning and sound recording algorithm, a third signal indicative of pausing movements for a first duration of time; (m) recording, by the guided stethoscope positioning and sound recording algorithm, a sound received by a microphone disposed within the electronic stethoscope for a second duration of time; (n) repeating steps (g) through (m) until a sound recording of the specified duration of time has been recorded at each of the plurality of heart valve listening locations.

In some embodiments, the plurality of heart valve listening locations comprise an aortic valve area, a pulmonic valve area, a tricuspid valve area, and a mitral valve area.

In some embodiments, the first signal comprises a first colored shape displayed on a video screen of an electronic device at the stethoscope location. In some embodiments, the second signal comprises a second colored shape displayed on a video screen of an electronic device at the stethoscope location, wherein the color of the second colored shape differs from the color of the first colored shape. In some embodiments, the first signal, second signal, and third signal each comprise a visual indication produced by the electronic device. In some embodiments, the first signal, second signal, and third signal each comprise an auditory indication produced by the electronic device.

In another aspect, the present embodiments are directed to a method for positioning an electronic stethoscope at target lung listening locations and recording lung sounds including: (a) acquiring a live video feed from a camera showing the head and the torso of a user and showing a variably switching light-emitting device on an electronic stethoscope that follows a controlled switching program; (b) providing the live video feed to a pose estimation algorithm, which outputs the key points of a pose of the user, the key points including the locations of at least the left shoulder and the right shoulder of the user; (c) displaying the live video feed on a display screen and overlaying the key points on the corresponding locations on the live video feed displayed on the display screen; (d) providing the live video feed and the key points to a lung listening location estimation algorithm, which outputs a plurality of lung listening locations; (e) displaying the live video feed on the display screen and overlaying the key points and plurality of lung listening locations on the corresponding locations on the live video feed displayed on the screen; (f) providing the live video feed, the key points, the plurality of lung listening locations, and the controlled program of the variably switching light-emitting device to a stethoscope location estimation algorithm, which outputs a stethoscope location relative to the key points and to the lung listening locations; (g) providing the live video feed, the key points, the plurality of lung listening locations, the controlled program of the variably switching light-emitting device, and the stethoscope location to a guided stethoscope positioning and sound recording algorithm; (h) determining, by the guided stethoscope positioning and sound recording algorithm, whether the electronic stethoscope is correctly positioned at a first lung listening location of the plurality of lung listening locations; (i) sending, by the guided stethoscope positioning and sound recording algorithm, a first signal indicative of incorrect stethoscope positioning to aid the user in positioning the electronic stethoscope; (j) repositioning, by the user, the electronic stethoscope; (k) sending, by the guided stethoscope positioning and sound recording algorithm, a second signal indicative of correct stethoscope positioning; (l) sending, by the guided stethoscope positioning and sound recording algorithm, a third signal indicative of pausing movements for a first duration of time; (m) recording, by the guided stethoscope positioning and sound recording algorithm, a sound received by a microphone disposed within the electronic stethoscope for second duration of time, where the second duration of time; (n) repeating steps (g) through (m) until a sound recording of the specified duration of time has been recorded at each of the plurality of lung listening locations.

In some embodiments, the plurality of lung listening locations comprise locations near the apexes of the lungs, the upper lobes of the lungs, the middle lobes of the lungs, and the lower lobes of the lungs, on the left and the right sides of the user's front and back torso. In some embodiments, the first signal comprises a colored shape displayed on a video screen of an electronic device at the stethoscope location. In some embodiments, the second signal comprises a colored shape displayed on a video screen of an electronic device at the stethoscope location, wherein the color of the colored shape differs from the color of the first colored shape. In some embodiments, the first signal, second signal, and third signal each comprise a visual indication produced by the electronic device. In some embodiments, the first signal, second signal, and third signal each comprise an auditory indication produced by the electronic device.

In another aspect, the present embodiments are directed to a method of position a stethoscope at one or more heart listening locations, the method including: providing a live video feed of a user's torso; determining, by a heart valve location estimation algorithm, the one or more heart listening locations based on the live video feed; displaying the live video feed on a video screen with the one or more heart listening locations overlaid thereon; providing an electronic stethoscope in a field of view of the live video feed, the electronic stethoscope comprising a variably switching light-emitting device; moving the electronic stethoscope within a field of view of the live video feed such that the variably switching light-emitting device is in the vicinity of the one or more heart listening locations; rendering, on the live video feed, the one or more heart listening locations overlaid thereon in a different color to indicate that the electronic stethoscope is positioned correctly.

In some embodiments, determining, by a heart valve location estimation algorithm, the one or more heart listening locations based on the live video feed includes using a pose estimation algorithm, which outputs key points of a pose of the user, the key points including the locations of at least the left shoulder and the right shoulder of the user.

In another aspect, the present embodiments are directed to a method of diagnosing the health of at least one human organ via a computational framework that includes hand-coded diagnostics and/or machine learning techniques, the method comprising: receiving audio data from at least one of a heart and a lung, the audio data received from an electronic stethoscope, processing the audio data via at least one of: a) segmentation of the audio data via at least one of frequency, amplitude, and duration; and b) a U-Net neural network that takes the audio data as input, preprocesses it into a spectrogram for frequency equivariance, and outputs a corrected segmentation; evaluating the data via at least one of: c) a statistical diagnostic algorithm using clinical practice guidelines; and d) a machine-learning technique comprising a neural network that is trained via a set of matched pairs, each matched pair comprising at least one data point from the electronic stethoscope and at least one data point from diagnostic equipment; and displaying at least one result based on the evaluation of the data set.

In some embodiments, the displayed result comprises a diagnosis probability of at least one of the following diagnoses: normal heart, innocent murmur, aortic stenosis, and mitral valve prolapse.

In some embodiments, the diagnostic equipment comprises ultrasound equipment and/or an echocardiogram.

In some embodiments, the electronic stethoscope comprises a piezoelectric contact microphone.

BRIEF DESCRIPTION OF THE DRAWINGS

The present teachings described herein will be more fully understood from the following description of various illustrative embodiments, when read together with the accompanying drawing. It should be understood that the drawing described below is for illustration purposes only and is not intended to limit the scope of the present teachings in any way.

DEFINITIONS

Figure 1:
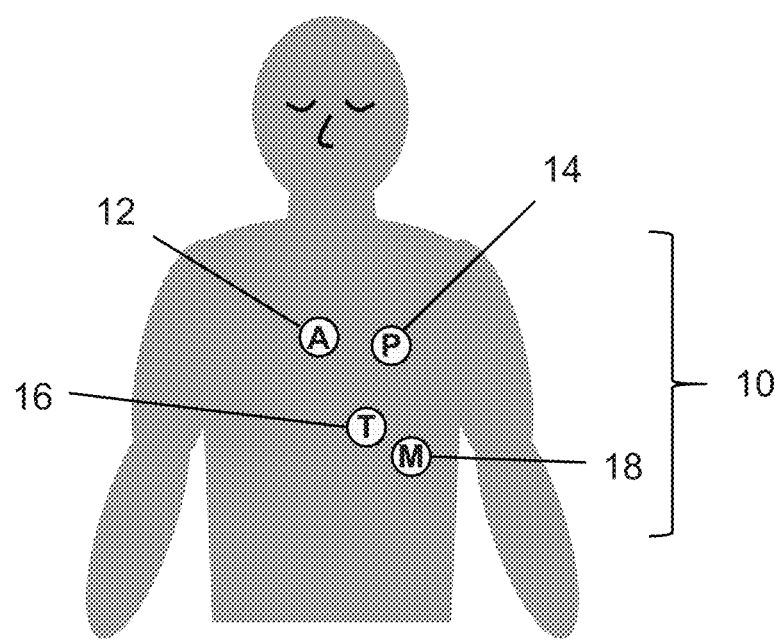
FIG. 1 is a diagram of heart valve listening locations.

About, Approximately: As used herein, the terms "about" and "approximately" as used in reference to a value, refers to a value that is similar, in context to the referenced value. In general, those skilled in the art, familiar with the context, will appreciate the relevant degree of variance encompassed by "about" and "approximately" in that context. For example, in some embodiments, the terms "about" and "approximately" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Auscultation: As used herein, the term "auscultation" refers to listening to internal sounds emitted by a body, usually using a stethoscope or other similar audio tool.

Electronic health record (EHR) and electronic medical record (EMR): As used herein, the term "electronic health record (EHR)" and "electronic medical record (EMR)" refer to systems of health information that are stored in a digital format and that can be transmitted and accessed through networks or devices. EHRs and EMRs may contain medical history, demographics, laboratory test results, personal statistics, allergies, medication history, etc. EHRs and EMRs may be used by medical providers to record and access medical information regarding patients.

Key point: As used herein, the term "key point" (also "key position") refers to specific landmarks on a user's face and body that can be identified and used to define the user's pose. Key points are used within the PoseNet pose identification algorithm, and include the nose, the eyes, the ears, the shoulder joints, the hip joints, the elbows, the hands, the knees, and the feet. See also pose below.

Kiosk: As used herein, the term "kiosk" (also "electronic kiosk" or "interactive kiosk") refers to a housing that contains a computer, one or more input devices, and one or more output devices. A kiosk is intended to allow a user to access various functions embodied by the kiosk without being able to access or change internal features or system functions. An interactive kiosk or electronic kiosk is generally a self-contained system intended for a specific purpose.

Pose: As used herein, the term "pose" (also "human position", "position", or "body configuration") refers to a physical configuration of a human body. Examples of poses include standing, lying, leaning, sitting, crouching, etc. More specifically, within the context of the present disclosures, a user's pose refers to the geometric arrangement of the user's shoulders, head, neck, and hips in relation to each other such that their relative positions and angles can be used to accurately depict an overall body configuration and can be used to locate other features within the user's body. The pose can be defined by identifying several specific landmarks, or key points, at important locations on a user's body. See also key points above.

Stethoscope: As used herein, the term "stethoscope" refers to a medical implement for listening to sounds from a body. It generally includes a resonator that is placed on the skin of a subject, and some mechanism to conduct sounds either into the ears of an operator or into a device for recording sounds.

User: As used herein, the term "user" refers to an individual operating or using one or more of the embodiments in this disclosure. Within the context of the present embodiments, a user is generally a human who is capable of operating and positioning an electronic stethoscope in contact with the user's body. The user provides inputs to, interacts with, and receives information from an electronic device. In some embodiments, a user may be a secondary user to assist a primary user in operating one or more of the embodiments in this disclosure, wherein the primary user is the user whose heart and/or lung sounds are recorded by an electronic stethoscope.

DETAILED DESCRIPTION OF CERTAIN EMBODIMENTS

It is contemplated that methods, compositions, and processes of the claimed embodiments encompass variations and adaptations developed using information from the embodiments described herein. Adaptation and/or modification of the methods, compositions, and processes described herein may be performed, as contemplated by this description.

Throughout the description, where methods, compositions, and processes are described as having, including, or comprising specific components, or where processes and methods are described as having, including, or comprising specific steps, it is contemplated that, additionally, there are compositions of the present disclosures that consist essentially of, or consist of, the recited components, and that there are processes and methods according to the present disclosures that consist essentially of, or consist of, the recited steps.

It should be understood that the order of steps or order for performing certain action is immaterial so long as the embodiments remain operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are provided for the convenience of the reader; the presence and/or placement of a header is not intended to limit the scope of the subject matter described herein.

Figure 2A:
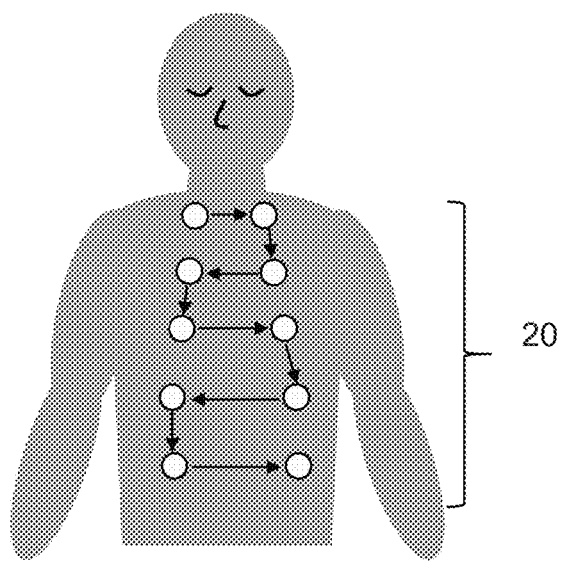
FIG. 2A is a diagram of anterior chest auscultation locations.
Figure 2B:
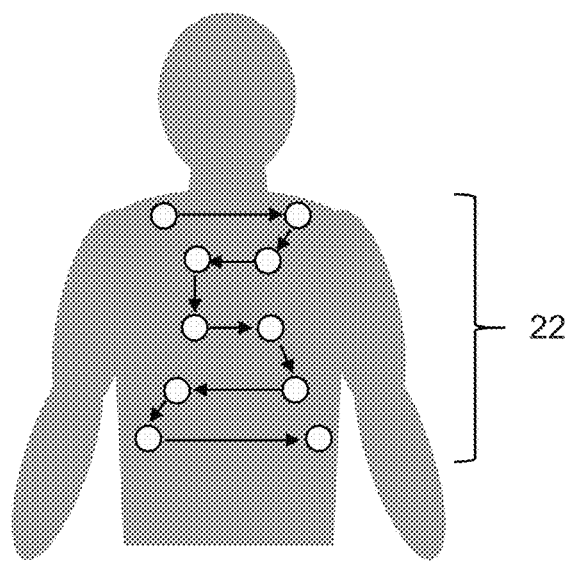
FIG. 2B is a diagram of posterior chest auscultation locations.

The present disclosure provides technologies for the recording of sounds from the heart and lungs of a user using an electronic stethoscope at locations on the chest of the user that are identified in real time by a computer vision algorithm. FIG. 1 shows the four main heart listening locations 10 associated with the heart valves: the aortic valve area 12, the pulmonic valve area 14, the tricuspid valve area 16, and the mitral valve area 18. A fifth area, the left sternal border area, located just below the pulmonic area, may also be used. FIG. 2A shows ten lung listening locations 20 on the front (anterior) chest and a recommended order of listening, and FIG. 2B shows ten lung listening locations 22 on the back (posterior) chest and a recommended order of listening. The chest listening locations (20 and 22) may include locations on the left side and the right side of the chest corresponding to the apexes of the lungs just above the clavicles, the upper lobes of the lungs, the middle lobes of the lungs, and the lower lobes of the lungs. The present disclosure also provides technologies for diagnosis of heart and lung conditions by auscultation using an electronic stethoscope and analysis of sound recordings by machine learning algorithms.

Systems and Methods for Implementations of Electronic Stethoscope and Algorithms This section describes systems and methods for implementations of an electronic stethoscope and at least one algorithm, according to aspects of the present embodiments.

Figure 3:
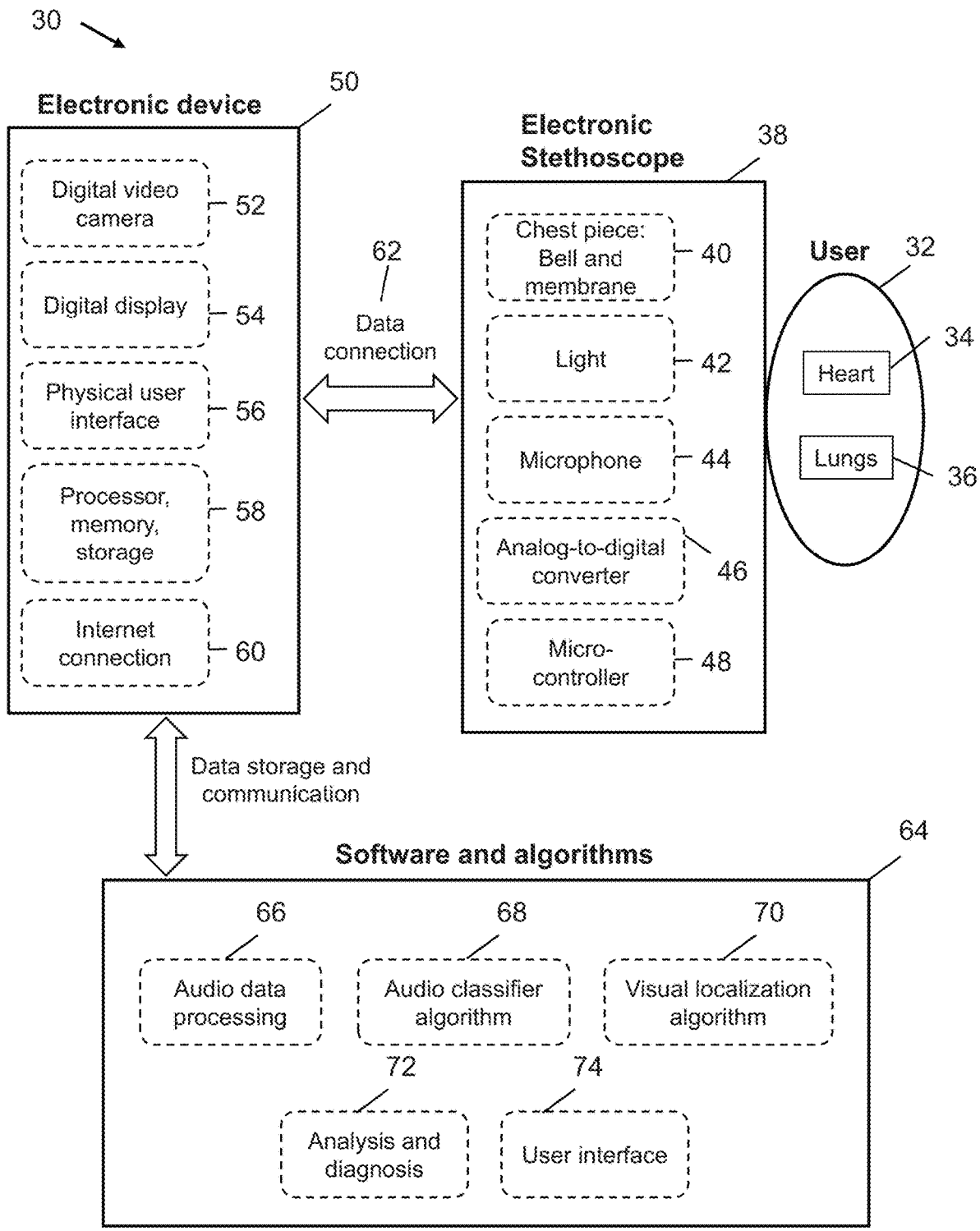
FIG. 3 is a schematic diagram of a general embodiment of a system of an electronic device, an electronic stethoscope, and associated software and algorithms, according to aspects of the present embodiments.

FIG. 3 is a schematic diagram of a general embodiment of a system of an electronic device 50, an electronic stethoscope 38, and associated software and algorithms 64, according to aspects of the present embodiments. In some embodiments, this system may be used to guide a user to position the electronic stethoscope on specific target listening locations on the user's chest and back. In some embodiments, the guiding of the positioning of the electronic stethoscope is achieved by a visual localization algorithm 70

(i.e., a computer vision algorithm) which locates the position of a blinking light 42 on the electronic stethoscope 88 relative to positions of joints on the user's body (e.g., the shoulders, the hips, etc.). In some embodiments, a digital video camera 102 is used to capture video for use with the visual localization algorithm 70, and an electronic device 50 receives the video stream from the digital video camera 52 and provides an interface 74 between the user 32 and algorithms 64. In some embodiments, a microphone 44 in the electronic stethoscope 38 records sounds from the heart 34 and/or lungs 36 of the user once the chest piece 40 of the electronic stethoscope 38 is positioned at a target listening location. In some embodiments, an audio processing algorithm 66 may process the recorded sounds before an audio classification algorithm 68 may analyze the recorded sounds and classify them according to various heart or lung conditions.

Figure 4:
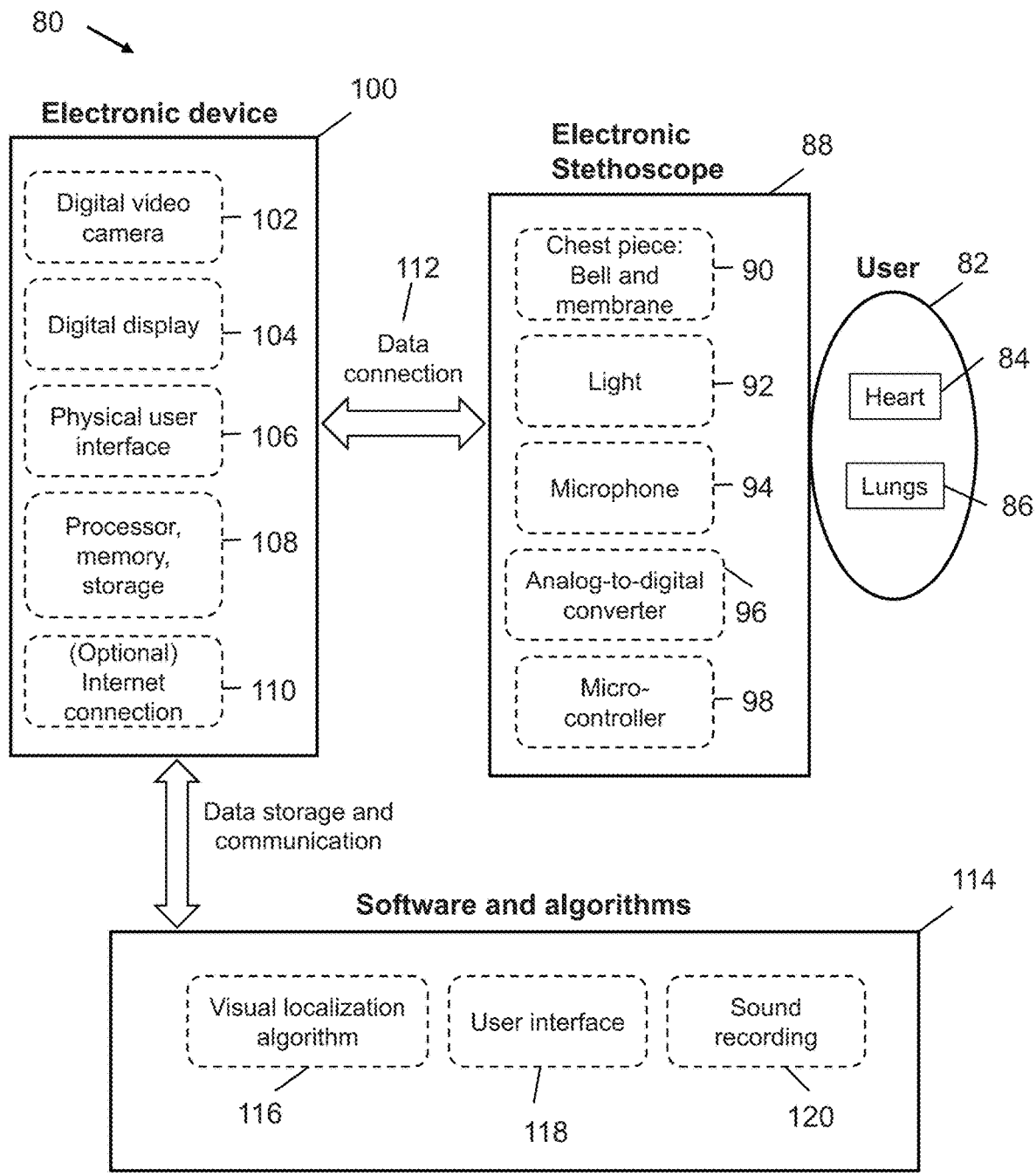
FIG. 4 is a schematic diagram of a general embodiment of a system of an electronic device, an electronic stethoscope, and associated software and algorithms, according to aspects of the present embodiments.

FIG. 4 is a schematic diagram with another general embodiment of a system of an electronic device, an electronic stethoscope, and associated software and algorithms, according to aspects of the present embodiments. In some embodiments, the system depicted in FIG. 4 does not include an audio classification algorithm. In some embodiments, the system depicted in FIG. 4 includes an electronic stethoscope, an electronic device and a camera, and a visual localization algorithm. In some embodiments, the system depicted in FIG. 4 would enable a user to be able to accurately position an electronic stethoscope at locations on the user's chest corresponding to each of the four main heart valve listening locations. At each location, a microphone integrated inside the electronic stethoscope can record sounds produced by the user's heart. In some embodiments represented by FIG. 4, the sound recordings are not analyzed by any audio algorithm, but the sound recordings may be saved for later analysis by another system, transmission to an electronic medical record (EMR), transmission to a doctor's office, output to speakers or headphones, waveforms of sounds output to a display or printed on paper, use during telemedicine appointments, etc.

Figure 5A:
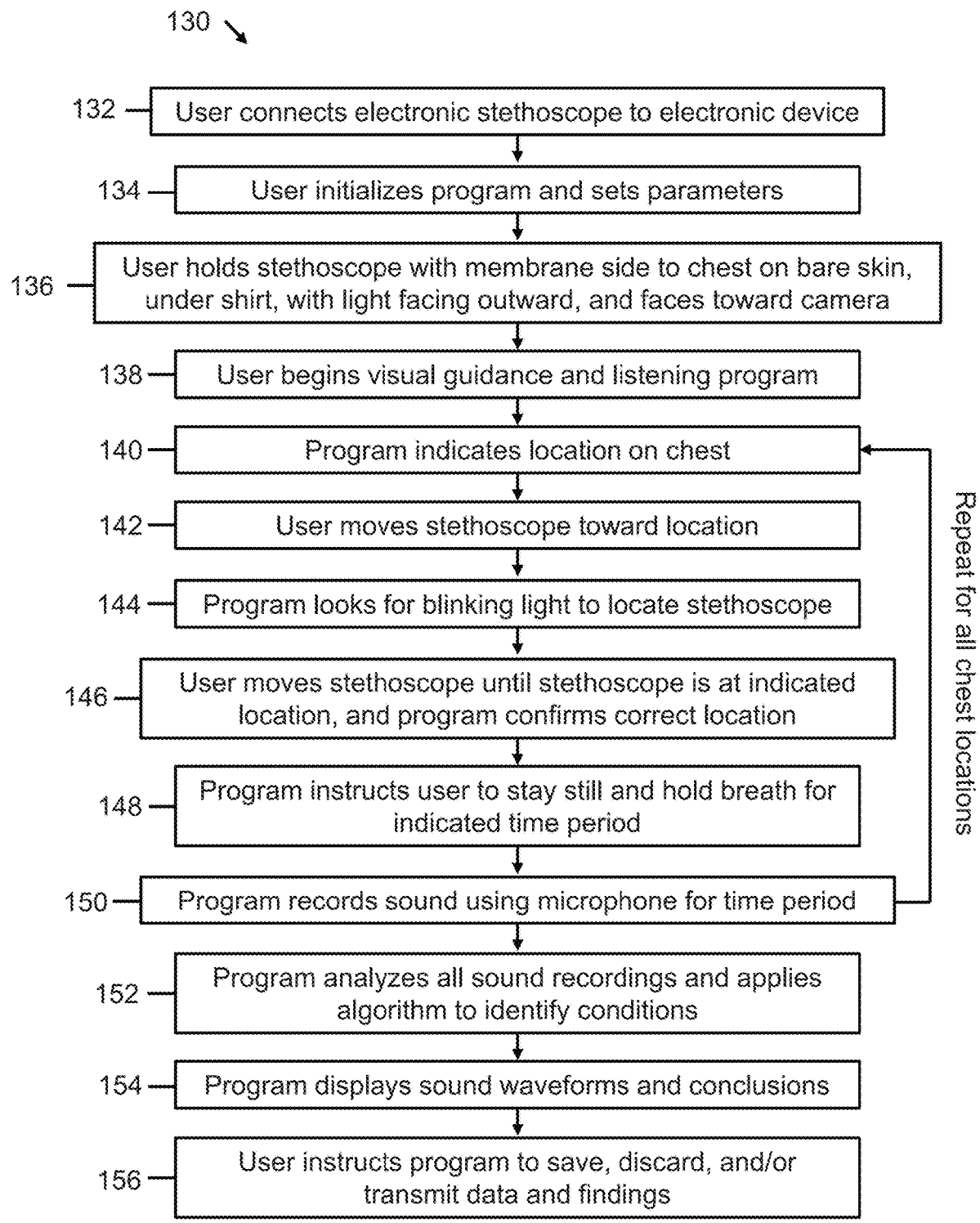
FIG. 5A is a flow chart describing a method to use an electronic stethoscope and associated software to record chest sounds and obtain a diagnosis, according to aspects of the present embodiments.

FIG. 5A is a flow chart describing a method 130 to use an electronic stethoscope and associated software to record chest sounds and obtain a diagnosis, according to aspects of the present embodiments. In some embodiments, in step 132 a user may connect an electronic stethoscope to an electronic device and then in step 134 the user may initialize a program on the electronic device and set parameters. In some embodiments, in step 136 the user may hold the stethoscope with a membrane side to the user's chest on bare skin under any clothing with a light-emitting device on the stethoscope facing outward, and with the user facing toward a digital video camera associated with the electronic device. In step 138 the user then begins the visual guidance and listening program on the electronic device.

Referring still to FIG. 5A, steps 140 through 150 may be repeated for all chest locations. In step 140, the program may indicate a chest location. In step 142, the user may move the stethoscope toward the indicated location. In step 144, the program may use a live video feed from the camera and the blinking of the light-emitting device to locate points on the user's body and the stethoscope. In step 146, the user may moves the stethoscope until it is at the indicated location and the program confirms the correct location. In step 148, the program may instruct the user to stay still and hold breath for an indicated time period. In step 150, the program may record sound using a microphone disposed in the stethoscope for another indicated time period.

Referring still to FIG. 5A, in step 152 the program then may analyze all sound recordings and may apply an algorithm to identify conditions. In step 154, the program displays waveforms of the sounds and displays conclusions regarding the likelihood of various conditions. In step 156, the user instructs the program to save, discard, and/or transmit data and findings.

Figure 5B:
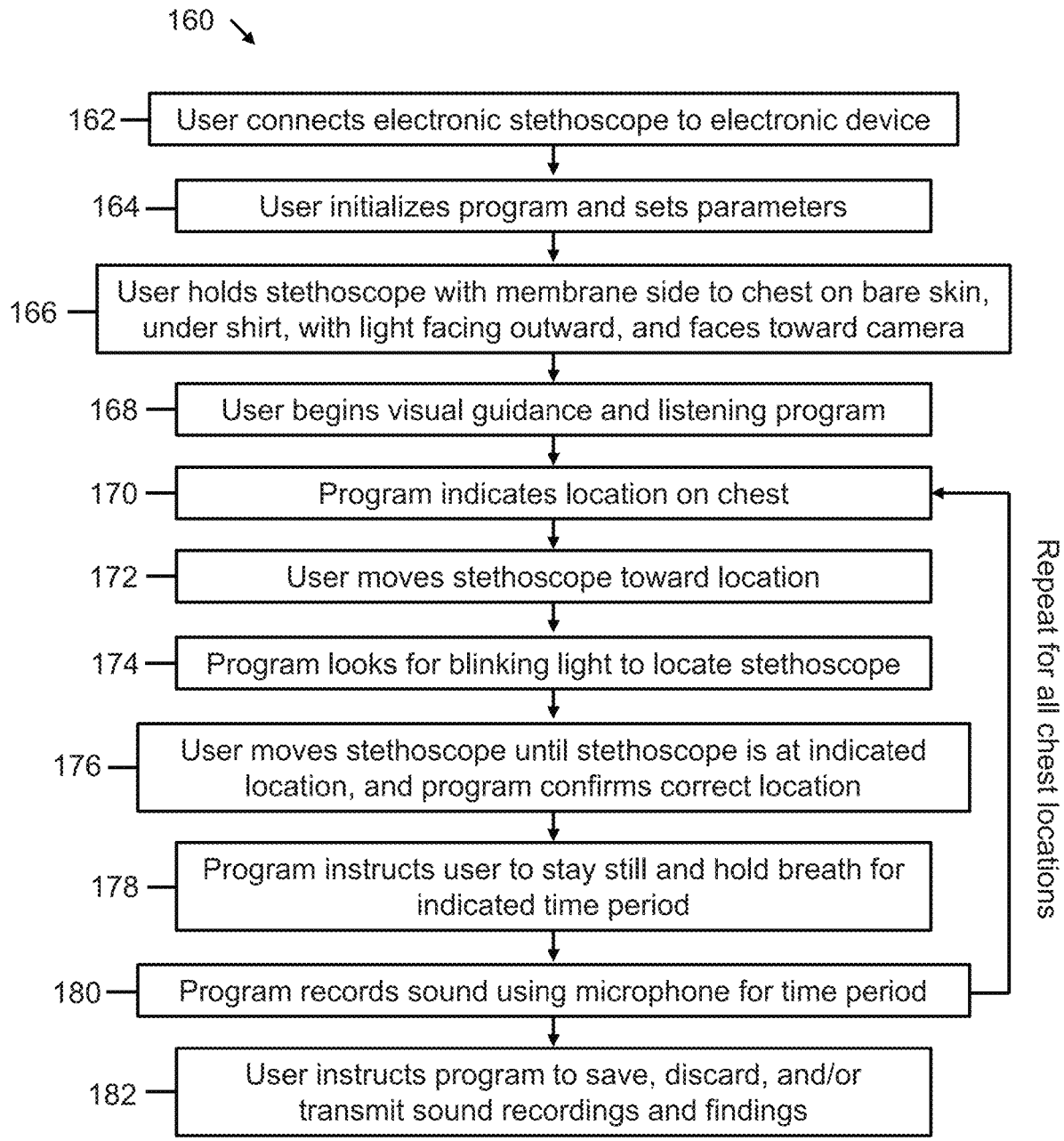
FIG. 5B is a flow chart describing a method to use an electronic stethoscope and associated software to record chest sounds, according to aspects of the present embodiments.

FIG. 5B is a flow chart describing a method 160 to use an electronic stethoscope and associated software to record chest sounds, according to aspects of the present embodiments. In some embodiments, in step 162 a user may connect an electronic stethoscope to an electronic device and then in step 164 the user may initialize a program on the electronic device and sets parameters. In some embodiments, in step 166 the user may hold the stethoscope with a membrane side to the user's chest on bare skin under any clothing with a light-emitting device on the stethoscope facing outward, and with the user facing toward a digital video camera associated with the electronic device. In step 168 the user then may begin the visual guidance and listening program on the electronic device.

Referring still to FIG. 5B, steps 170 through 182 are repeated for all chest locations. In step 170, the program may indicate a location on chest. In step 172, the user may move the stethoscope toward the indicated location. In step 174, the program uses a live video feed from the camera and the blinking of the light-emitting device to locate points on the user's body and the stethoscope. In step 176, the user may move the stethoscope until it is at the indicated location and the program may confirm the correct location. In step 178, the program may instruct the user to stay still and hold breath for an indicated time period. In step 180, the program records sound using a microphone disposed in the stethoscope for the indicated time period. In step 182, the user instructs the program to save, discard, and/or transmit data and findings.

Hardware Implementations

The present disclosures provide certain technologies that have hardware, or physical, implementations in order to carry out the functions of the disclosures. These hardware components include, primarily, an electronic stethoscope, an electronic device, and a camera.

Electronic Stethoscope

Figure 6A:
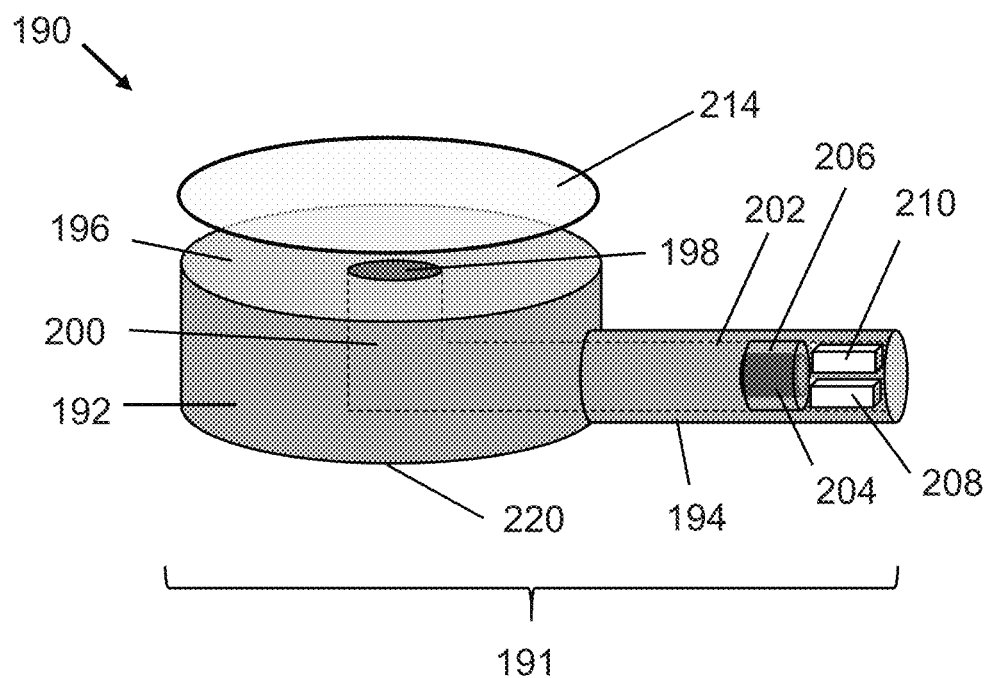
FIG. 6A is a diagram showing an exploded cutaway perspective view of an electronic stethoscope, according to aspects of the present embodiments.

An electronic stethoscope is a stethoscope with certain electronic components that enhance in some manner the functionality of the stethoscope. FIGS. 6A-G illustrate various views of certain embodiments of an electronic stethoscope. FIG. 6A is a diagram showing an exploded cutaway perspective view of an electronic stethoscope 190, according to aspects of the present embodiments. The main parts of the electronic stethoscope 190 may include the chest piece 191, which then may include two cylindrical portions: a bell portion 192 a stem portion 194.

The diameter of the bell portion 192 may be about 1.625 inches, or between about 1 inches and about 2 inches. The height of the bell portion 192 may be about 1.75 inches, or between about 1 and about 2 inches. The bell portion 192 may have a concave face 196 on one end a flat face 220 on the other end. In some embodiments, the concave face 196 may have a shallow profile 218 (see FIG. 6C) that may have an inverted conical shape or may have an inverted spherical cap shape. In some embodiments, the depth of the concave face 196 may be about 0.0625 inches, or between about 0.05 inches and 0.1 inches.

Referring still to FIG. 6A, the stem portion 194 may be connected to the outer circumferential wall of the bell portion 192 such that the longitudinal axis of the bell portion 192 is perpendicular to the central axis of the stem portion 194. In some embodiments, the center of the concave face 196 may have a circular hole 198 leading to a cylindrical bore 200 extending longitudinally through the center of the bell portion 196, and turning perpendicularly to continue toward the circumference of the bell portion 192 where it may extend into the interior of a stem portion 194 to form an interior lumen 202 of the stem portion 194. In some embodiments, the diameter of the cylindrical bore 200 within the bell portion 192 may be approximately 0.25 inches, or between 0.1 inches and 0.5 inches. The dimensions of the lumen 202 within the stem portion 194 may vary to accommodate the dimensions of a microphone 204 and microphone seal 206 disposed within the lumen 202.

Referring still to FIG. 6A, the electronic stethoscope may include a thin, circular membrane 214 with a diameter that is equal to or slightly smaller than the diameter of the bell portion 192. In some embodiments, the membrane (214 may be attached around its circumference to the circumference of the bell portion 192 at the concave face 196 by an adhesive. The membrane 214 may include a plastic sheet (e.g., acetate, polyester, polyethylene terephthalate (PET), polyethylene, polypropylene, polystyrene, epoxy fiberglass, resin, thermoset plastic, polyvinyl chloride (PVC), or polytetrafluoroethylene (PTFE)). The thickness of the membrane 214 may be approximately 0.025 inches, or between approximately 0.01 inches and approximately 0.05 inches. The adhesive may include a polymer-based glue (e.g., latex, cyanoacrylate, epoxy resin, a hot-melt glue, rubber cement, polyvinyl acetate, polyvinyl alcohol (PVA), polyvinyl chloride (PVC), or polyvinyl chloride emulsion. In some embodiments, the membrane 214 thus attached to the concave face 196 may enclose a volume of air.

Figure 6B:
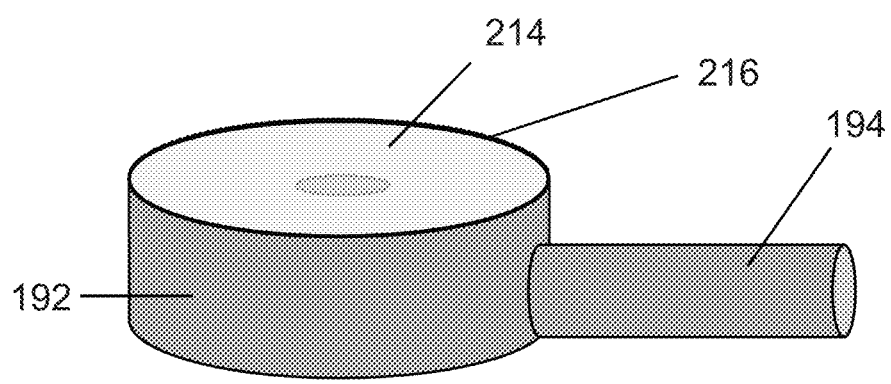
FIG. 6B is a diagram showing a perspective view of an assembled electronic stethoscope with a membrane covering a concave face of a bell portion of a chest piece of the electronic stethoscope, according to aspects of the present embodiments.
Figure 6C:
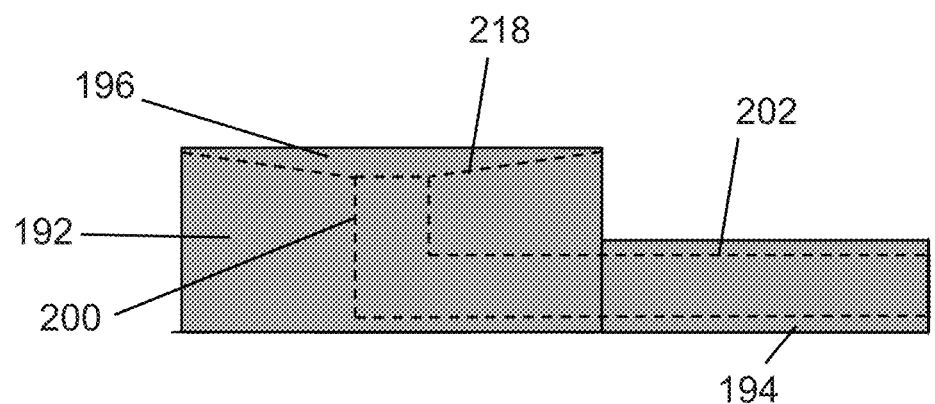
FIG. 6C is a diagram showing a side view of an electronic stethoscope with dashed lines indicating interior features, according to aspects of the present embodiments.

FIG. 6B is a diagram showing a perspective view of an assembled electronic stethoscope 190 with a membrane 214 covering a concave face 196 of the bell portion 192. FIG. 6C is a diagram showing a side view of an assembled electronic stethoscope 190 with dashed lines indicating interior features, including the profile 218 of the concave face 196, the central bore 200 and how it connects to the lumen 202 of the stem portion 194.

Referring again to FIG. 6A, a microphone 204 may be disposed within the lumen 202 of the stem portion 194. In some embodiments, the microphone 204 may be one of a condenser microphone, a dynamic microphone, a ribbon microphone, a carbon microphone, a piezoelectric microphone, or a microelectromechanical systems (MEMS) microphone. The microphone 204 may be surrounded by a microphone seal 206 disposed circumferentially around the microphone within the lumen 202 of the stem portion 194. In some embodiments, the microphone seal 206 may include a flexible and/or compliant material such that it forms a close contact with both the exterior of the microphone 204 and the interior wall of the lumen 202 and such that air may not escape between the microphone 204 and the interior wall of the lumen 202.

Referring again to FIG. 6A, the electronic stethoscope 190 further comprises an analog-to-digital converter (ACD) 208 and a microcontroller 210 each disposed within the lumen 202 of the stem portion 194 of the electronic stethoscope 190. The ADC 208 may convert the sound received by the microphone 204 into a digital signal that may then be transmitted to the microcontroller 210. In some embodiments, the digital signal may be transmitted from the microcontroller 210 to an electronic device via an electronic connection that may be a wired or a wireless connection. In some embodiments, the wired connection may include at least one of a serial bus connection, a universal serial bus (USB) connection, a parallel bus connection, an audio connection, an Ethernet connection, and an optical fiber connection. In some embodiments, the wireless connection may include at least one of a close-range wireless connection, a Bluetooth connection, a Wi-Fi connection, and a cellular connection. The microcontroller may also receive instructions from the electronic device to control the light-emitting device by switching it on and off in a specified pattern. In some embodiments, the pattern of light switching on and off may be blinking at a frequency between approximately 2 Hz and approximately 30 Hz. In some embodiments, the pattern of light switching on and off may be an arbitrary pattern.

Figure 6D:
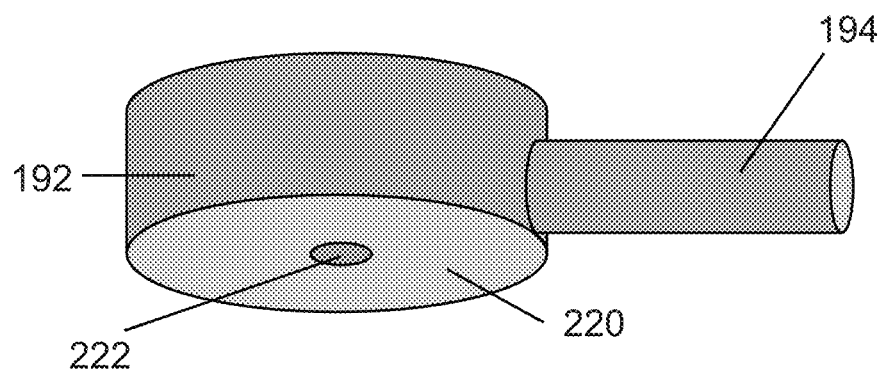
FIG. 6D is a diagram showing an assembled electronic stethoscope with a light-emitting device on a flat face of a bell portion of a chest piece of the electronic stethoscope, according to aspects of the present embodiments.

FIG. 6D shows a flat face 220 of an assembled electronic stethoscope 190. Disposed within the center of the flat face 220 may be a light-emitting device 222. In some embodiments, the light-emitting device 222 may be switched on and off in a particular pattern (e.g., blinking or flashing, or another arbitrary pattern, etc.), intended to be observed by a video camera for visual localization of the position of the bell portion of the stethoscope on a user's body. The light-emitting device 222 may include at least one of a light-emitting diode, an incandescent light, a fluorescent light, a halogen light, or a gas-discharge lamp. The preferred embodiment of the light-emitting device may be a light-emitting diode.

Referring still to FIG. 6D, in some embodiments, the membrane 214 attached to the bell portion 192 may be placed directly against the skin on the chest of a user underneath the user's clothing to achieve better transmission of sound, with the light-emitting device 222 facing away from the user such that the light emitted from the light-emitting device 222 passes through the user's clothing and may be visible to a viewer or camera. The user's clothing may be intended to be thin in enough to allow light from the light-emitting device to pass through. The wavelength of light emitted may be between approximately 400 nm and approximately 1000 nm, corresponding to visible light and near-infrared (nIR) light. This range of wavelengths is chosen to be visible to a user and to a video camera and to be able to pass through reasonably thin fabric or textile used for making clothing. The user may also use the electronic stethoscope without clothing. In some embodiments, the brightness of the light emitted is bright enough to pass through a single layer of fabric typically used for clothing, and dim enough to not cause any discomfort when viewed by a typical user without any intervening fabric.

Figure 6E:
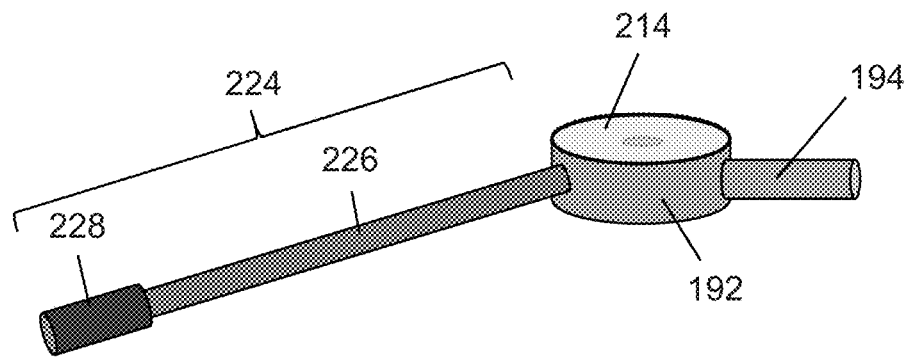
FIG. 6E is a diagram showing an electronic stethoscope with a rigid rod and handle attached, according to aspects of the present embodiments.
Figure 6F:
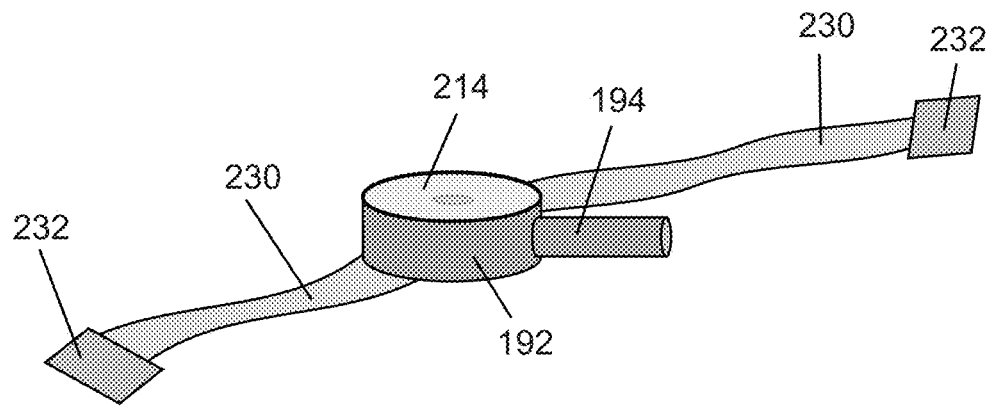
FIG. 6F is a diagram showing an electronic stethoscope with a flexible strap and clasps attached, according to aspects of the present embodiments.
Figure 6G:
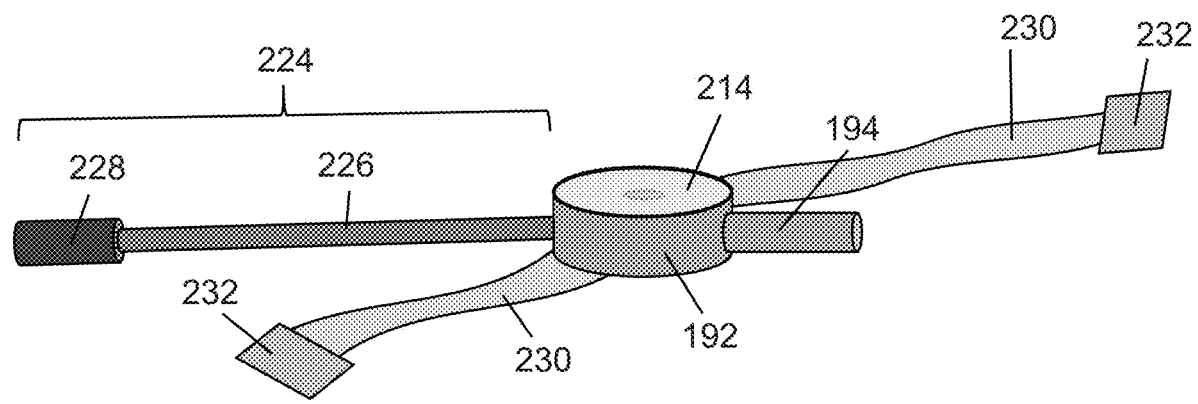
FIG. 6G is a diagram showing an electronic stethoscope with a flexible strap and clasps attached and a rigid rod and handle attached, according to aspects of the present embodiments.

Additional embodiments of an electronic stethoscope with a rigid rod and a flexible strap are shown in FIGS. 6E-6G. The rigid rod and the flexible strap may assist a user in moving and positioning an electronic stethoscope. In FIG. 6E, a rigid rod 224 with an optional handle portion 228 attached to an elongate rod portion 226 is attached extending from the circumference of the bell portion 192. In some embodiments, the rigid rod 224 may include at least one of a metal, a plastic, or a wood material. In some embodiments, the rod 226 and handle 228 may be held in a hand of a user to help position the stethoscope on regions of the user's body that may be otherwise difficult to reach (e.g., on a user's back, etc.).

In FIG. 6F, a flexible strap 230 with one or more strap pieces is attached to the bell portion 196. In some embodiments, the flexible strap may include one or more lengths of strap and one or more clasp mechanisms 232 to hold the strap closed around a user's torso such that the stethoscope stays in position and does not shift, and does not require a user's hand to continuously hold it in position. In some embodiments, the strap may be elastic to provide stretching functionality, which may aid in comfortable and reliable positioning of the stethoscope. In some embodiments, the flexible strap may include at least one of woven fabric, knitted fabric, leather, metal chain mail, elastic fabric, nylon, cotton, webbing, polyurethane, polyvinyl chloride, polyethylene, polypropylene, wool, linen, cork, rubber, neoprene, spandex, elastane, rayon, carbon fiber, a composite material, silicon, rope, hemp, bamboo, cellulose, or paper.

In FIG. 6G, both a rigid rod 224 and a flexible strap 230 are attached to the bell portion 196. In some embodiments, the flexible strap 230 may hold the electronic stethoscope around the user's torso while the rigid rod 224 may be used to reposition or move the electronic stethoscope 190. That is, the flexible strap 230 and the rigid rod 224 may be used in concert to assist in positioning of the electronic stethoscope 190.

Figure 7A:
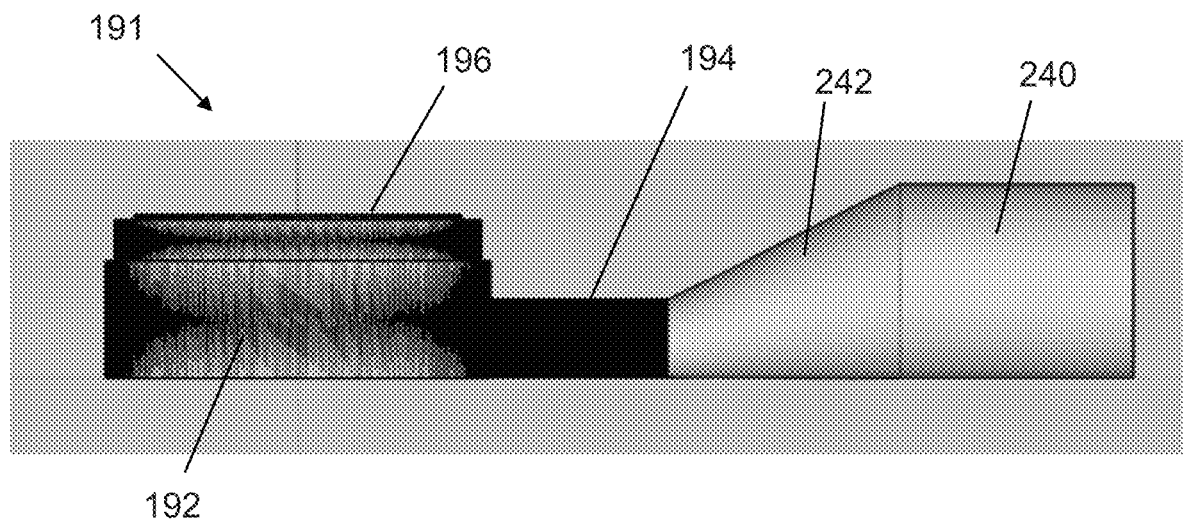
FIG. 7A is a diagram showing a side view of a bell and stem portion of an electronic stethoscope, according to aspects of the present embodiments.
Figure 7B:
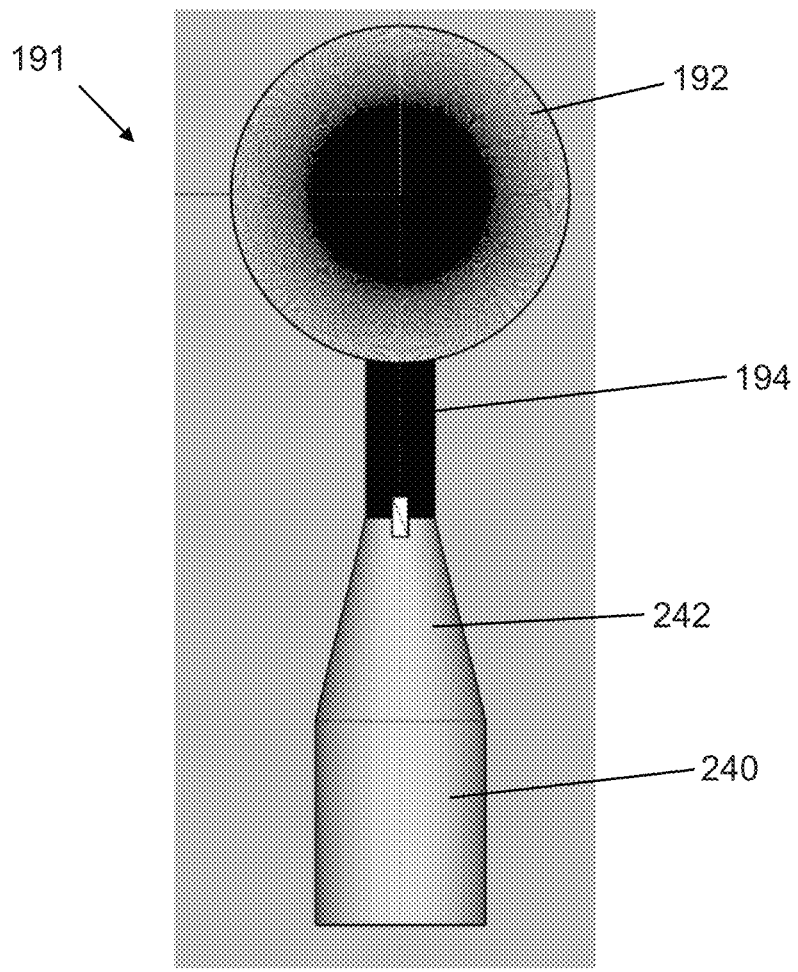
FIG. 7B is a diagram showing a top view of a bell and stem portion of an electronic stethoscope, according to aspects of the present embodiments.

FIG. 7A is a diagram showing a side view of a chest piece 191 (i.e., comprising a bell portion 192 and stem portion 194) of an electronic stethoscope, according to aspects of the present embodiments. FIG. 7A shows a side view of a chest piece 191, with an optional shoulder portion 242 between the region of the stem portion 194 closest to the bell portion 192 and the microphone compartment 240, according to aspects of the present embodiments. The shoulder portion 242 may be adjusted to accommodate different sizes of microphones and microphone compartments 240 depending on the selection of microphone 204. In some embodiments, the chest piece 191 including a bell portion 192 and stem portion 194 may be fabricated as a single continuous piece using at least one of additive manufacturing, molding, casting, or extrusion. FIG. 7B is a diagram showing a top view of a bell portion 192 and stem portion 194 of an electronic stethoscope, according to aspects of the present embodiments.

Figure 8A:
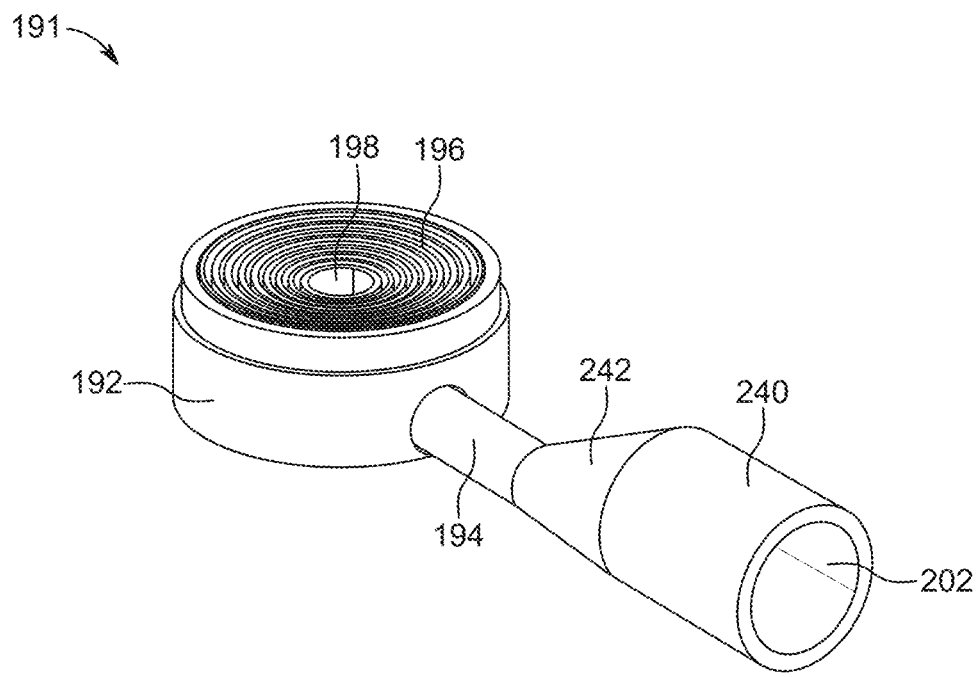
FIG. 8A is a diagram showing a perspective view of a bell and stem portion of an electronic stethoscope, according to aspects of the present embodiments.
Figure 8B:
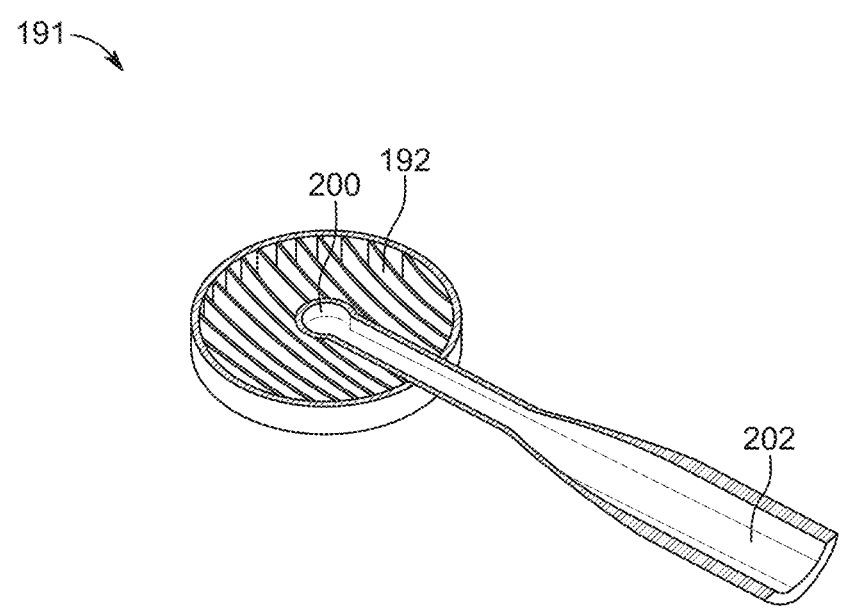
FIG. 8B is a diagram showing a perspective view of an interior cut-away of a bell and stem portion of an electronic stethoscope, according to aspects of the present embodiments.

FIG. 8A is a diagram showing a perspective view of a bell and stem portion of an electronic stethoscope, according to aspects of the present embodiments. In FIG. 8A, the concave face 196 of the bell portion 192 is visible, along with the opening 198 of the cylindrical interior bore 200, the stem portion 194, the optional shoulder portion 242, the microphone compartment 240 and the interior lumen 202 of the stem portion. FIG. 8B is a diagram showing a perspective view of an interior cut-away of a bell and stem portion of an electronic stethoscope, according to aspects of the present embodiments. In FIG. 8B, the upper portion of the chest piece 191 is cut away to reveal the point where the bore 200 turns perpendicularly and traverses along the longitudinal axis of the stem portion 202.

Figure 9:
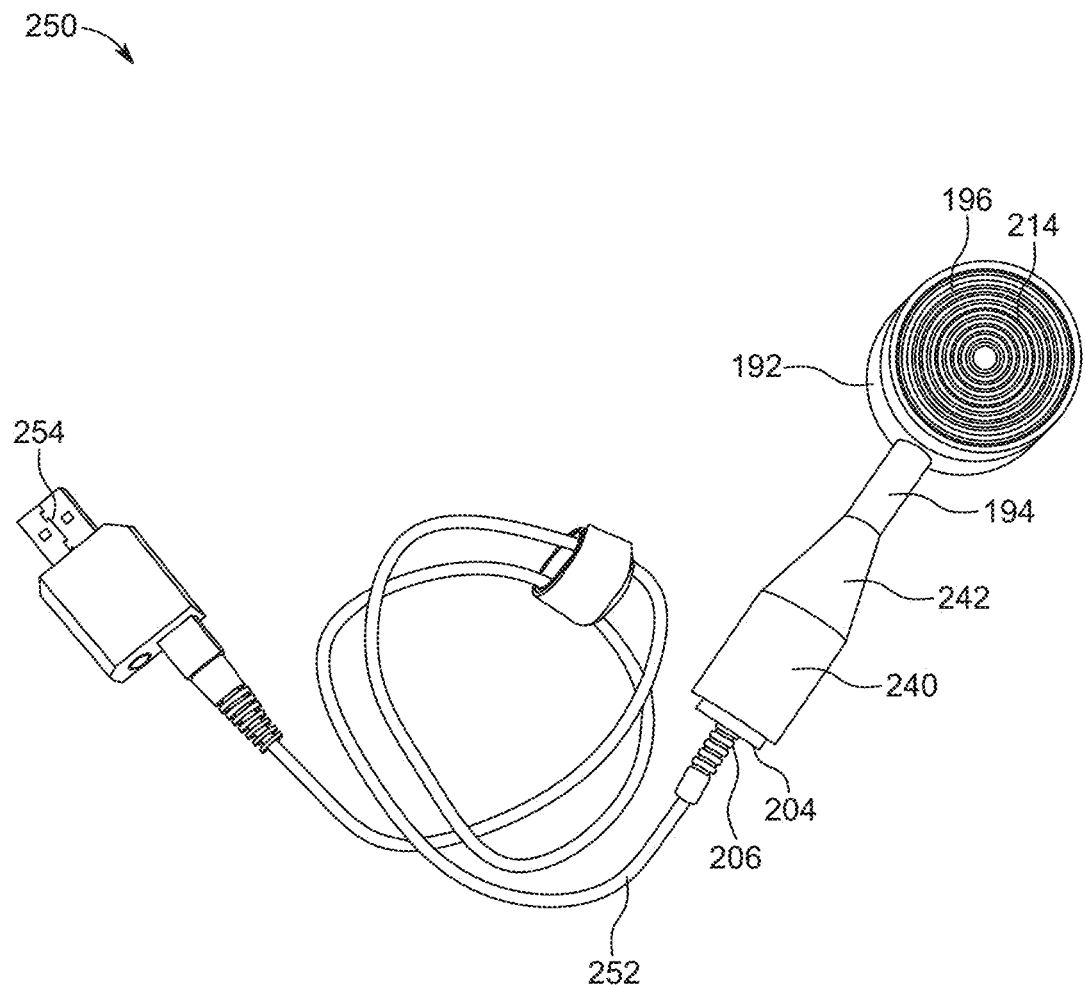
FIG. 9 is a photograph of a prototype electronic stethoscope assembly, according to aspects of the present embodiments.

FIG. 9 is a photograph of a prototype electronic stethoscope assembly 250. In this prototype, a bell portion 192, a stem portion 194, a shoulder portion 242, and a microphone compartment 240 may be one continuous piece that may be fabricated using additive manufacturing out of a polymer material (e.g., polylactic acid (PLA), acrylonitrile butadiene styrene (ABS), or polyethylene terephthalate glycol-modified (PET-G), etc.). A microphone 204 may be disposed within the microphone compartment 240 and may be surrounded by a microphone seal 206. In this prototype example, the microphone is a small microphone (e.g., a Lavalier microphone, wearable microphone, portable microphone, etc.) which has a cylindrical external shape. The microphone seal 206 surrounding the microphone 204 may include a flexible polymeric material (e.g., flexible tubing or similar). The ADC and microcontroller are both contained within the microphone compartment 240 and not visible in the photograph. The electronic connection in this case is a wired connection comprising a universal serial bus (USB) cable 242 and USB connector 254. The USB connection provides a data connection between the microcontroller and an electronic devices, and also provides power to the microcontroller, ADC, and microphone. A membrane 214 made of a 0.025 inch thick circle of a plastic sheet was adhered around the circumference of the membrane to an outer edge circumference of the concave side of the bell portion 192 using glue.

Electronic Device and Camera

The technologies described in the present disclosures include using an electronic device, which may be a personal computer (e.g., laptop computer, notebook computer, desktop computer, etc.) or a handheld device (e.g., smartphone, tablet, mobile device, etc.). In some embodiments, the electronic device is used to receive audio recordings from the microphone in the electronic stethoscope, and to receive video input from a digital camera. In some embodiments, the audio recordings may be processed and transmitted electronically to another computing device such as another electronic device, a server, or and/or a network. In some embodiments, a machine learning algorithm for audio classification may be operating on an external server or may be operating on a local electronic device. In some embodiments, a machine learning algorithm for visual identification of positions in a live video feed may be operating on an external server or may be operating on a local electronic device.

In some embodiments, the electronic device also may include a visual display to show various signals, indications, or information to the user, including indications to guide the user to correctly position the electronic stethoscope at target locations to record sounds associated with heart valves and different parts of the lungs. In some embodiments, the visual display shows instructions to the user to direct the user's movements.

In some embodiments, the visual information provided to the user may include results of listening to sounds from the body of the user and providing a diagnosis. In some embodiments, the visual information may include instructions relating to electronic storage and/or transmission of the results and diagnosis.

In some embodiments, the electronic device may include a means for a user to provide inputs or instructions to the electronic device. Examples of a means to provide input may include a keyboard, a touchscreen, a mouse, a track pad, a microphone, a stylus, a button, a knob, a switch, a dial, a slider, a joystick, and a trackball.

In some embodiments, the electronic device may include a network connection to communicate with external computing devices and systems. The network connection, in some embodiments, may include an Ethernet connection, a Wi-Fi connection, and/or a cellular data connection. In some embodiments, the electronic device may use the network connection to transmit information regarding sound recordings and diagnoses to physicians, clinics, electronic records management systems, or other entities.

In the present disclosures, a digital video camera is used to provide a live video feed to the electronic device. In some embodiments, the digital video camera may be integrated as a part of the electronic device, such as a built-in camera on a smartphone, tablet, laptop, or kiosk, while in other embodiments the digital video camera may be a separate camera that is electronically connected to the electronic device.

FIGS. 21A-21F show diagrams of a user using an electronic stethoscope with a laptop computer, according to aspects of the present embodiments. FIGS. 22A-22F show diagrams of a user using an electronic stethoscope with a mobile device, according to aspects of the present embodiments. FIGS. 23A-23D show diagrams of a user using an electronic stethoscope with a kiosk, according to aspects of the present embodiments.

In some embodiments, the digital video camera may comprise various optical components (e.g., lenses, apertures, light sensors, etc.) and may be connected via an electronic data connection to the electronic device (e.g., via a wired or wireless connection). In some embodiments, the digital video camera may acquire live video images at a frame rate sufficient to capture continuous movements of a user.

Variations of Methods of Use

The present disclosure provides technologies that may be implemented in various forms, for example, by using different types of similar or equivalent hardware, varying certain geometries, or using varying materials.

Figure 21A:
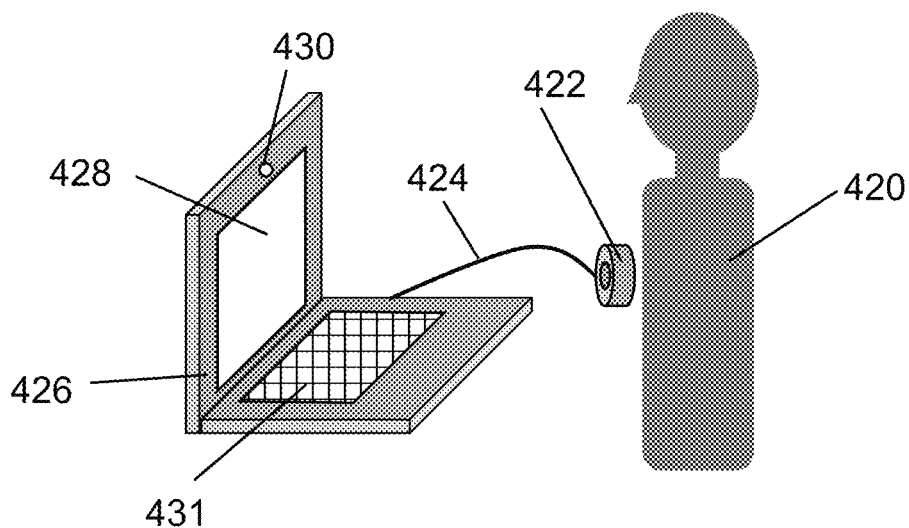
FIG. 21A is a diagram of a user using an electronic stethoscope connected by a wired connection to a laptop computer and measuring sounds on the user's front, according to aspects of the present embodiments.
Figure 21B:
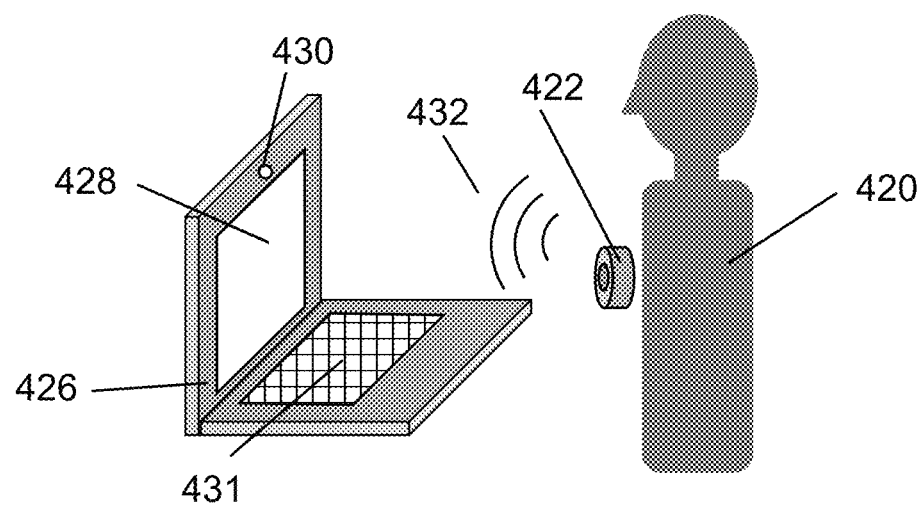
FIG. 21B is a diagram of a user using an electronic stethoscope connected by a wireless connection to a laptop computer and measuring sounds on the user's front, according to aspects of the present embodiments.

In each of the embodiments illustrated in FIGS. 21A-21F, the laptop computer 426 may include an integrated camera 430, method of user input 431 (e.g., keyboard, track pad, track point, buttons, etc.), and display screen 428. In FIG. 21A, the connection between the electronic stethoscope and the electronic device is a wired connection 424. In FIG. 21B, the connection between the electronic stethoscope and the electronic device is a wireless connection 432. In both FIGS. 21A and 21B, the user is using the electronic stethoscope to measure sounds on the user's front. In FIG. 21C-21F, the connection between the electronic stethoscope and the electronic device may be either a wired connection or a wireless connection.

Figure 21C:
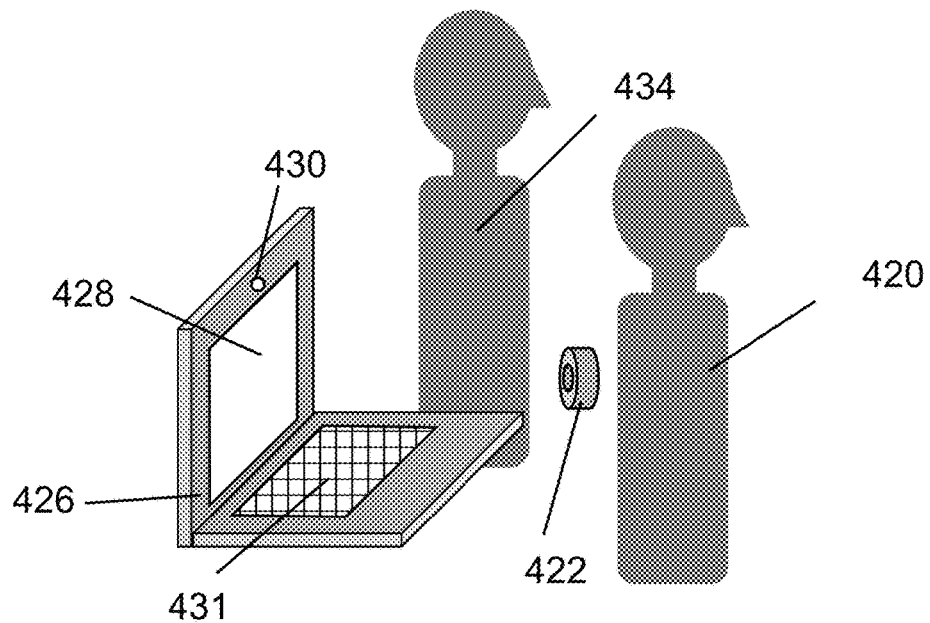
FIG. 21C is a diagram of a user using an electronic stethoscope with a laptop computer and measuring sounds on the user's back with a second user's assistance, according to aspects of the present embodiments.

In FIG. 21C, a second user 434 is assisting in the measurement of sounds on a first user's back 420, according to aspects of the present embodiments. In some embodiments, the first user 420 is facing away from the camera and electronic device (which is illustrated as a laptop computer 426 in this diagram, but may be another electronic device in other embodiments) while the second user 434 moves the electronic stethoscope 422 and observes instructions and feedback provided on the display screen 428 of the electronic device 426.

Figure 21D:
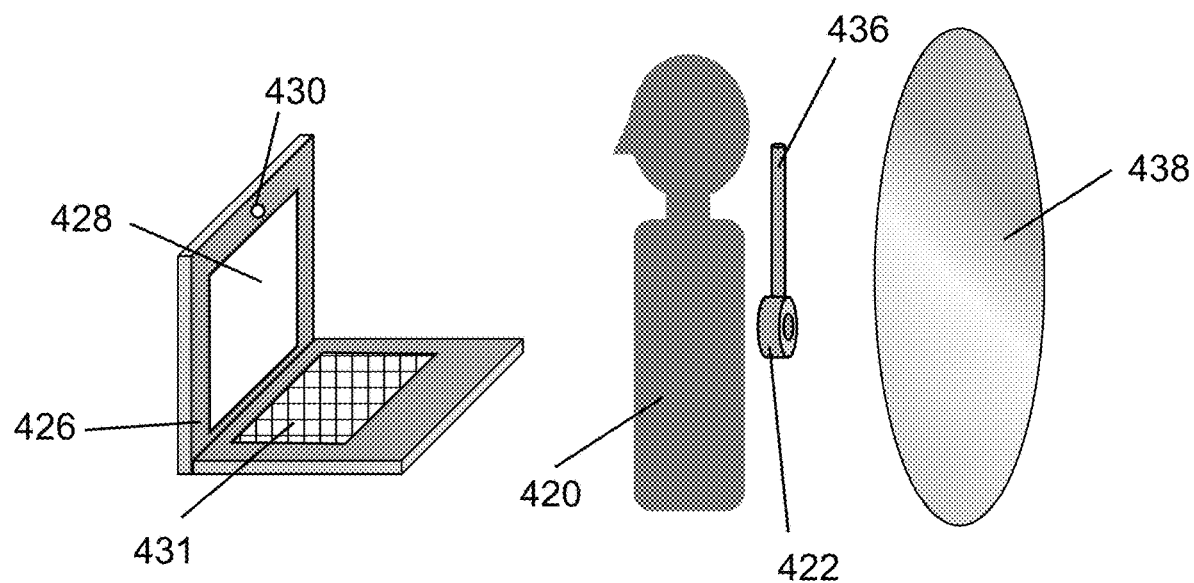
FIG. 21D is a diagram of a user using an electronic stethoscope with a laptop computer and measuring sounds on the user's back by using a rigid rod connected to the stethoscope and a mirror behind the user, according to aspects of the present embodiments.

In FIG. 21D, an electronic stethoscope 422 is used by a user 420 to make sound measurements on the user's back, according to aspects of the present embodiments. In some embodiments, the electronic stethoscope 422 may be connected to a rigid rod 436 that the user may hold in order to move the electronic stethoscope 422. In some embodiments, there may be a mirror 438 behind the user to reflect the position of the user's back and the position of the electronic stethoscope 422 to be captured by a camera 430 associated with the electronic device 426.

Figure 21E:
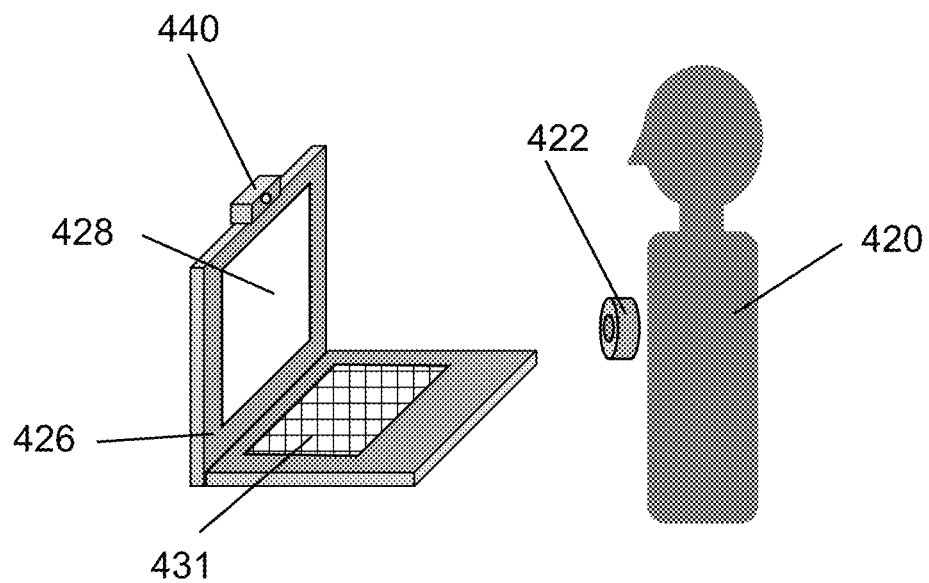
FIG. 21E is a diagram of a user using an electronic stethoscope with a laptop computer and webcam and measuring sounds on the user's front, according to aspects of the present embodiments.

In FIG. 21E, a user 420 uses an electronic stethoscope 422 with a laptop computer 426 and a separate webcam 440 to measure sounds on the user's front, according to aspects of the present embodiments. In some embodiments, the webcam 440 is mounted in contact with the laptop computer 426, for example, at the top edge of the display screen of the laptop computer. In some embodiments, the webcam 440 may be mounted or supported elsewhere but in close proximity to the user 420 and to the laptop computer 426 such that the webcam 440 may capture a clear view of the user's front. In some embodiments, the webcam 440 may be in communication with the laptop computer 426 via either a wired connection or a wireless connection (not visible in this diagram). While a laptop computer 426 is shown in the embodiment illustrated by FIG. 21E, another electronic device capable of performing similar functions may be used instead, in some embodiments.

Figure 21F:
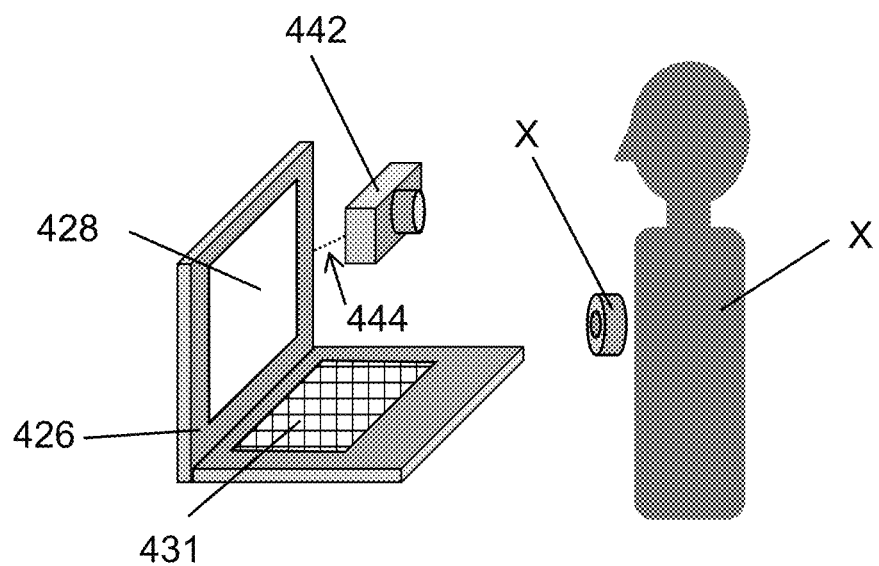
FIG. 21F is a diagram of a user using an electronic stethoscope with a laptop computer and camera and measuring sounds on the user's front, according to aspects of the present embodiments.

In FIG. 21F, a user uses an electronic stethoscope 422 with a laptop computer 426 and a separate camera 442 to measure sounds on the user's front, according to aspects of the present embodiments. In some embodiments, the camera 442 may be mounted on a support, a stand, a tripod, a monopod, and/or a clamp. In some embodiments, the camera 442 may be a digital camera, which may include a digital single lens reflex (DSLR) camera, a digital mirrorless camera, a digital point-and-shoot camera (i.e., a digital compact camera), or a digital bridge camera. In some embodiments, the digital camera 442 may be in communication with the laptop computer 426 via a connection 444 that may be either a wired connection or a wireless connection. While a laptop computer 426 is shown in the embodiment illustrated by FIG. 21F, another electronic device capable of performing similar functions may be used instead, in some embodiments.

In FIGS. 22A-22F, a user 420 is shown using an electronic stethoscope 422 connected by either a wired connection or a wireless connection to a mobile device and measuring sounds on the user's front, according to aspects of the present embodiments. In each of these figures, the mobile device may be one of a smartphone, a tablet, or a handheld computing device. The components of a mobile device suitable for use within the present embodiments include one or more digital processors, digital memory, digital storage, one or more display screens, one or more built-in digital cameras, one or more means of transmitting and receiving information either wirelessly (e.g., Wi-Fi, Bluetooth, etc.) or through a wired connection (e.g., USB, Ethernet, etc.), and one or more means of interacting with a user (e.g., touch-screen, buttons, switches, microphone, etc.). If a digital camera is not built-in, a separate digital camera in electronic communication with the mobile device may be used instead. In some embodiments, a software program may display visual indicators on the display screen (e.g., symbols, outlines, lines, markers, etc.) to guide the user to position the user's torso within the camera view in such a way that visual localization algorithms (e.g., pose estimation algorithms, stethoscope location algorithms, etc.) may operate correctly.

Figure 22A:
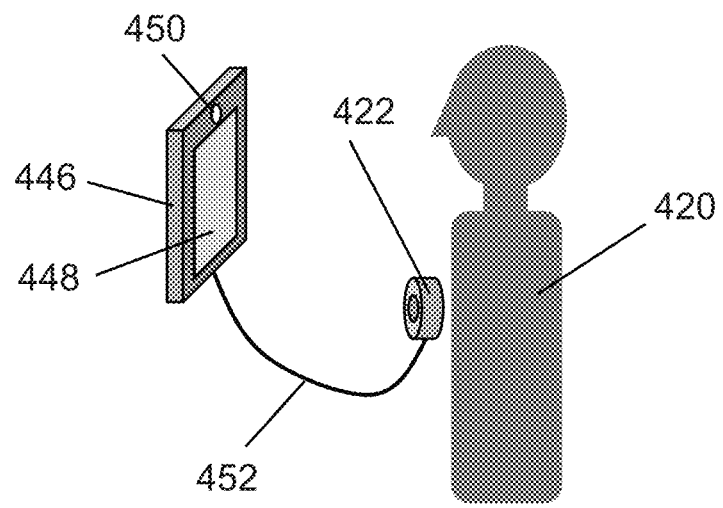
FIG. 22A is a diagram of a user using an electronic stethoscope connected by a wired connection to a mobile device and measuring sounds on the user's front, according to aspects of the present embodiments.
Figure 22B:
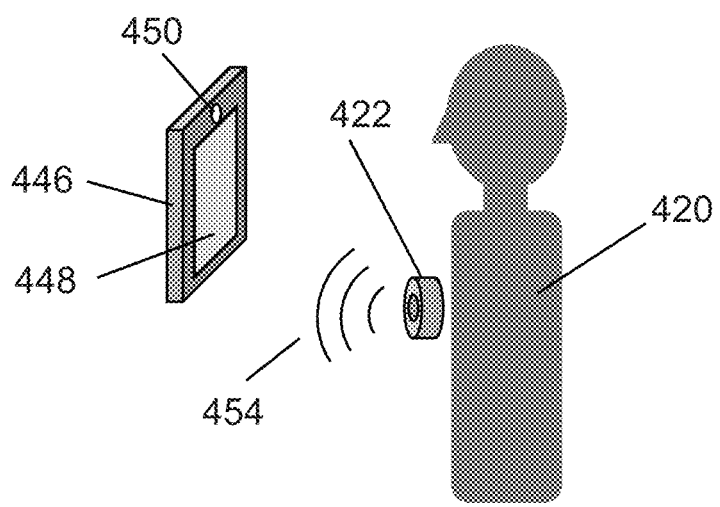
FIG. 22B is a diagram of a user using an electronic stethoscope connected by a wireless connection to a mobile device and measuring sounds on the user's front, according to aspects of the present embodiments.

In FIG. 22A, the electronic stethoscope 422 is connected to the mobile device 446 using a wired connection 452 while the user 420 makes measurements of sounds at the user's front facing toward a built-in camera 450 and display screen 448, according to aspects of the present embodiments. In FIG. 22B, the electronic stethoscope 422 is connected to the mobile device 446 using a wireless connection 454 while the user makes measurements of sounds at the user's front, according to aspects of the present embodiments.

Figure 22C:
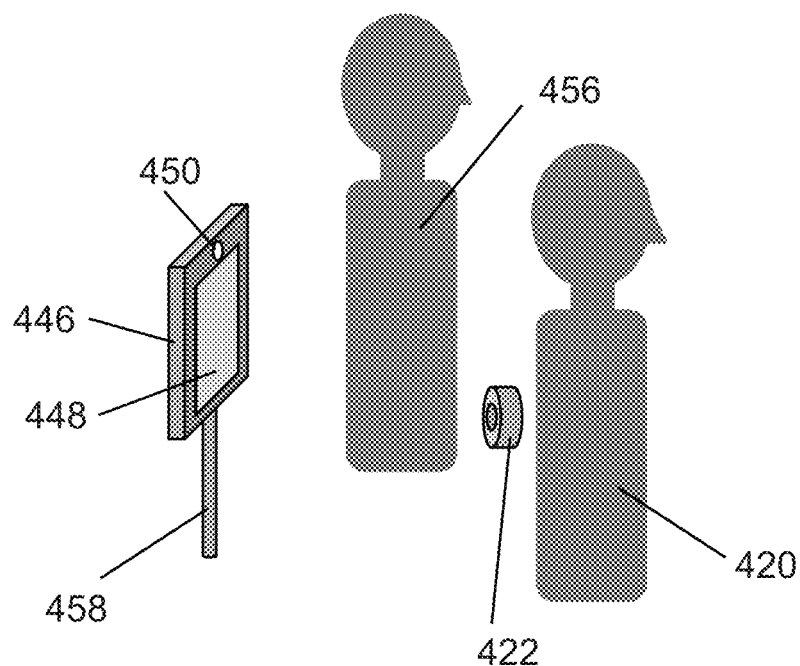
FIG. 22C is a diagram of a user using an electronic stethoscope with a mobile device mounted on a device support and measuring sounds on the user's back with a second user's assistance, according to aspects of the present embodiments.
Figure 22D:
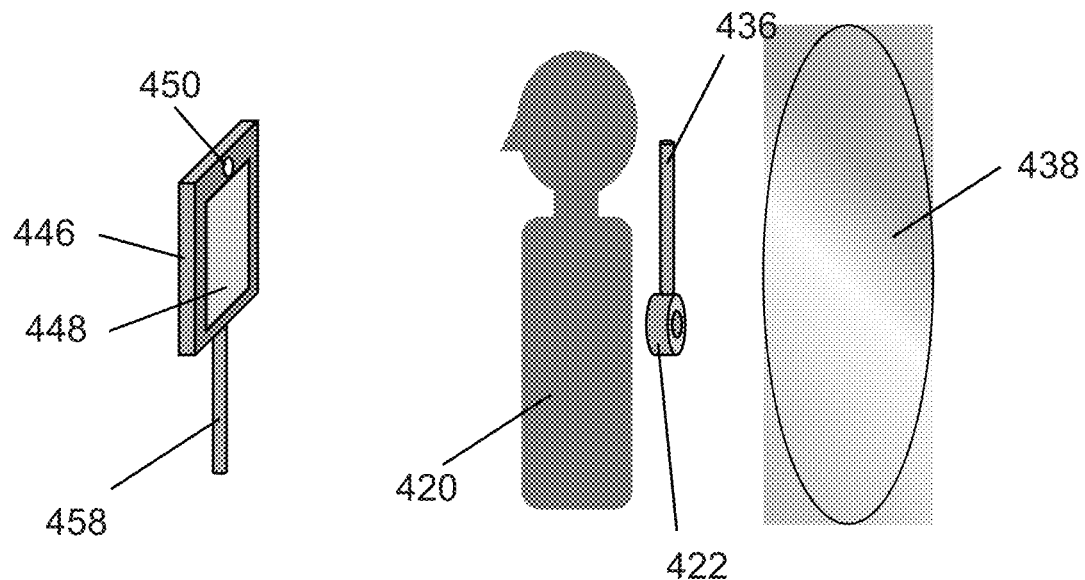
FIG. 22D is a diagram of a user using an electronic stethoscope with a mobile device mounted on a device support and measuring sounds on the user's back by using a rigid rod connected to the stethoscope and a mirror behind the user, according to aspects of the present embodiments.

In FIGS. 22C-22F, an electronic stethoscope 422 is being used with a mobile device 446 mounted on a device support 458 to measure sounds on either the back or the front of a user 420, according to aspects of the present embodiments. In each of these images in FIGS. 22C-22F, the device support 458 allows the mobile device 446 to be held in a stationary, stable position while capturing a live video feed of the user 420 and the electronic stethoscope 422 via a digital camera and displaying the live video feed along with overlaid indicators generated by a computer vision algorithm. In some embodiments, the stable and stationary positioning of both the electronic device 446 and digital video camera improve the operation of the computer vision algorithm. In some embodiments, the device support 458 may refer to any structure that may support a device or electronic device in a specific and adjustable position or configuration and provide stability. Examples of device supports may include tripods, monopods, selfie sticks, stands, grips, holders, clamps, and protective cases with built-in supports. Implementations of device supports may be free-standing or may be partially or entirely handheld. Device stands may also be reversibly attached to another structure, for example by a clamp, a hook-and-loop attachment (Velcro), an adhesive, a magnet, a grip, or a strap. In FIGS. 22C-22D, the connection between the electronic stethoscope 422 and the mobile device 446 may be either a wireless connection or a wired connection.

FIG. 22C is a diagram of a user 420 using an electronic stethoscope 422 with a mobile device 446 mounted on a device support 458 and measuring sounds on the user's back with assistance from a second user 456, according to aspects of the present embodiments. In some embodiments, the user 420 may be facing away from the electronic device 446 while the second user 456 positions and moves the electronic stethoscope 422 and simultaneously observes a display screen 448 on the mobile device 446 to obtain guidance and feedback on where to move the electronic stethoscope 422.

FIG. 22D is a diagram of a user 420 using an electronic stethoscope 422 with a mobile device 446 mounted on a device support 458 and measuring sounds on the user's back by using a rigid rod 436 connected to the stethoscope 420 and a mirror 438 behind the user, according to aspects of the present embodiments. In some embodiments, the user 420 is holding the rigid rod 436 by hand. In other embodiments, there may also be a flexible strap attached to the electronic stethoscope 422 to aid in its use by securing the electronic stethoscope around the user's torso, as in the example electronic stethoscope illustrated in FIG. 6G. In some embodiments, a mirror 438 may be placed behind the user so that the user's back and the stethoscope 422 are reflected by the mirror 438 to be captured by the video camera 450 on the mobile device 458.

Figure 22E:
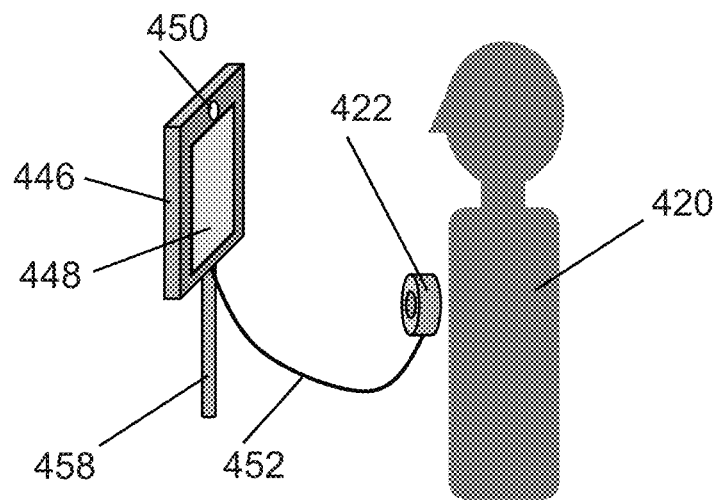
FIG. 22E is a diagram of a user using an electronic stethoscope connected by a wired connection to a mobile device mounted on a device support and measuring sounds on the user's front, according to aspects of the present embodiments.

FIG. 22E is a diagram of a user 420 using an electronic stethoscope 422 connected by a wired connection 452 to a mobile device 446 mounted on a device support 458 and measuring sounds on the user's front, according to aspects of the present embodiments. In some embodiments, the wired connection 452 may connect to a port on the mobile device 446 that may transfer electronic data as well as provide power for the microphone, light-emitting device, analog-to-digital converter, and microcontroller contained within the electronic stethoscope 422. In some embodiments, the wired connection 452 may include at least one of a serial bus connection, a universal serial bus (USB) connection, a parallel bus connection, an audio connection, an Ethernet connection, and an optical fiber connection.

Figure 22F:
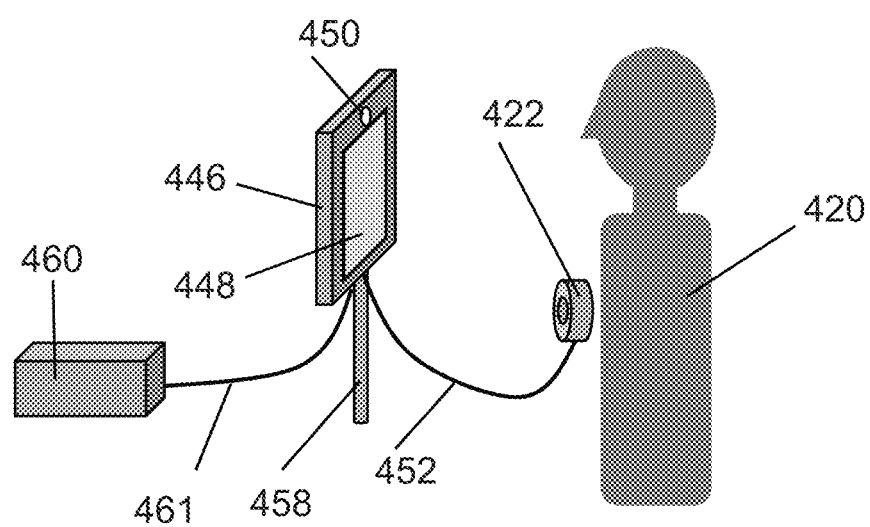
FIG. 22F is a diagram of a user using an electronic stethoscope connected by a wired connection to a mobile device mounted on a device support, and which is connected by a wired connection to a processing device, and the user measuring sounds on the user's front.

FIG. 22F is a diagram of a user 420 using an electronic stethoscope 422 connected by a wired connection 452 to a mobile device 446 mounted on a device support 458, and which is connected by a wired connection 461 to a processing device 460, and the user measuring sounds on the user's front. In some embodiments, the wired connection 452 may connect to a port on the mobile device 446 that may transfer electronic data as well as provide power for the microphone, light-emitting device, analog-to-digital converter, and microcontroller contained within the electronic stethoscope 422. In some embodiments, the wired connection 452 may include at least one of a serial bus connection, a universal serial bus (USB) connection, a parallel bus connection, an audio connection, an Ethernet connection, and an optical fiber connection. In some embodiments, an external processing device 460 may provide additional processing and analysis including visual localization algorithms and audio classifier algorithms. In some embodiments, the external processing device 460 may be connected via a wired connection 461 that may include at least one of a serial bus connection, a universal serial bus (USB) connection, a parallel bus connection, an audio connection, an Ethernet connection, and an optical fiber connection.

In FIGS. 23A-23D, an electronic stethoscope 422 is being used with an interactive kiosk 470 to measure sounds on either the back or the front of a user, according to aspects of the present embodiments. In each of these images in FIGS. 23A-23D, the interactive kiosk 470 may include a computing or processing device, one or more input devices, one or more video cameras, and one or more output devices in a self-contained system. In some embodiments, the one or more input devices may include a keyboard, a touchscreen, a mouse, a track pad, a microphone, a stylus, a button, a knob, a switch, a dial, a slider, a joystick, and a trackball. In some embodiments, the output devices may include a video screen, a liquid crystal display (LCD), a light-emitting diode (LED) display, a speaker, headphones, and a braille reader. In some embodiments, a self-contained system may include a housing and a stand, and may vary in size and shape. In some embodiments, the video camera 474 is positioned near a display screen 472 and is integrated into the interactive kiosk 470. In some embodiments, the interactive kiosk 470 may be deployed to non-medical public locations such as grocery stores, pharmacies, convenience stores, restaurants, hotels, community centers, post offices, libraries, and schools, among others. In some embodiments, when a kiosk 470 and electronic stethoscope 422 are deployed in a non-medical public location, a disposable cover or cap may be used to cover the portion of the electronic stethoscope that may come in direct contact with the user's skin on the user's front or back; a new disposable cover may be used for each user for improved hygiene and cleanliness.

Figure 23A:
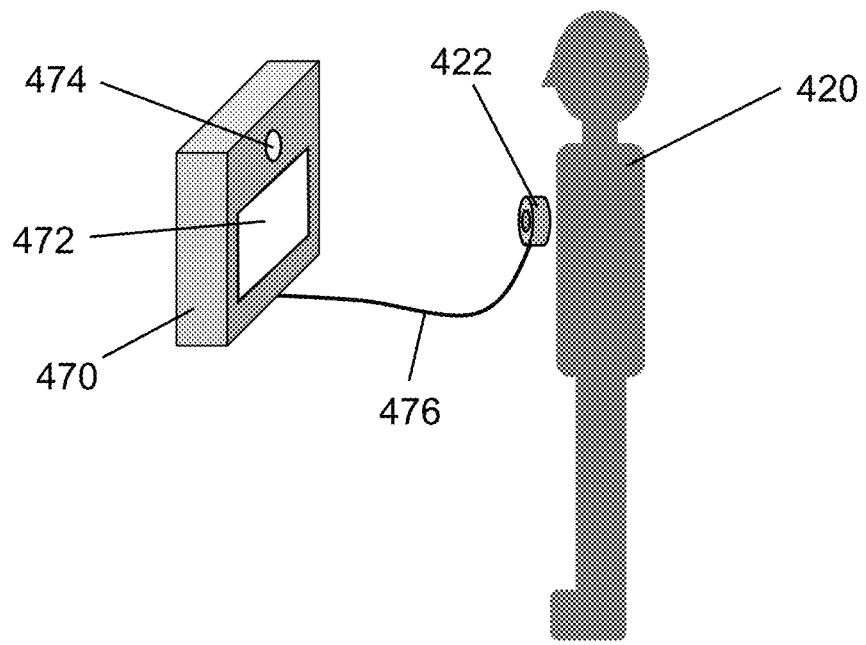
FIG. 23A is a diagram of a user using an electronic stethoscope connected by a wired connection to an interactive kiosk and measuring sounds on the user's front, according to aspects of the present embodiments.

FIG. 23A is a diagram of a user 420 using an electronic stethoscope 422 connected by a wired connection 476 to an interactive kiosk 470 and measuring sounds on the user's front, according to aspects of the present embodiments. In some embodiments, the user 420 may stand in front of the interactive kiosk 470 to face toward the video camera 474 and the display screen 472. In some embodiments, the wired connection 476 may include at least one of a serial bus connection, a universal serial bus (USB) connection, a parallel bus connection, an audio connection, an Ethernet connection, and an optical fiber connection.

Figure 23B:
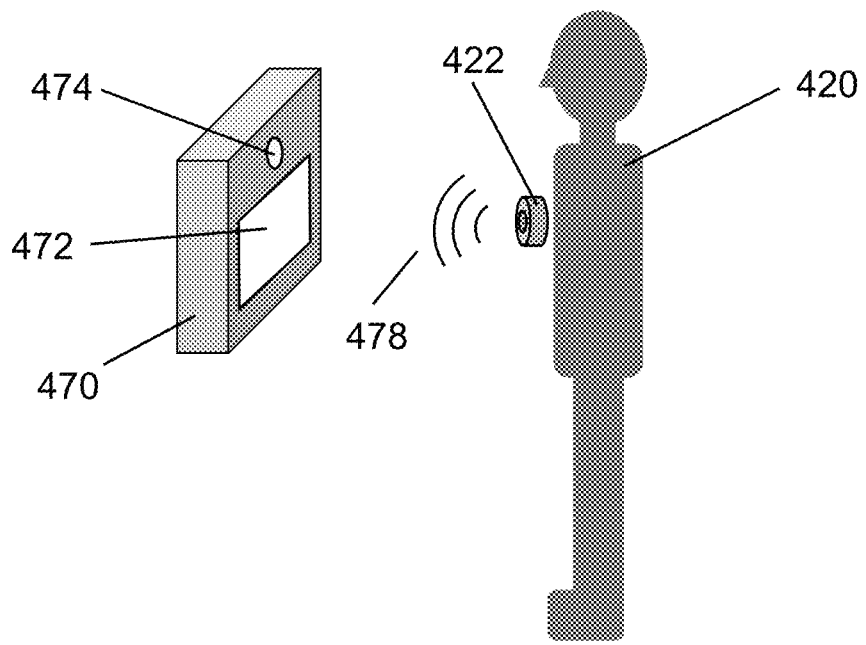
FIG. 23B is a diagram of a user using an electronic stethoscope connected by a wireless connection to an interactive kiosk and measuring sounds on the user's front, according to aspects of the present embodiments.

FIG. 23B is a diagram of a user 420 using an electronic stethoscope 422 connected by a wireless connection 478 to an interactive kiosk 470 and measuring sounds on the user's front, according to aspects of the present embodiments. In some embodiments, the wireless connection 478 may include a Bluetooth connection.

Figure 23C:
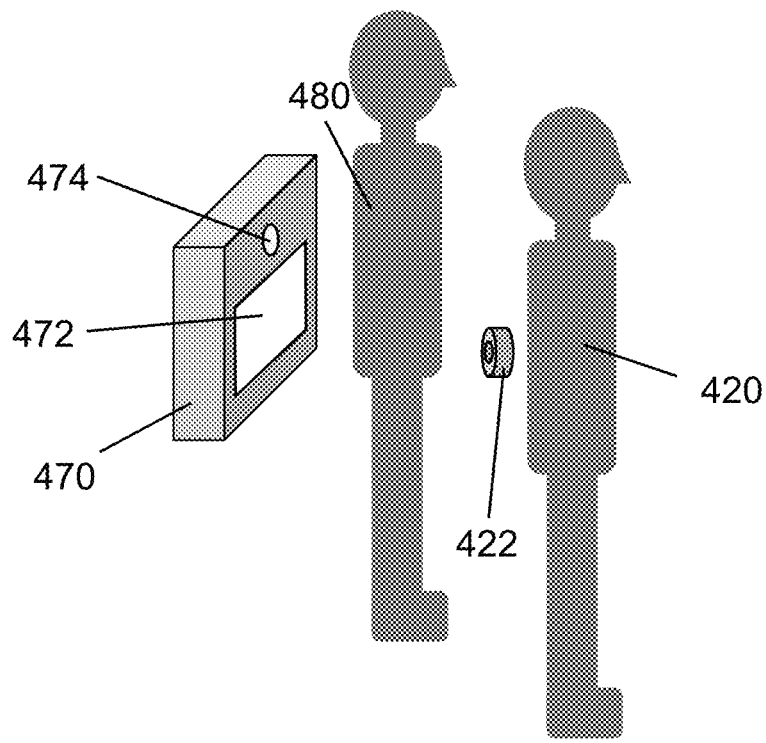
FIG. 23C is a diagram of a user using an electronic stethoscope with an interactive kiosk and measuring sounds on the user's back with a second user's assistance, according to aspects of the present embodiments.

FIG. 23C is a diagram of a user 420 using an electronic stethoscope 422 with an interactive kiosk 470 and measuring sounds on the user's back with assistance from a second user 480, according to aspects of the present embodiments. In some embodiments, the user 420 may be facing away from the interactive kiosk 470 while the second user 480 positions and moves the electronic stethoscope 422 and simultaneously observes a display screen 472 on the interactive kiosk 470 to obtain guidance and feedback on where to move the electronic stethoscope 422.

Figure 23D:
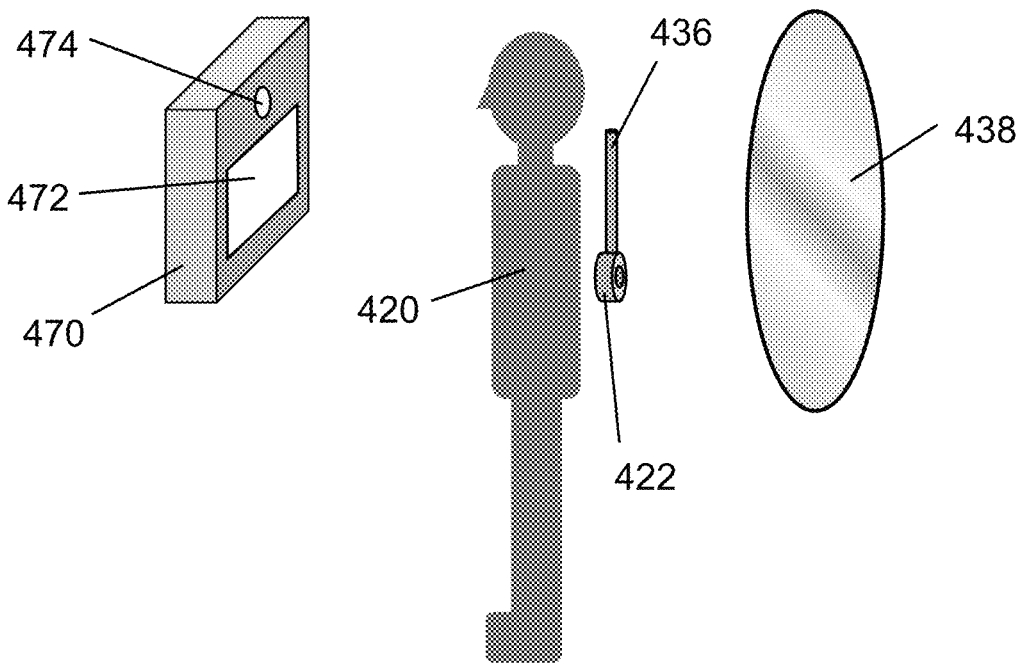
FIG. 23D is a diagram of a user using an electronic stethoscope with an interactive kiosk and measuring sounds on the user's back by using a rigid rod and a mirror, according to aspects of the present embodiments.

FIG. 23D is a diagram of a user 420 using an electronic stethoscope 422 with an interactive kiosk and measuring sounds on the user's back by using a rigid rod 436 connected to the stethoscope and a mirror 438 behind the user, according to aspects of the present embodiments. In some embodiments, the user 420 is holding the rigid rod 436 by hand. In other embodiments, there may also be a flexible strap attached to the electronic stethoscope to aid in its use by securing the electronic stethoscope around the user's torso, as illustrated in FIG. 6G. In some embodiments, a mirror 438 may be placed behind the user so that the user's back and the stethoscope 422 are reflected by the mirror 438 to be captured by the video camera 474 on the interactive kiosk 470.

Figure 24:
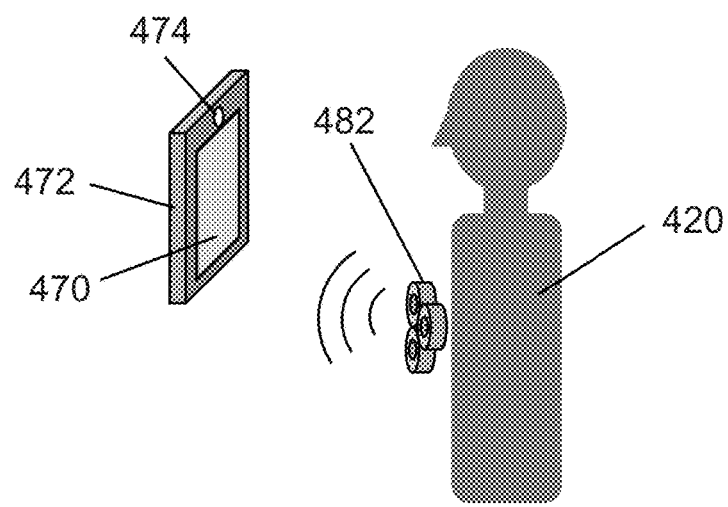
FIG. 24 is a diagram of a user using an electronic stethoscope with three connected bells, along with a mobile device, according to aspects of the present embodiments.
Figure 25A:
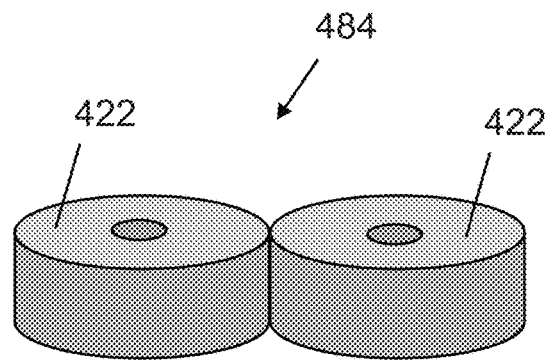
FIG. 25A is a diagram of an electronic stethoscope with two connected bells, according to aspects of the present embodiments.
Figure 25B:
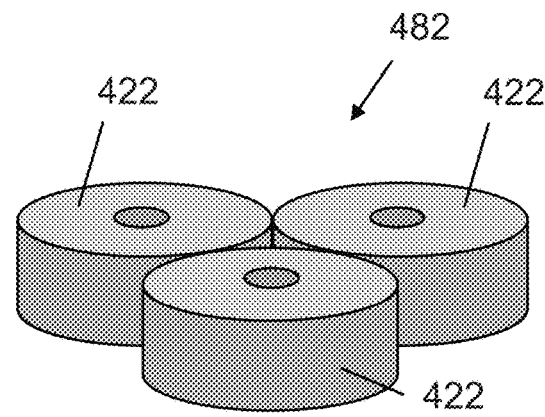
FIG. 25B is a diagram of an electronic stethoscope with three connected bells, according to aspects of the present embodiments.

FIG. 24 is a diagram of a user 420 using an electronic stethoscope 482 with three connected bells, along with a mobile device 472, according to aspects of the present embodiments. In some embodiments, the use of an electronic stethoscope 482 with more than one bell (each of which contains a microphone) may enable further localization of sounds by recording sounds at more than one location. In some embodiments, the multiple bells and multiple microphones may form an acoustic array. FIG. 25A is a diagram of an electronic stethoscope with two connected bells, according to aspects of the present embodiments. FIG. 25B is a diagram of an electronic stethoscope with three connected bells, according to aspects of the present embodiments.

Figure 10:
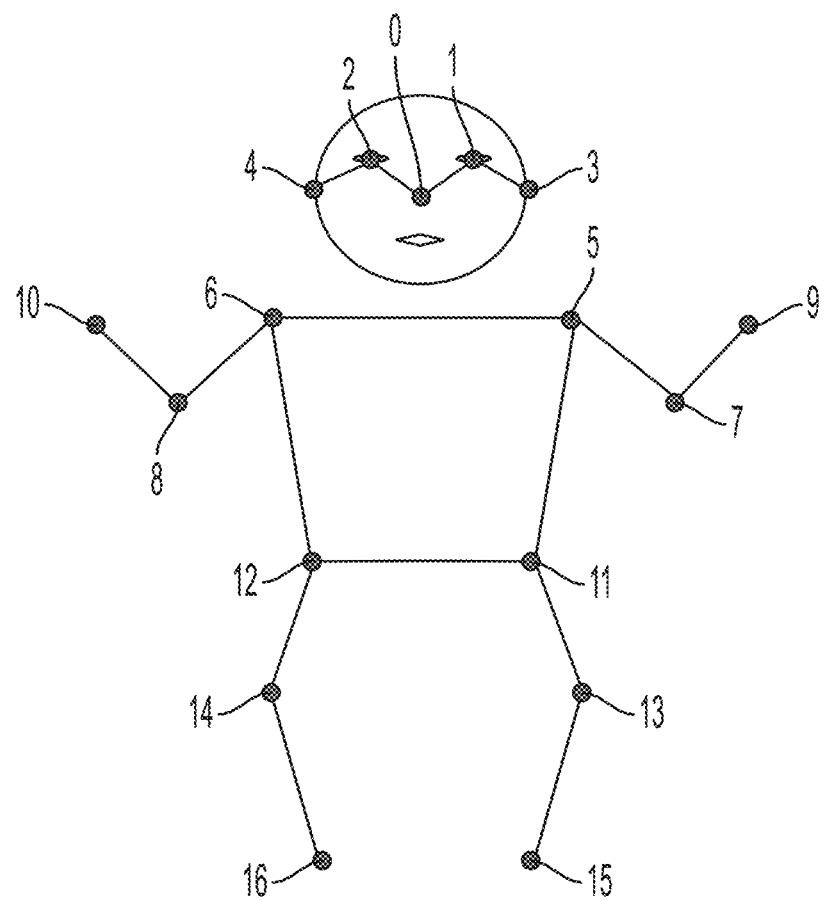
FIG. 10 is a diagram of key points located on a user's pose that may be identified using a visual algorithm.

Software and Algorithms
Visual Algorithms for Location and Position Identification FIG. 10 is a diagram of key points located on a user's pose that may be identified using a visual algorithm (https://www.skypack.dev/view/@tensorflow-models/pose-detection). The indicated key points occur at important joints or landmarks on a user's pose, and may include the ears, the eyes, the nose, the shoulders, the elbows, the hands, the hips, the knees, and the feet.

Figures 11A, 11B:
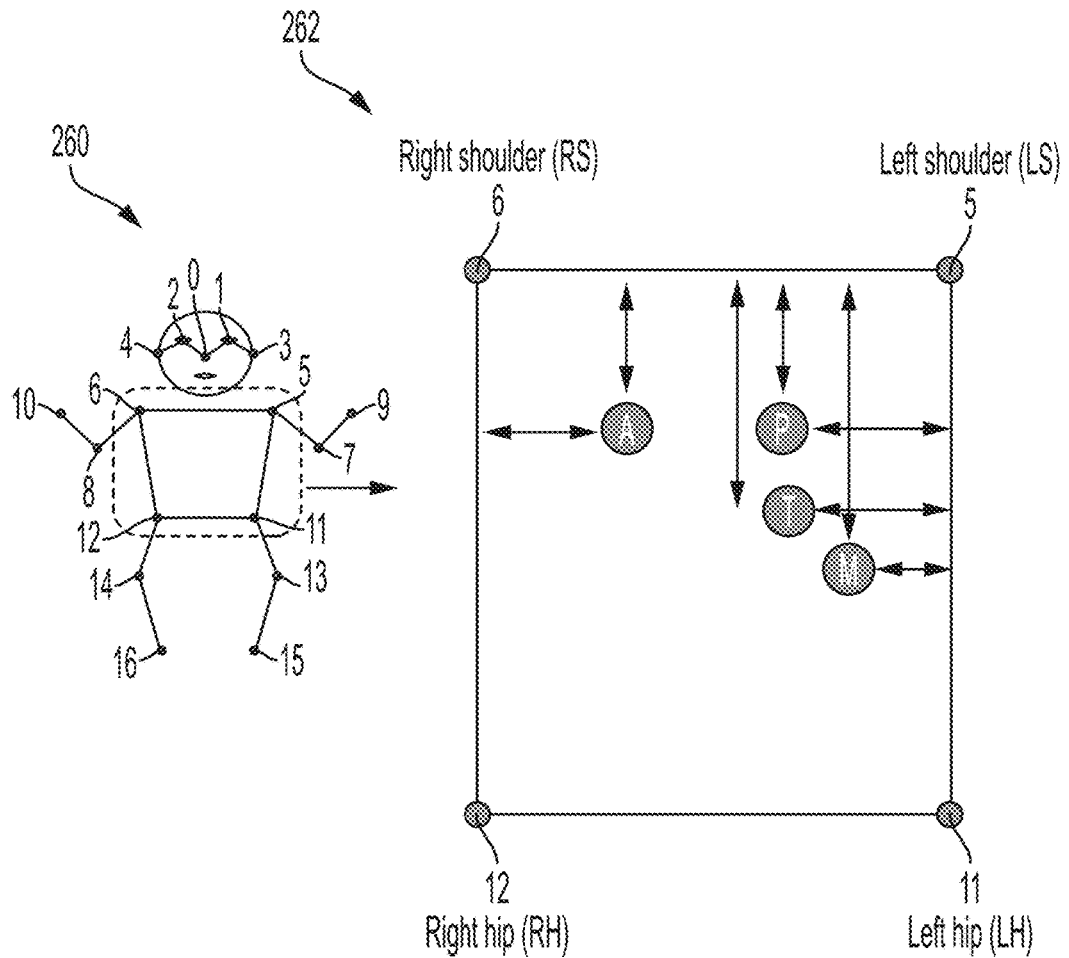
FIG. 11A is a diagram of four key points of a typical pose (i.e., right shoulder, left shoulder, right hip, and left hip) and four heart listening locations (i.e., atrial area, pulmonic area, tricuspid area, and mitral area). The four heart listening locations may be designated by relative distances from lines connecting between the key points, according to aspects of the present embodiments.
FIG. 11B is a table stating positions of the four heart listening locations. The vertical positions may be percentages of a shoulder-to-hip distance. Horizontal distances may be percentages of a shoulder-to-shoulder distance.

The smaller image at the left side of FIG. 11A shows the diagram from FIG. 10 with a rectangle indicating the main key points relevant for the torso (i.e., the shoulders and the hips). The larger image at the right side of FIG. 11A is a diagram of four key points of a typical pose relevant for the torso (i.e., right shoulder, left shoulder, right hip, and left hip) and four heart listening locations (i.e., atrial area, pulmonic area, tricuspid area, and mitral area). The four heart listening locations may be designated by relative distances (i.e., the double-ended arrows) from lines connecting between the key points (i.e. the straight lines between the circles representing the key points), according to aspects of the present embodiments.

FIG. 11B is a table stating positions of the four heart listening locations. In some embodiments, the vertical positions may be percentages of a shoulder-to-hip distance while horizontal distances may be percentages of a shoulder-to-shoulder distance. In some embodiments, the ranges of positions are related to variations in human bodies and users with varying personal body dimensions.

Figure 11C:
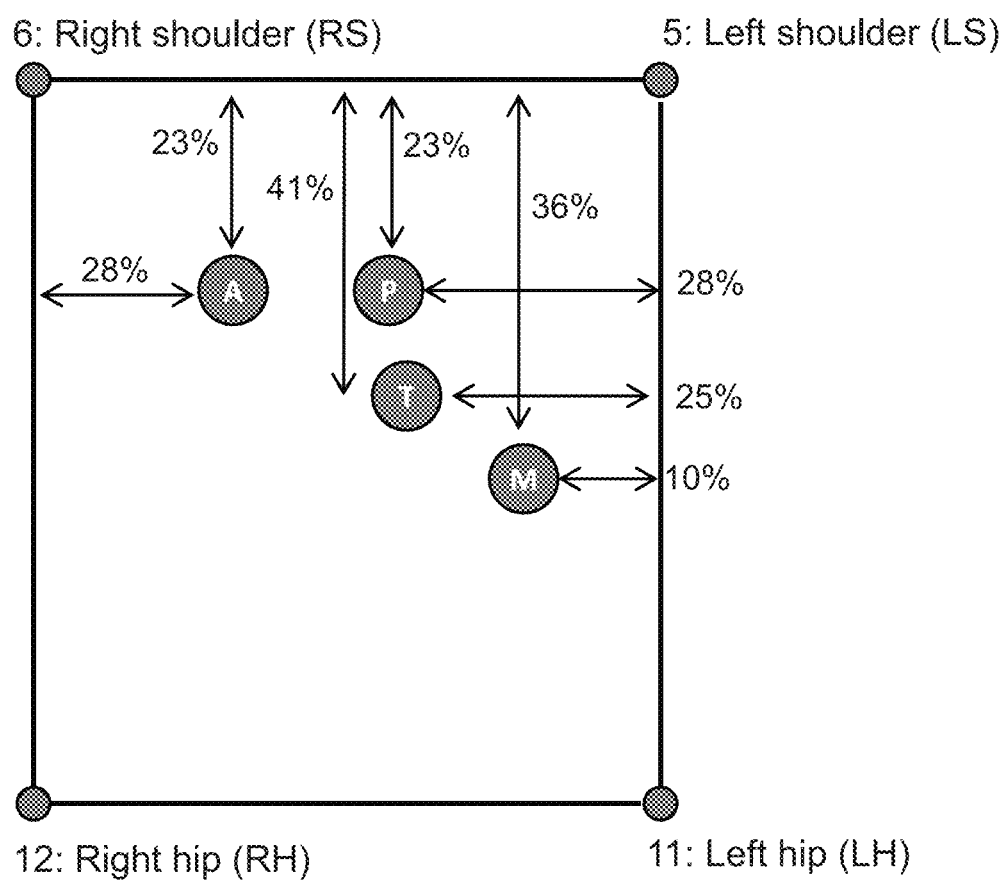
FIG. 11C is a diagram of example heart listening locations associated with heart valves relative to key points on a pose, according to aspects of the present embodiments.

FIG. 11C is a diagram of example heart listening locations associated with heart valves relative to key points on a pose, according to aspects of the present embodiments. These example locations have vertical and horizontal distances indicated that are specific distances within the given ranges in the table of FIG. 11B. In some embodiments, the key points being located by a visual localization algorithm with respect to a user's pose may provide flexibility of use and may not require advance knowledge of a specific user.

Figure 12:
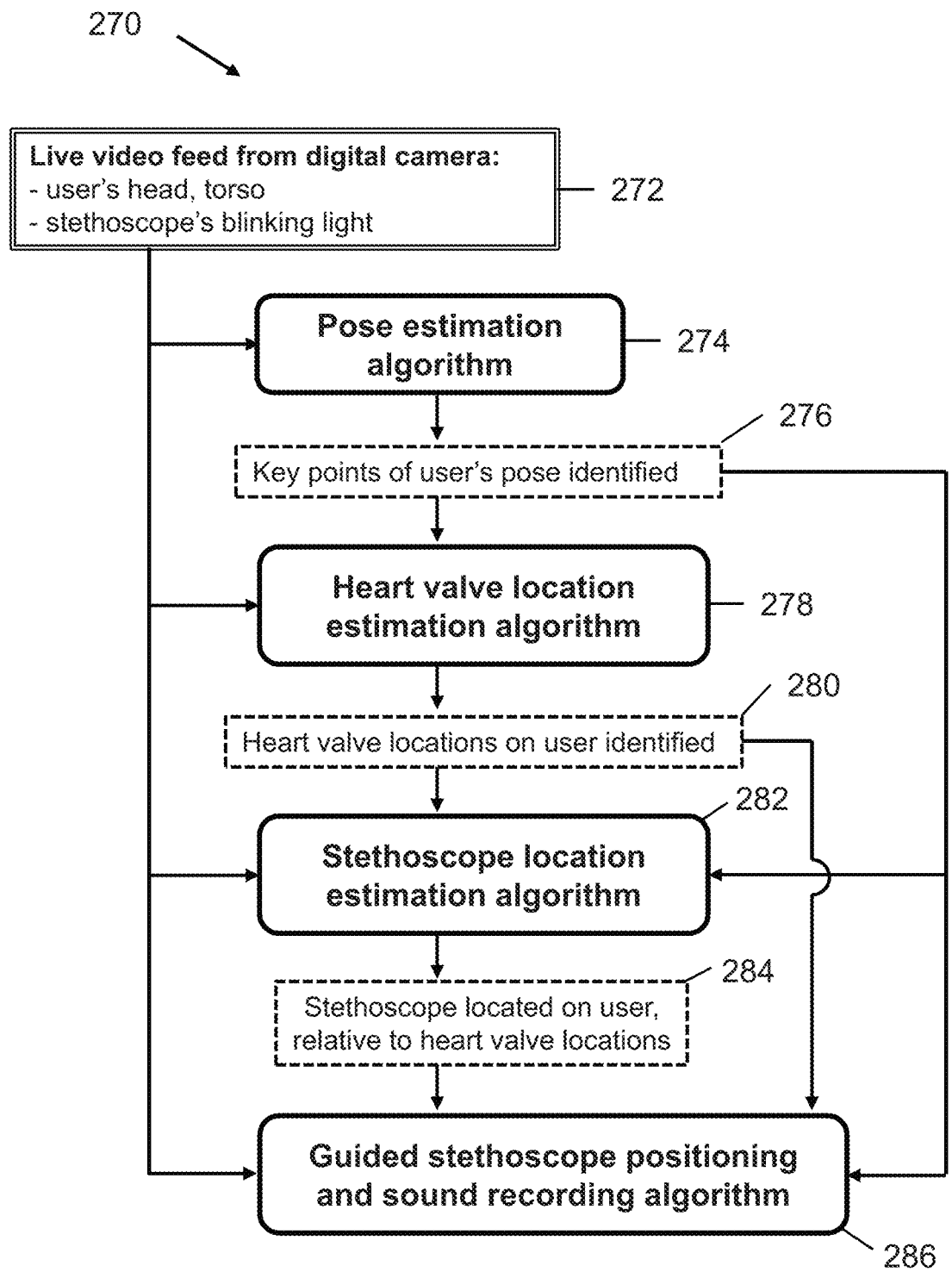
FIG. 12 is a flow chart describing a visual localization method providing a live video camera feed to multiple algorithms to locate key points on a user's pose, heart valve locations, and stethoscope location, according to aspects of the present embodiments.

FIG. 12 is a flow chart describing a visual localization method 270 providing a live video camera feed 272 to multiple algorithms to locate key points on a user's pose, heart valve locations, and stethoscope location, according to aspects of the present embodiments. In some embodiments, a live video feed 272 may be obtained from a digital camera that shows a user's head and torso and shows a blinking light on an electronic stethoscope. The live video feed may be provided to a plurality of algorithms including a pose estimation algorithm 274, a heart valve location estimation algorithm 278, a stethoscope location estimation algorithm 282, and a guided stethoscope positioning and sound recording algorithm 286. In some embodiments, the pose estimation algorithm 274 may output key points 276 of a user's pose, which are then provided to the heart valve location estimation algorithm 278. In some embodiments, heart valve locations 280 on the user may be identified by the heart valve location algorithm 278, and are then provided to the stethoscope location estimation algorithm 282. In some embodiments, the position of the stethoscope 284 found by the stethoscope location estimation algorithm 282 is provided to the guided stethoscope positioning and sound recording algorithm 286. In some embodiments, the guided stethoscope positioning and sound recording algorithm 286 may then guide the user to position the stethoscope at a plurality of heart valve listening locations where heart sounds may be recorded.

Figure 13:
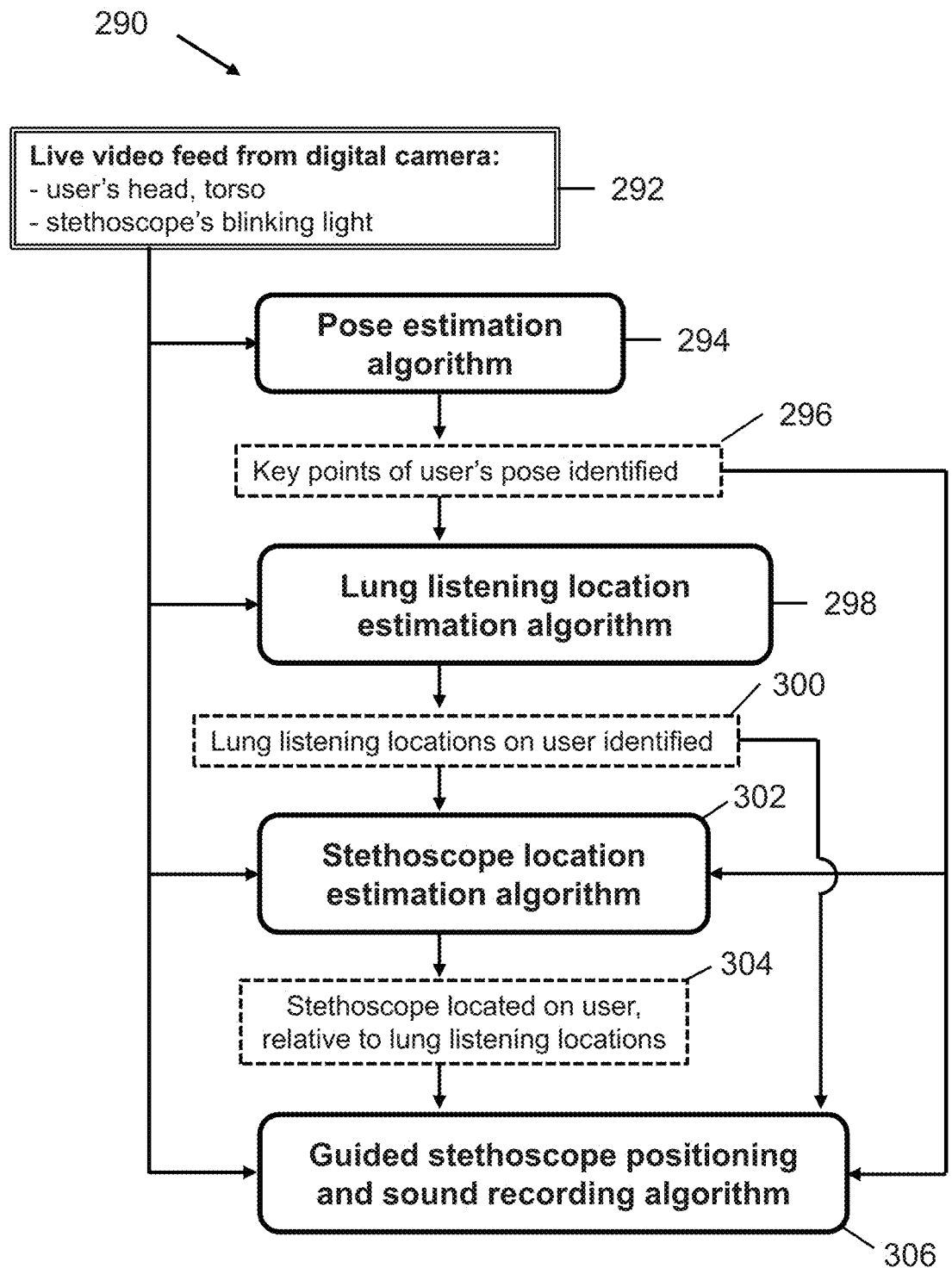
FIG. 13 is a flow chart describing a visual localization method providing a live video camera feed to multiple algorithms to locate key points on a user's pose, lung listening locations, and stethoscope location, according to aspects of the present embodiments.

FIG. 13 is a flow chart describing a visual localization method 290 providing a live video camera feed 292 to multiple algorithms to locate key points on a user's pose, lung listening locations, and stethoscope location, according to aspects of the present embodiments. In some embodiments, a live video feed 292 may be obtained from a digital camera that shows a user's head and torso and shows a blinking light on an electronic stethoscope. The live video feed 292 may be provided to a plurality of algorithms including a pose estimation algorithm 294, a lung listening location estimation algorithm 298, a stethoscope location estimation algorithm 302, and a guided stethoscope positioning and sound recording algorithm 306. In some embodiments, the pose estimation algorithm 294 may output key points 296 of a user's pose, which are then provided to the lung listening location estimation algorithm 298. In some embodiments, lung listening locations 300 on the user may be identified by the lung listening location algorithm 298, and are then provided to the stethoscope location estimation algorithm 302. In some embodiments, the position of the stethoscope 304 found by the stethoscope location estimation algorithm 302 may be provided to the guided stethoscope positioning and sound recording algorithm 306. In some embodiments, the guided stethoscope positioning and sound recording algorithm 306 may then guide the user to position the stethoscope at a plurality of lung listening locations where lung sounds may be recorded.

Audio Algorithms for Sound Classification

A machine learning audio classification algorithm is trained using audio datasets including various heart sounds corresponding to healthy hearts and hearts with one or more known health conditions, and various non-heart sounds. The heart sound dataset may include normal heartbeats at different speeds originating from patients of different demographics (e.g., ages, sexes, activity levels, general health levels, etc.). The heart sound dataset may also include sounds corresponding to heart conditions including aortic valve stenosis, mitral valve regurgitation, aortic valve regurgitation, mitral valve stenosis, patent ductus arteriosus, pulmonary valve stenosis, tricuspid valve regurgitation, and hypertrophic obstructive cardiomyopathy. The non-heart sound dataset may include speech, vehicle traffic, dogs barking, children crying, noise, and music.

Figure 17:
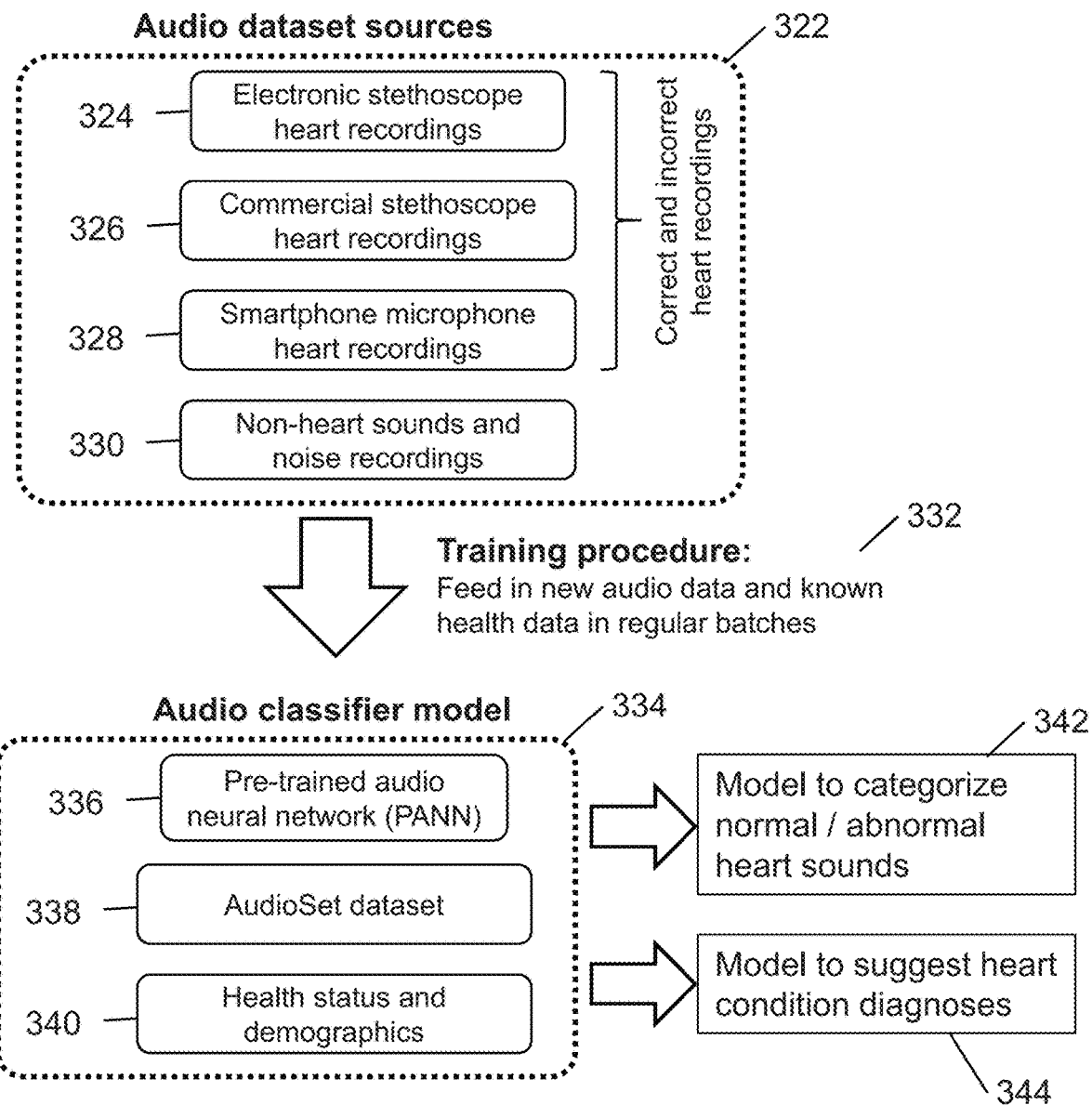
FIG. 17 is a flow chart describing a method to train an audio classifier model with heart sounds, according to aspects of the present embodiments.

FIG. 17 is a flow chart describing a method 320 to train an audio classifier model with heart sounds, according to aspects of the present embodiments. In this method 320, several types of audio datasets 322 from different sources may be provided to an audio classifier model 334. In some embodiments, the audio dataset sources 322 may include electronic stethoscope heart recordings 324, commercial stethoscope heart recordings 326, smartphone microphone heart recordings 328, and non-heart sounds and noise recordings 330. The heart sound recordings (324, 326, 328) may include both correct and incorrect heart sound recordings, corresponding to recordings made from correctly and incorrectly positioned stethoscopes, respectively. The incorrect heart sound recordings may include recordings made by stethoscopes placed at a different part of the body or over clothing. The correct heart sound recordings may also include sounds from patients whose heart conditions have been confirmed by state of the art methods (e.g., electrocardiogram).

Referring still to FIG. 17, in some embodiments, the training procedure 332 to train the audio classifier model may include feeding in new audio data and known health data in regular batches to the audio classifier model 334, e.g., every few days. In some embodiments, the audio classifier model may include a pre-trained audio neural network (PANN) 336, a dataset of known sound recordings such as the AudioSet dataset 338, and health status, family history, and demographic information 340. In some embodiments, the results of the training of the audio classifier may include a trained model to categorize whether a heart sound is normal or abnormal 342, and a trained model to suggest heart condition diagnoses 344.

Figure 18:
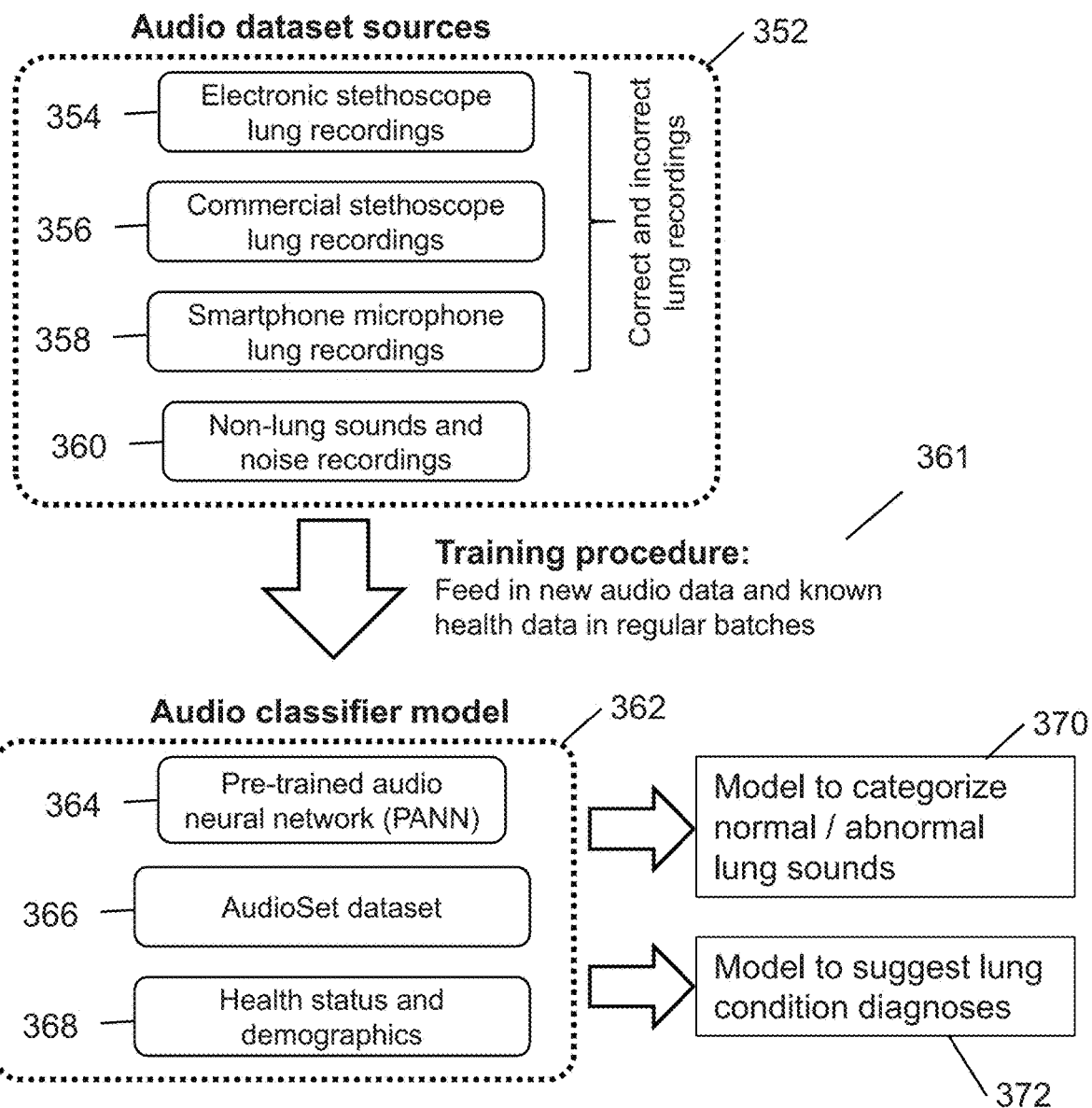
FIG. 18 is a flow chart describing a method to train an audio classifier model with lung sounds, according to aspects of the present embodiments.

FIG. 18 is a flow chart describing a method 350 to train an audio classifier model 362 with lung sounds, according to aspects of the present embodiments. In this method, several types of audio datasets 352 from different sources are provided to an audio classifier model 362. In some embodiments, the audio dataset sources 352 may include electronic stethoscope lung recordings 354, commercial stethoscope lung recordings 356, smartphone microphone lung recordings 358, and non-lung sounds and noise recordings 360. The lung sound recordings (354, 356, 358) may include both correct and incorrect lung sound recordings corresponding to recordings made from correctly and incorrectly positioned stethoscopes, respectively. In some embodiments, a generative adversarial network (GAN) may also be used to train the audio classifier model using sound recordings from incorrect positioning so that the model may learn what sounds may be correct or incorrect.

Referring still to FIG. 18, in some embodiments, the training procedure 361 to train the audio classifier model may include feeding in new audio data and known health data in regular batches to the audio classifier model 362 every few days. In some embodiments, the audio classifier model 362 may include a pre-trained audio neural network (PANN) 364, a dataset of known sound recordings such as the AudioSet dataset 366, and health status and demographic information 368. In some embodiments, the results of the training of the audio classifier may be a model to categorize whether a lung sound is normal or abnormal 370, and a model to suggest lung condition diagnoses 372.

Figure 19:
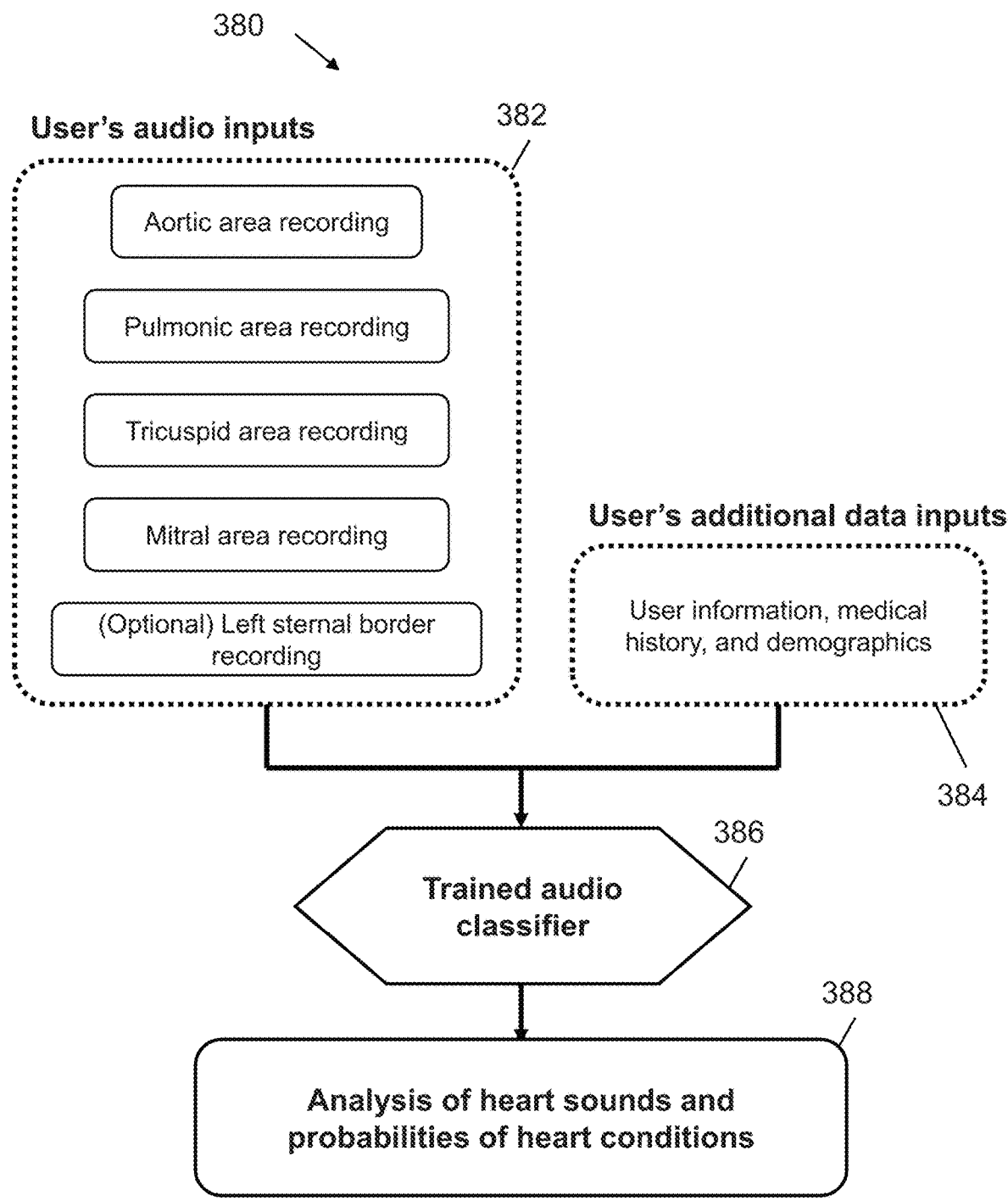
FIG. 19 is a flow chart describing a method to classify a user's heart sound recordings using a trained audio classifier model to diagnose heart conditions, according to aspects of the present embodiments.

FIG. 19 is a flow chart describing a method 380 to classify a user's heart sound recordings using a trained audio classifier model to diagnose heart conditions, according to aspects of the present embodiments. In this method 380, audio inputs 382 that may include heart sounds recorded from a plurality of locations and additional data inputs 384 may be provided to a trained audio classifier algorithm 386. In some embodiments, the heart sound recordings 382 may include recordings acquired from an aortic valve area, a pulmonic valve rea, a tricuspid valve area, a mitral valve area, and optionally a left sternal border area. In some embodiments, the additional data inputs 384 may include information provided by the user regarding the user's own personal user information including personal identification information, medical history, demographics, height, weight, medications, allergies, etc. In some embodiments, the additional data inputs 384 may help with heart condition classification, or they may be used for the storage and/or transmission of heart sound recordings and diagnoses. In some embodiments, the analysis of heart sounds is conducted and probabilities of heart conditions 388 are output, with the classified heart condition with the highest calculated probability being used as the primary prediction (see FIG. 16 for example of probabilities in the output).

Figure 20:
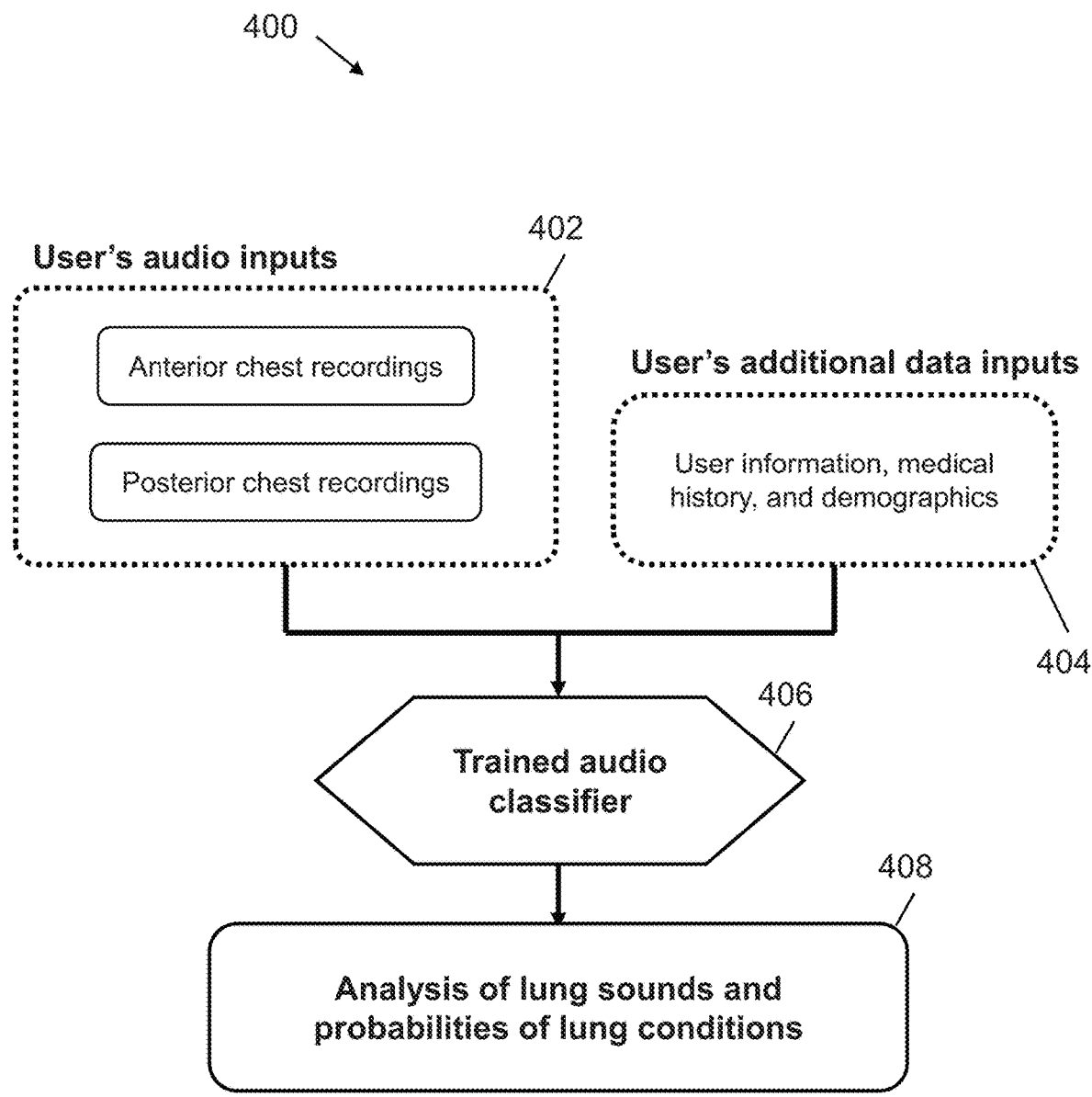
FIG. 20 is a flow chart describing a method to classify a user's chest sound recordings using a trained audio classifier model to diagnose lung conditions, according to aspects of the present embodiments.

FIG. 20 is a flow chart describing a method 400 to classify a user's chest sound recordings using a trained audio classifier model to diagnose lung conditions, according to aspects of the present embodiments. In this method 400, audio inputs 402 that may include lung sounds recorded from a plurality of locations and additional data inputs 404 may be provided to a trained audio classifier algorithm 386. In some embodiments, the lung sound recordings 402 may include recordings acquired from the front (anterior) chest and from the back (posterior) chest of the user. In some embodiments, the additional data inputs 404 may include information provided by the user regarding the user's own personal user information including personal identification information, medical history, demographics, height, weight, medications, allergies, etc. In some embodiments, the additional data inputs 404 may help with lung condition classification, or they may be used for the storage and/or transmission of lung sound recordings and diagnoses. In some embodiments, the analysis of lung sounds is conducted and probabilities of lung conditions 408 are output, with the classified lung condition with the highest calculated probability being used as the primary prediction.

Software Interface for User Interactions

FIGS. 14A-14E are views of an example software interface guiding a user to position a stethoscope to measure heart sounds, according to aspects of the present embodiments. These images correspond to an implementation of the disclosures where a laptop computer with a built-in webcam is used along with a browser running on the laptop computer, and where the laptop computer connects via an internet connection to an external server where the visual localization algorithm and audio classifier algorithm are running.

Figure 14A:
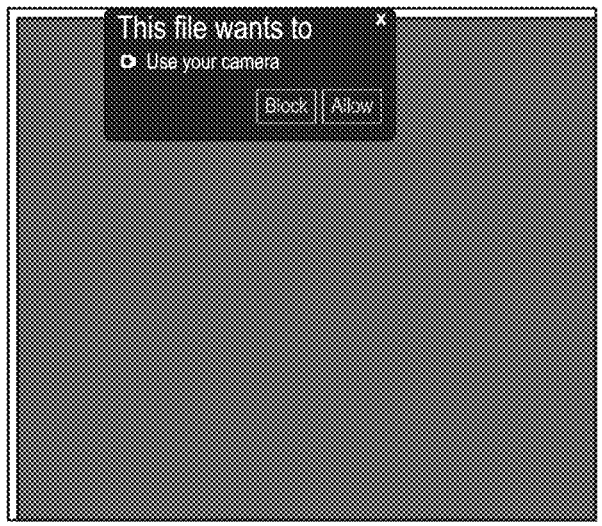
FIG. 14A is a view of an example software interface guiding a user to position a stethoscope to measure heart sounds, according to aspects of the present embodiments.
Figure 14B:
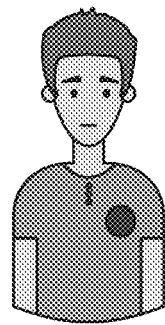
FIG. 14B is a view of an example software interface guiding a user to position a stethoscope to measure heart sounds, according to aspects of the present embodiments.

In FIG. 14A, the user allows the browser to access the built-in webcam by granting access by clicking on a specified button. In FIG. 14B, a schematic illustration shows a representation of a video image of the user. The red circle is overlaid over the user image to show where to place the stethoscope. In some embodiments, the software interface may also include visual indications, such as an outline or a plurality of markers, overlaid on top of the live video image that may be shown to the user, to help guide the user to be positioned in a location and orientation on screen for optimal pose estimation by a visual algorithm.

Figure 14C:
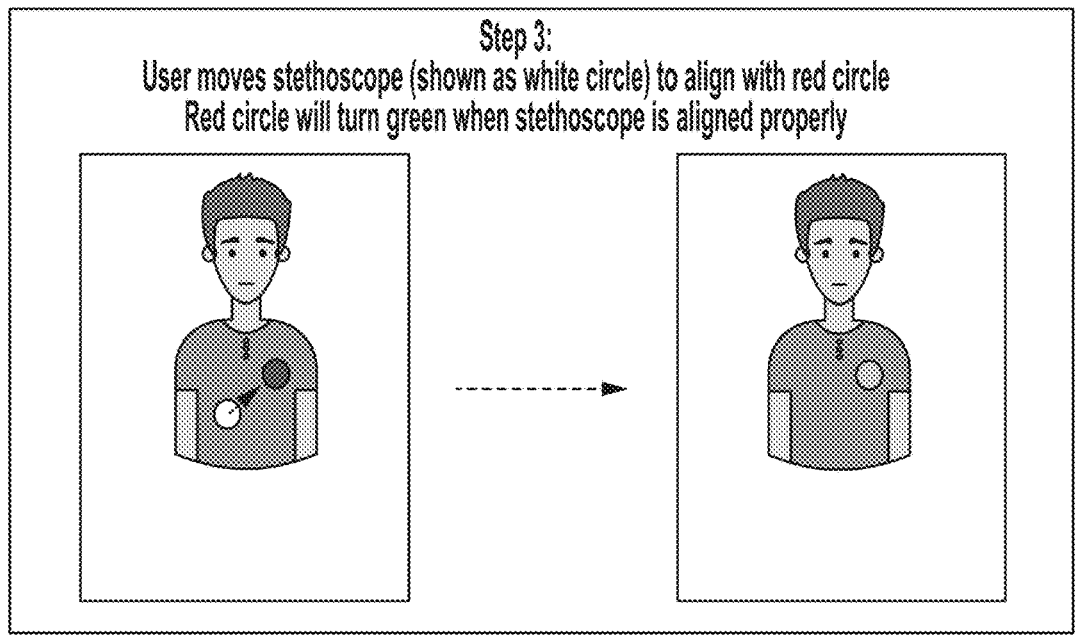
FIG. 14C is a view of an example software interface guiding a user to position a stethoscope to measure heart sounds, according to aspects of the present embodiments.
Figure 14D:
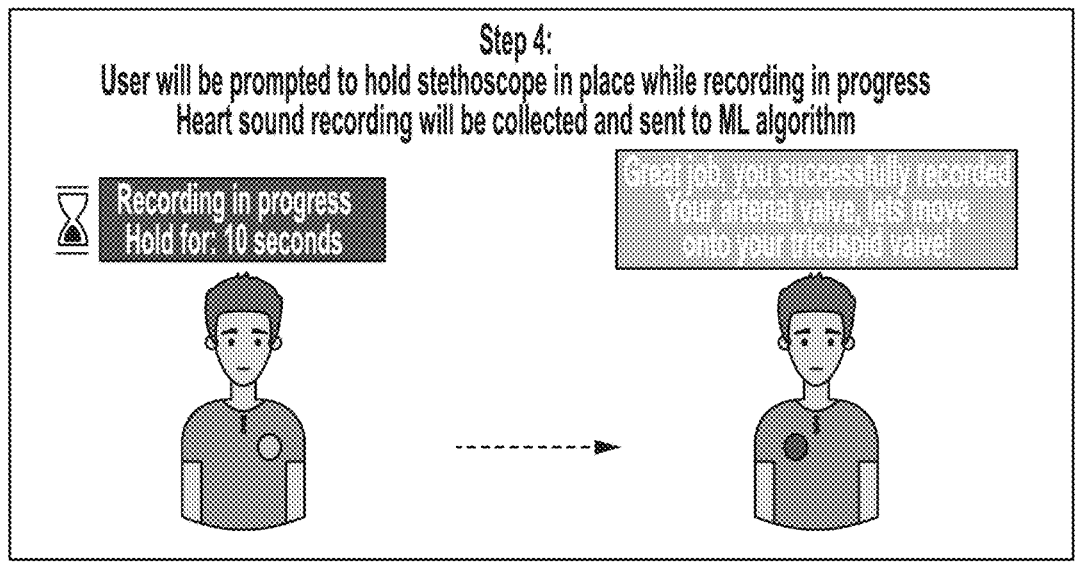
FIG. 14D is a view of an example software interface guiding a user to position a stethoscope to measure heart sounds, according to aspects of the present embodiments.
Figure 14E:
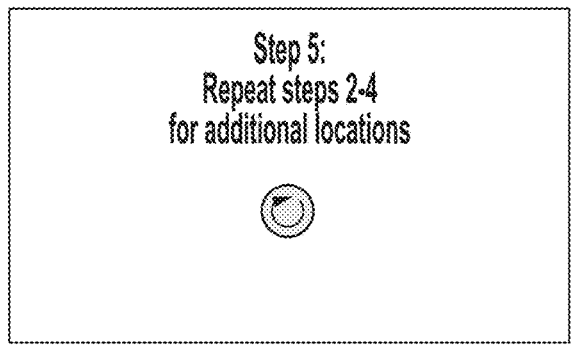
FIG. 14E is a view of an example software interface guiding a user to position a stethoscope to measure heart sounds, according to aspects of the present embodiments.

In FIG. 14C, the images illustrate the user moving the stethoscope from a starting location indicated by a white circle, to the indicated target location indicated by a red circle, and the indicator turning into a green circle when the stethoscope is successfully placed at the indicated target location. In FIG. 14D, the software program prompts the user to hold the stethoscope in place while a heart sound recording is collected. The software program shows when the recording is in progress, the duration of the sound recording, and a message indicating successful measurement of sounds at a particular heart valve listening location (for example, the tricuspid valve, as shown in the image). In FIG. 14E, the program indicates that the previous steps illustrated in FIGS. 14B-14D will be repeated for additional locations (i.e., for additional heart valve listening locations). In some embodiments, the graphical indications described above (i.e., white circle, red circle, and green circle) may be other shapes and/or colors, but may be visually distinct from each other so that they may clearly indicate the different positions and/or conditions. Stated otherwise, moving the stethoscope, by the user, causes the processer of the computer or electronic device on which the software interface is installed to execute programming thereby causing the graphical interface to render changes in visual indicators to signal to the user that the stethoscope is properly positioned.

Figure 15A:
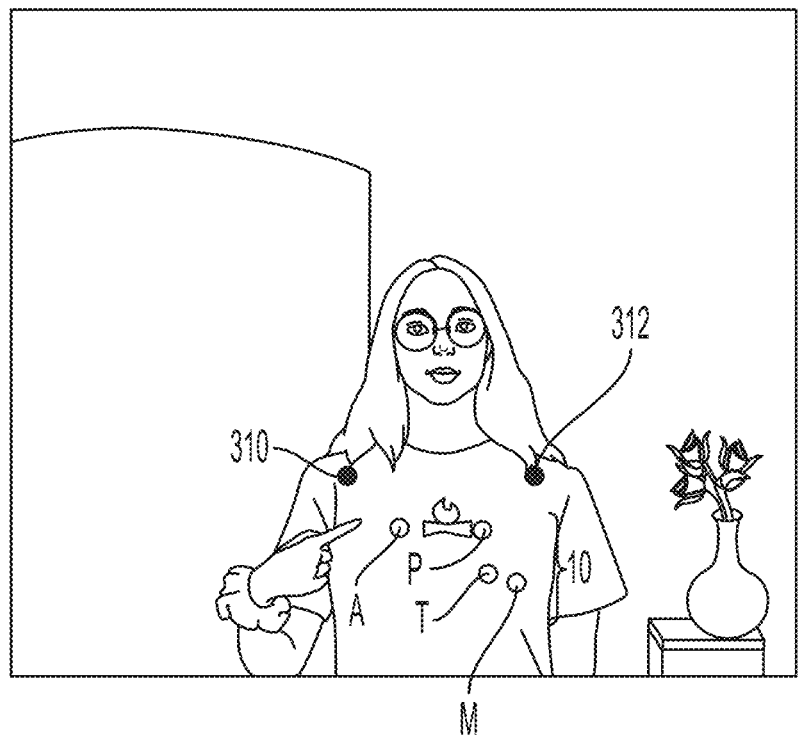
FIG. 15A is a screenshot from an example software interface showing a digital image of a user with key points at shoulders (i.e., dark circles superimposed on image) located by a visual localization algorithm and heart valve locations (i.e. white circles superimposed on image) located by another visual localization algorithm, according to aspects of the present embodiments.
Figure 15B:
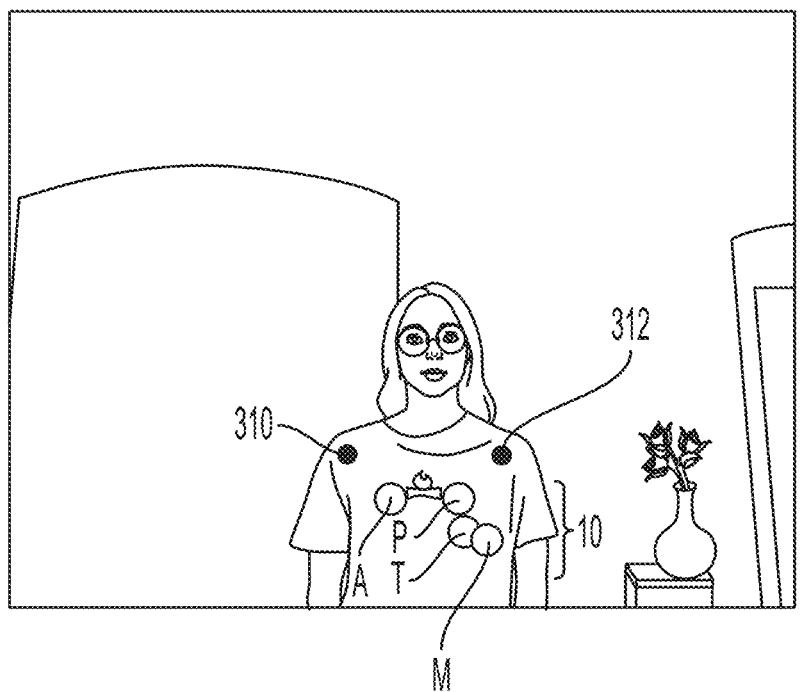
FIG. 15B is a screenshot from an example software interface showing a digital image of a user with key points at shoulders (i.e., dark circles superimposed on image) located by a visual localization algorithm and heart valve locations (i.e. white circles superimposed on image) located by another visual localization algorithm, according to aspects of the present embodiments.

FIGS. 15A and 15B are screenshots from an example software interface showing a digital image of a user with key points at shoulders (i.e., dark red circles superimposed on image) located by a visual localization algorithm and heart valve locations (i.e., white circles superimposed on image) located by another visual localization algorithm, according to aspects of the present embodiments. In some embodiments, the heart valve locations may be indicated by markers of different shapes and colors. In some embodiments, the heart valve locations may be indicated by markers that include a letter or symbol to represent the particular heart valve location (for example, "A" for atrial valve, "P" for pneumonic valve, "T" for tricuspid valve, and "M" for mitral valve). The screenshots of FIGS. 15A and 15B were generated by the software following the general procedures described in the detailed description of FIG. 12.

Figure 16:
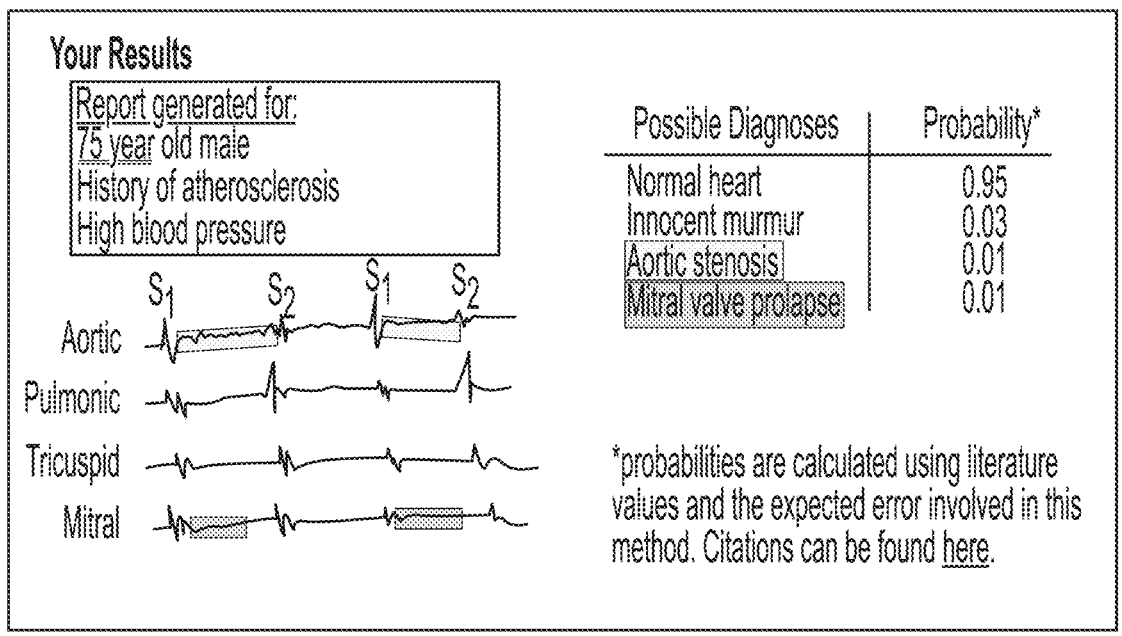
FIG. 16 is an example of software interface output showing a user's results and possible heart condition diagnoses, according to aspects of the present embodiments.

FIG. 16 is an example of software interface output showing a user's results and possible heart condition diagnoses, according to aspects of the present embodiments. In some embodiments, the output shows basic demographic information for the user, waveforms of the sound recordings made at each of the heart listening locations. In some embodiments, the output show possible diagnoses (e.g., different heart murmurs or other conditions), and calculated probabilities for the likelihoods of each diagnosis. In some embodiments, the output may show corresponding waveforms for healthy heart sounds and other information regarding the heart as educational information for the user.

Relationship Between Hardware, Inputs, Outputs, Interfaces, and Algorithms

Figure 26:
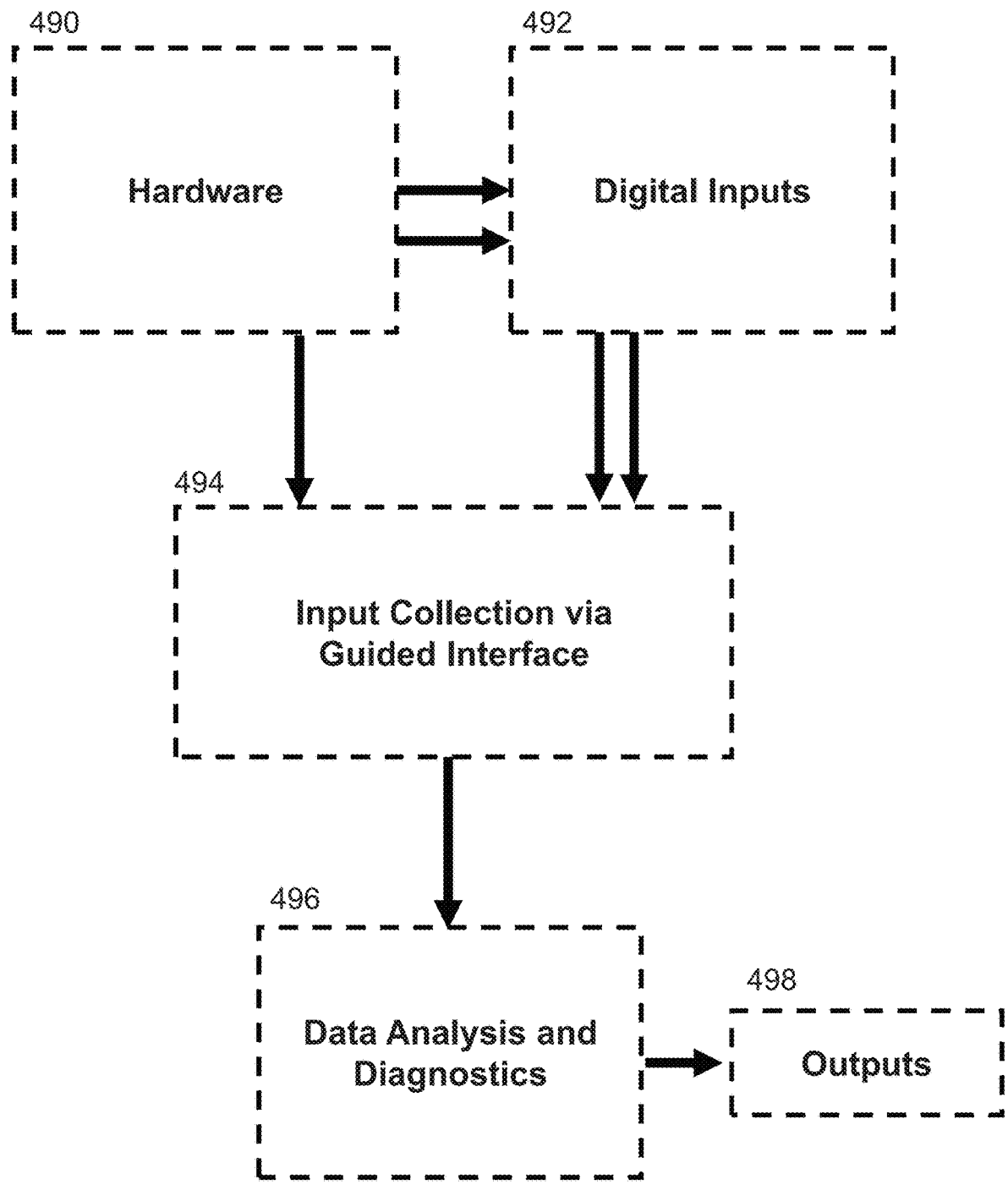
FIG. 26 is a flow chart describing relationships for an electronic stethoscope measurement and analysis system between various aspects of hardware, software, inputs, outputs, and signals, according to aspects of the present embodiments.

FIG. 26 is a flow chart describing relationships for an electronic stethoscope measurement and analysis system between various aspects of hardware, software, inputs, outputs, and signals, according to aspects of the present embodiments. In some embodiments, hardware components 490 may provide various signals to digital inputs 492 and input collection via guided interface 494. In some embodiments, digital inputs 492 also may provide signals to input collection via guided interface 494. In some embodiments, the input collection via guided interface 494 then may output data for data analysis and diagnostics 496, which finally may generate outputs 498. Further details of the parts of FIG. 26 are described in more detail in FIGS. 27A-27D.

Figure 27A:
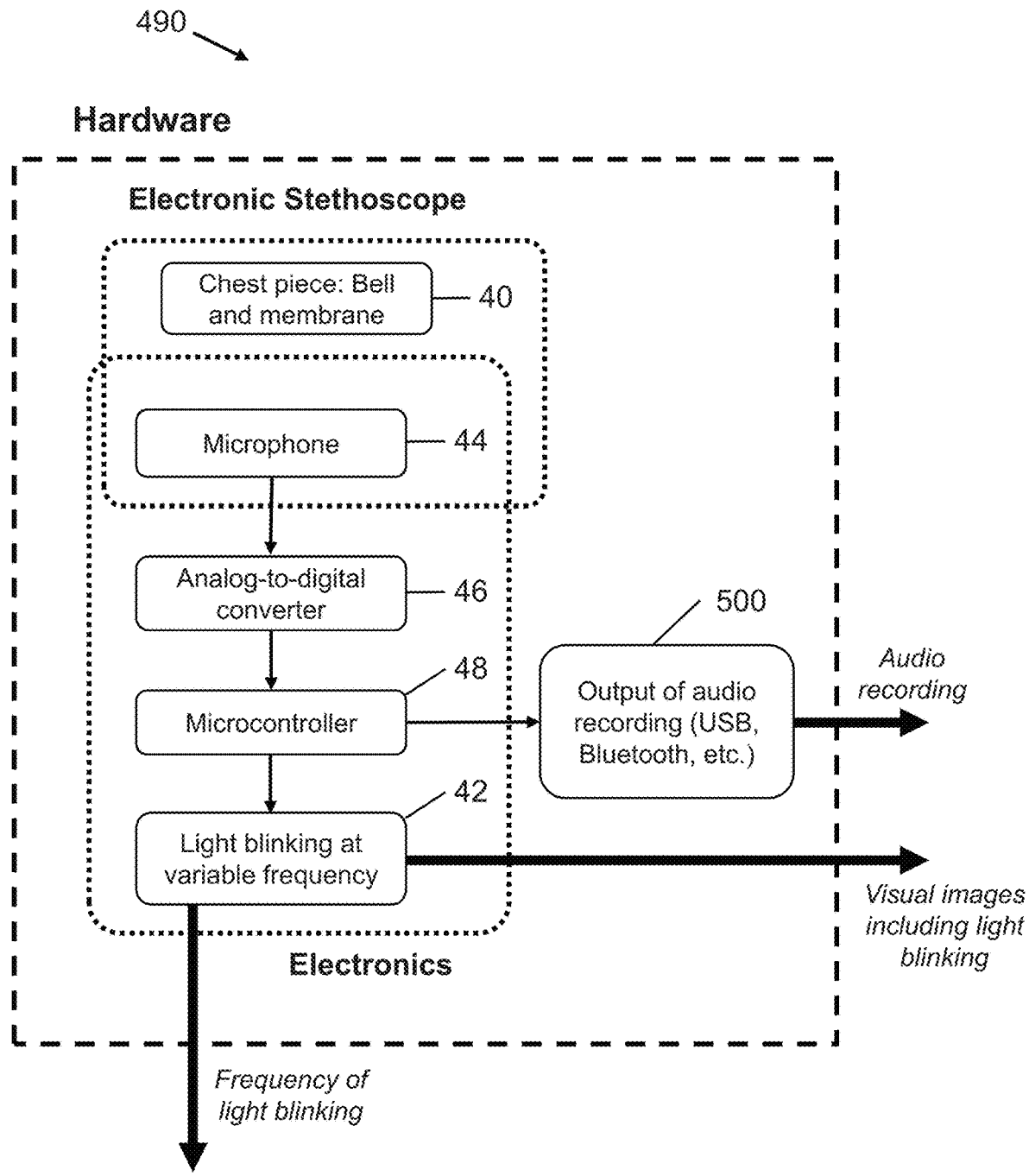
FIG. 27A is a flow chart showing details of hardware for the flow chart of FIG. 26, according to aspects of the present embodiments.

FIG. 27A is a flow chart showing details of hardware 490 for the flow chart of FIG. 26, according to aspects of the present embodiments. In some embodiments, the hardware may include an electronic stethoscope, which may include a chest piece 40 (which includes a bell and membrane), and microphone 44. In some embodiments, the electronics may include the microphone 44, an analog-to-digital converter (ADC) 46, a microcontroller 48, and a light or light-emitting device 42 that may blink at a variable frequency or in a controllable pattern. In some embodiments, the microphone 44 may record sounds that are converted to a digital signal by the ADC 46 which is then transmitted by the microcontroller 48 to an output signal 500. In some embodiments, the blinking of the light 42 may be controlled by the microcontroller 48, and the program of blinking may be transmitted to the input collection via guided interface 494. In some embodiments, the visual of the blinking light and where it is located with respect to the user's body pose may also be recorded.

Figure 27B:
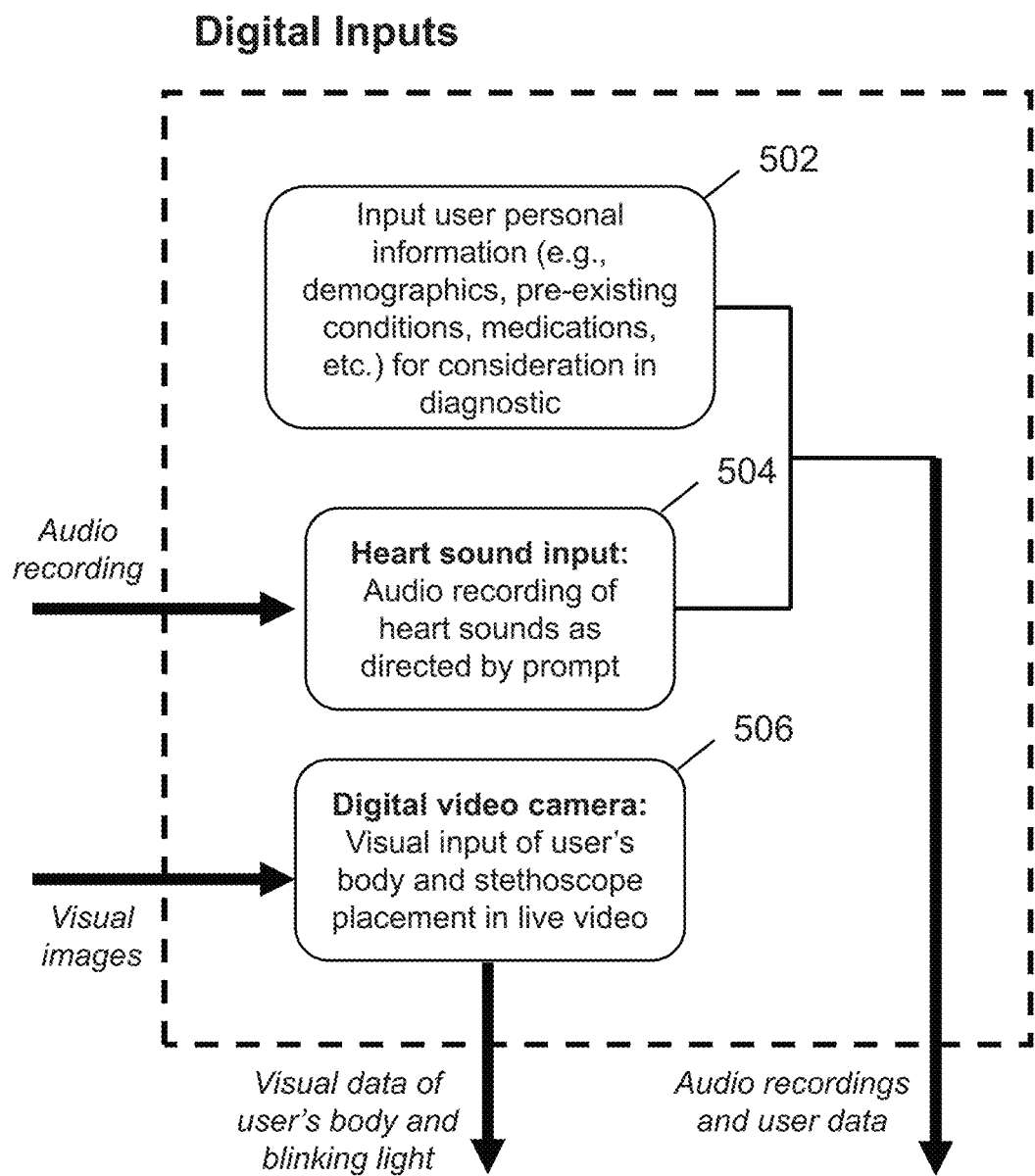
FIG. 27B is a flow chart showing details of digital inputs for the flow chart of FIG. 26, according to aspects of the present embodiments.

FIG. 27B is a flow chart showing details of digital inputs 492 for the flow chart of FIG. 26, according to aspects of the present embodiments. In some embodiments, the digital inputs may include user personal information 502, heart sound input 504 and a live video feed from a digital video camera 506 with visual input of the user's body and placement of the stethoscope. In some embodiments, these digital inputs may be then transmitted to the input collection via guided interface.

Figure 27C:
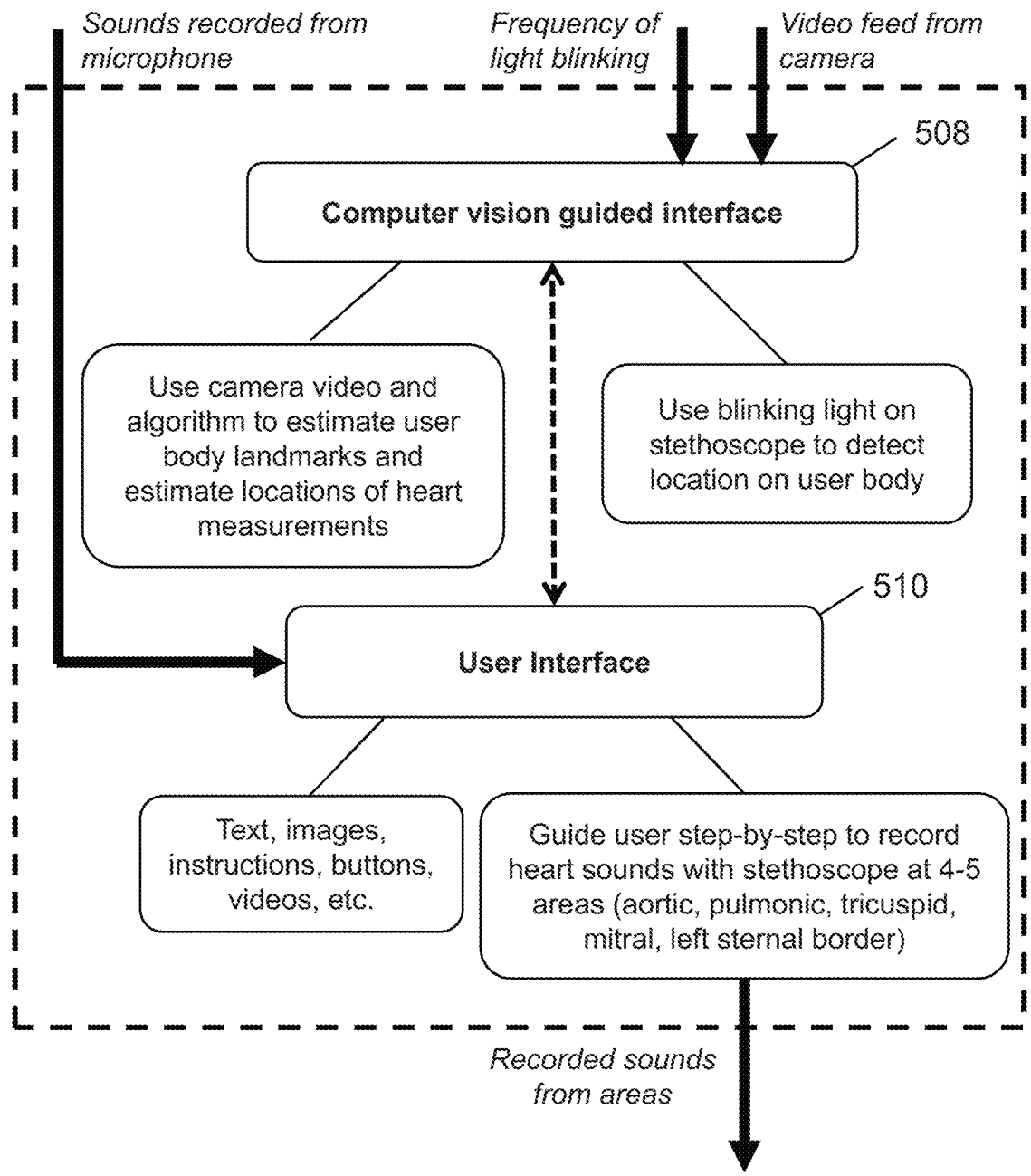
FIG. 27C is a flow chart showing details of input collection guided interface for the flow chart of FIG. 26, according to aspects of the present embodiments.

FIG. 27C is a flow chart showing details of input collection via guided interface 494 for the flow chart of FIG. 26, according to aspects of the present embodiments. In some embodiments, the frequency of light blinking (or other pattern of blinking of the light-emitting device) and the live video feed from the camera may be provided to a computer vision guided interface 508, which may use an algorithm to estimate user body landmarks (i.e., the key points on a pose) to identify heart listening locations, and may use the blinking light on the stethoscope to detect the location of the stethoscope relative to the user's body position. In some embodiments, sounds recorded from the microphone may be provided to the user interface 510, which interacts with the computer vision guided interface 508 to guide the user to record heart sounds at 4 or 5 target heart listening locations. In some embodiments, the user interface may use a combination of text, images, instructions, buttons, videos, etc., to provide information to the user and to obtain inputs and instructions from the user. In some embodiments, the recorded heart sounds at the target heart listening locations are provided to the data analysis and diagnostics and/or the outputs.

Figure 27D:
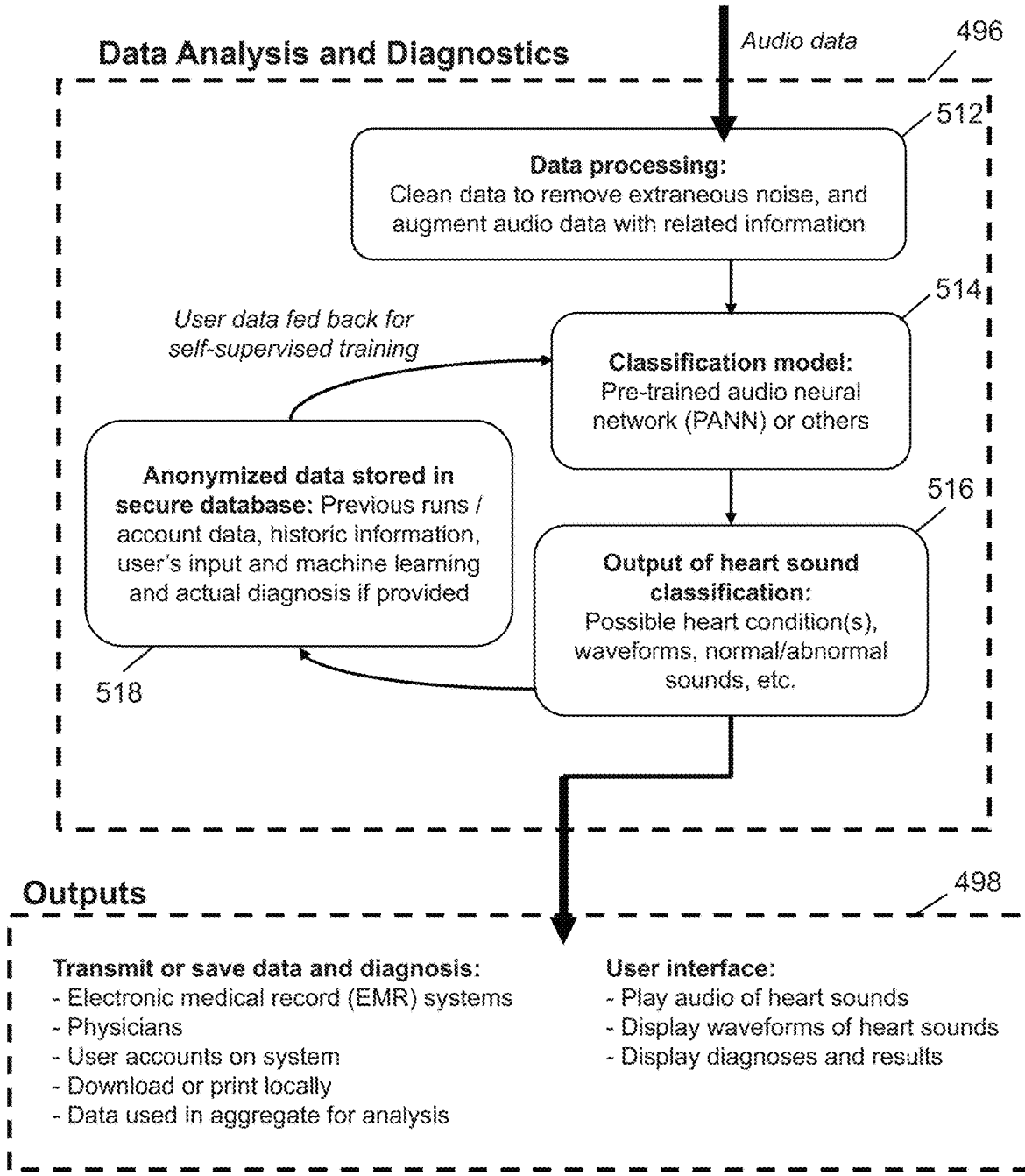
FIG. 27D is a flow chart showing details of data analysis and diagnostic and of outputs for the flow chart of FIG. 26, according to aspects of the present embodiments.

FIG. 27D is a flow chart showing details of data analysis and diagnostic 496 and of outputs 498 for the flow chart of FIG. 26, according to aspects of the present embodiments. In some embodiments, audio data may be provided to data processing 512, which may clean the data to remove extraneous noise and augment the audio data with related information (e.g., user personal data, health status, etc.). In some embodiments, the processed audio data may be provided to the audio classification model 514, which may include a pre-trained audio neural network (PANN) or other algorithms. In some embodiments, the outputs 516 of the heart sound classification may include possible heart condition(s) with probabilities of occurrence, waveforms of the analyzed heart sound recordings, normal and abnormal sounds, etc. In some embodiments, the outputs may be stored as anonymized data in a secure database 518, which may also include previous runs or account data, historic information, inputs from the user and machine learning, and actual diagnosis from a third party medical practitioner if chosen to be provided by the user.

Referring still to FIG. 27D, the outputs 498 may include options to transmit or save the data and diagnosis, and to communicate results to the user via a user interface. In some embodiments, saving or transmitting the data may include transmitting the data to an electronic medical record (EMR) system, transmitting the data to a physician, saving the data to a user account on a local electronic device or on an external server, downloading or printing the data locally, and/or using the data in aggregate for further analysis and comparison across multiple users. In some embodiments, the user interface may play audio of the recorded heart sounds, display waveforms of the heart sounds, and display diagnoses and results. In some embodiments, the user interface may also play audio of normal heart sounds for comparison, and may display waveforms of normal heart sounds.

Figure 28:
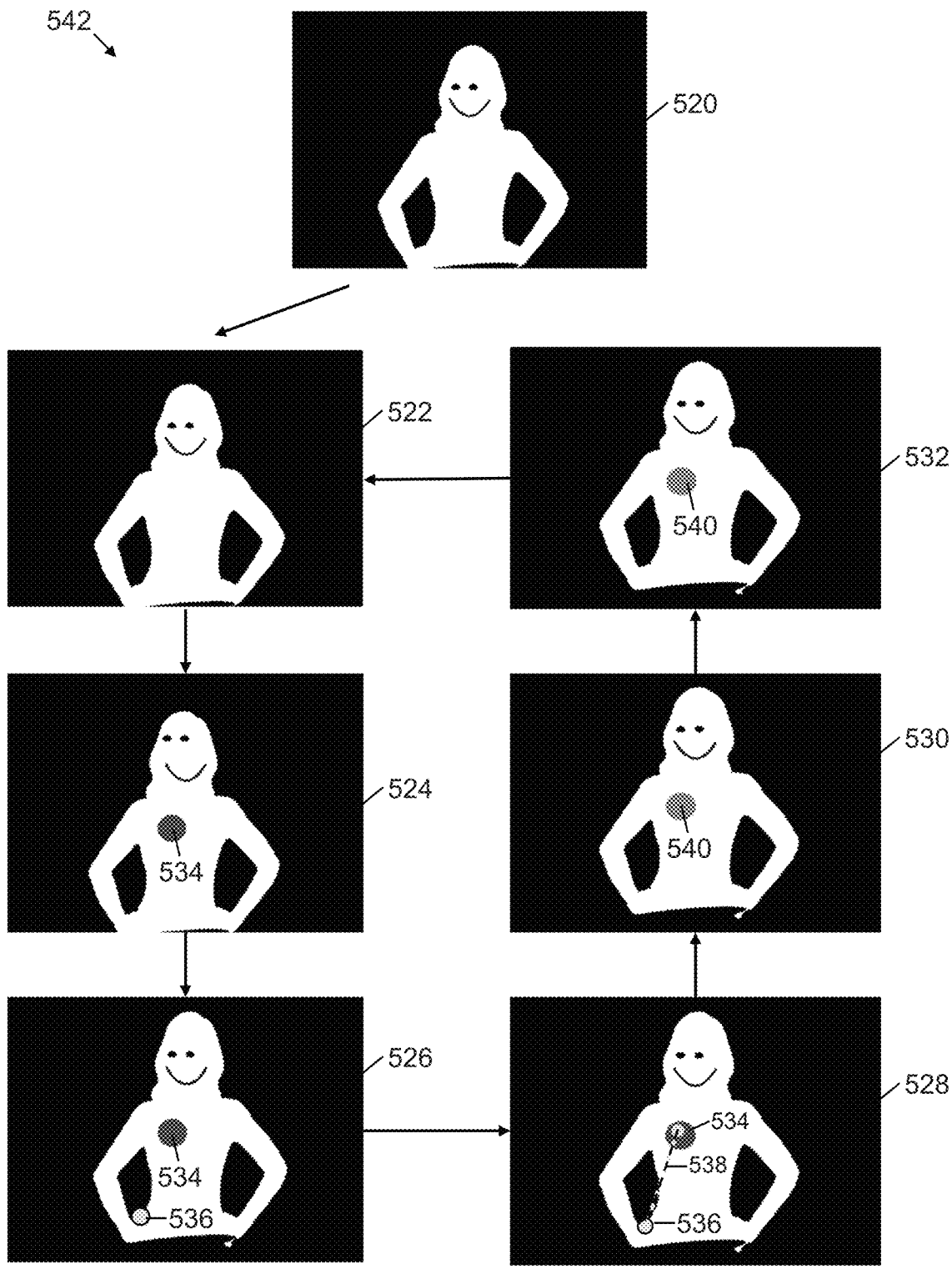
FIG. 28 illustrates a graphical workflow for helping a user to navigate a process of correctly positioning the stethoscope, according to aspects of the present embodiments.

FIG. 28 illustrates a graphical workflow 542 for helping a user to navigate a process of correctly positioning the stethoscope, according to aspects of the present embodiments. At box/step 520, the workflow 542 includes a web camera the captures frames of the user in real time. In some embodiments, the individual image frames will be used as input to the heart location identifier and light tracking algorithms, as further discussed herein. This image may be processed (via a Gaussian blur, down sampling, and/or torso masking). A poseNet model may be used to output key points, for example, the right and left shoulders, hips, and eyes. The light tracking algorithm uses multiple frames captured over time to determine the number of frames in a light blink cycle, and the location of the light. The augmented user images (for example, the real time camera imaged superimposed with drawings), as well as audio recordings, may be stored for future access or further analysis. While the workflow 542 is occurring, the video feed is constantly being fed as input to the screening algorithm (steps 522-532). Accordingly, the current heart location and the light tracking both update in real time as the user moves.

Referring still to FIG. 28, at step 522, the workflow 542 may include outputting 17 key points, via PoseNet. The right and left shoulder in connection with the hip points may be used to calculate the heart recording location. Other points may be used as well. At step 524, the workflow 542 may include drawing a circle 534 over the heart location on the user image frame. At step 526, the workflow 542 may include tracking (via the interface) the blinking light 536 on the stethoscope. The user is prompted to align the blinking light 536 from the stethoscope to the circle 534. The guidance may include a message prompt, arrow pointing the direction to move, and/or color change when the user is in the wrong location vs correct location. At step 528, the workflow 542 may include moving the stethoscope and blinking light 436 (i.e., manually, by the user) to the heart location 534 along path 538. The interface tracks the movement of blinking light 536 on the stethoscope along path 538. At step 530, the workflow 542 may include first establishing that the stethoscope is in the correct position, and then holding the stethoscope stationary, by the user, for a period of time (for example, 10 seconds, or 8 to 12 seconds, or 5 to 15 seconds, and/or other periods of time) while heard sound is recorded by the stethoscope. Stated otherwise, when the user has positioned the stethoscope in the correct location (i.e., the tracked light point 536 is within a margin of error to the heart location point 534) a recording phase will begin. At step 532, the workflow 542 may include repeating steps 522-532 for the next (i.e., second heart location) of the A-P-T-M framework.

Still referring to FIG. 28, in some embodiments, the margin of error may be between about 1 and about 2.5 inches of the true heart location. The margin of error is represented visually to the user by the size of the drawn circles, which is dependent on the users distance from the camera (larger circle when user is close to camera, smaller circle when user is further from camera). Various quality checks may be conducted before or during this stage to ensure the correct screening procedure is followed. These checks may include an electric conductivity test and/or audio sound classification to verify the stethoscope is on bare skin (i.e., not on cloth), use of a gyroscope to verify the correct orientation, Euclidean distance measurement between the blinking light 536 and heart point 534, and/or messages or visuals describing proper screening procedure. According to the present embodiments, a first light tracking algorithm may include 1) determining the number of frames between light blinks (frequency), 2) testing multiple candidate frequencies, 3) identifying the best frequency based on a frequency that gives the largest pixel intensity change over a number of frames, 3) determining the best frequency, and 4) calculating a score to represent the likelihood that a given pixel is the light. This score may be calculated by subtracting pixel intensity of a current frame from a previous blink cycle frame. The score incorporates many factors including: a sliding window (this may be one score every 5-10 frames for 100-120 frame batch, for example) such that the score is the average of these individual subtractions in the batch, and evaluation of the score at other frequencies. If the intensity change is present in other frequency values as well, this pixel is less likely to be the blinking light and the score is lowered. The score many also incorporate the second order derivative (rate of change). Higher derivative values are more likely to be the light blinking and the score is increased.

Referring still to FIG. 28, a second light tracking algorithm may include 1) using an optical flow to track direction and magnitude of movement between frames, 2) using a neural net to learn light point in the image, 3) creating an ensemble to combine various algorithm approaches together, 4) using different colored lights to enhance contrast against more shirt colors and/or to improve the light tracking algorithm, 5) using multiple lights arranged in a circular, or polygonal (3-4-5-6) shape to improve the light tracking algorithm, and/or 6) modifying the LED light (blink speed, light intensity, size). According to the present embodiments, an audio algorithm may include 1) a machine-learning based model used to classify audio recording as being on-skin or on-cloth, 2) using the ML as a clustering algorithm, a variation of a decision tree, a linear model, and/or as a neural network, 3) a machine-learning based model used to classify heart audio recording various classes such as but not limited to: normal, abnormal, aortic stenosis, mitral regurgitation, aortic regurgitation, mitral stenosis, benign murmur, etc. Inputs to these machine-learning algorithms may include entire audio or small segments of audio. Inputs may also be/or include processed audio sound inputs (i.e., raw sound processed via Fourier transform, frequency filtering, noise reduction, and/or compression).

Figure 29A:
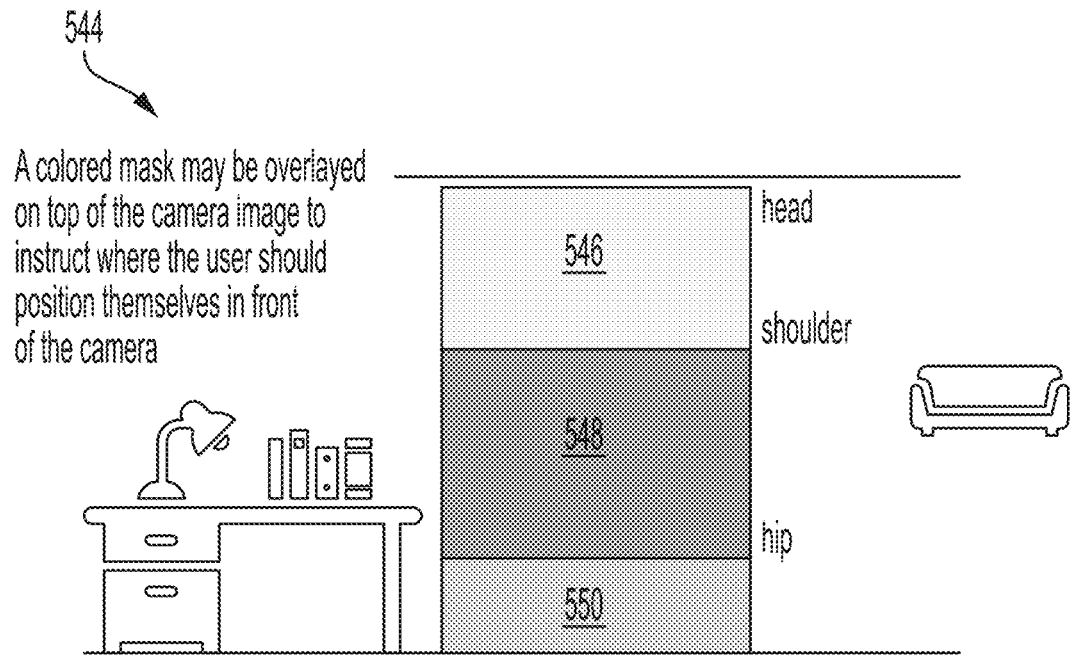
FIG. 29A illustrates a graphical workflow for helping a user to navigate a process of correctly positioning themselves relative to a camera, according to aspects of the present embodiments.

FIGS. 29A-29E illustrate a graphical workflow 544 for helping a user to navigate a process of correctly positioning themselves relative to a camera, according to aspects of the present embodiments. These figures show the camera images that the user will see displayed on the website. Background objects (table, couch) are placed to signify use's home environment. The colored mask are generated by the system and overlaid on the real-time video. In one embodiment, as shown in FIG. 29A, the workflow 544 may include a first region 546 corresponding to a first zone in which the user's head is expected to be located, second zone 548 corresponding to a second zone in which the user's torso is expected to be located, and a third zone 550 corresponding to a first zone in which the user's lower body is expected to be located. The first, second, and third zones 546, 548, 550 are oriented vertically with the first zone 546 on top, the second zone 548 in the middle, and the third zone 550 on the bottom. Each of the first, second, and third zones 546, 548, 550 are graphically drawn or superimposed over the live video feed such that the user can see themselves on the screen relative to the three zones 546, 548, 550 in order to position themselves correctly (that is, positioned at the correct distance from the camera). The first, second, and third zones 546, 548, 550 may include one or more colored masks overlaid on top of the camera image to instruct the user where to position themselves in front of the camera.

Figure 29B:
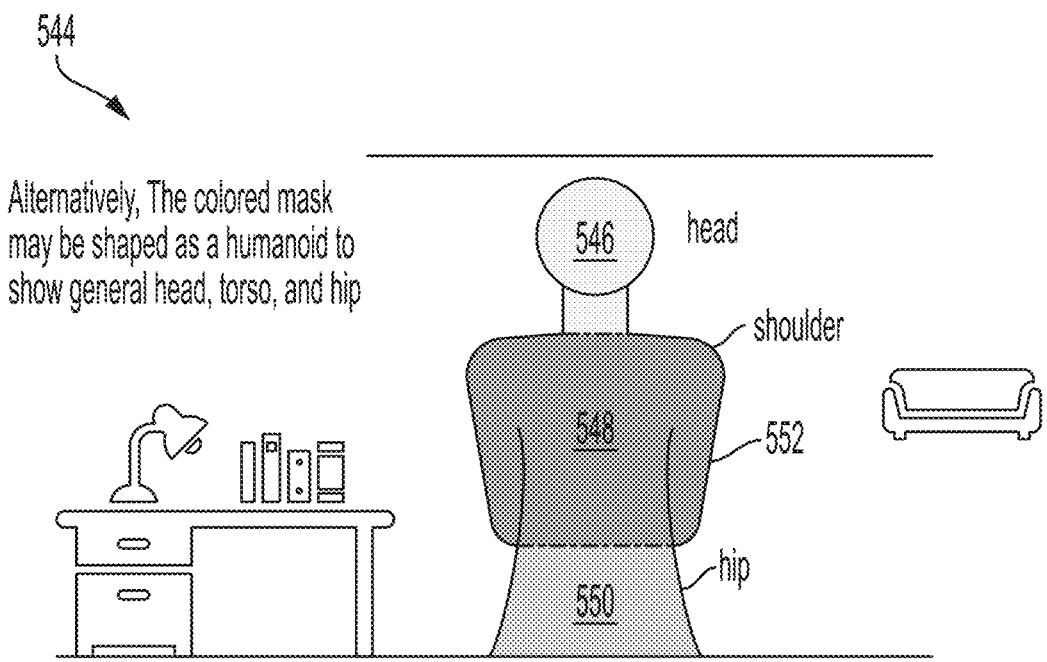
FIG. 29B illustrates a graphical workflow for helping a user to navigate a process of correctly positioning themselves relative to a camera, according to aspects of the present embodiments.

FIG. 29B illustrates a graphical workflow 544 for helping a user to navigate a process of correctly positioning themselves relative to a camera, according to aspects of the present embodiments. In the embodiment of FIG. 29B, the workflow 544 graphically displaces an outline 552 of a body (i.e., the colored mask is shaped as a humanoid showing general head, torso, and hip areas) including the boundaries of the three zones 546, 548, 550 such that the user may position themselves relative to the three zones 546, 548, 550 as well as relative to the body outline 552, in order to position themselves correctly (that is, positioned at the correct distance from the camera).

Figure 29C:
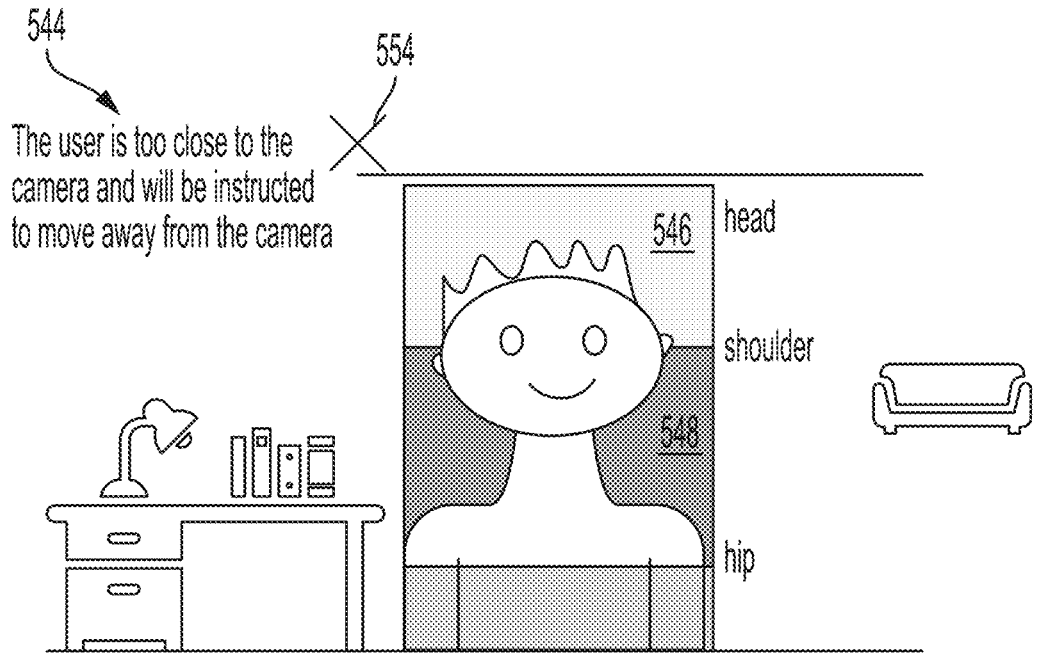
FIG. 29C illustrates a graphical workflow for helping a user to navigate a process of correctly positioning themselves relative to a camera, according to aspects of the present embodiments.

FIG. 29C illustrates a graphical workflow 544 for helping a user to navigate a process of correctly positioning themselves relative to a camera, according to aspects of the present embodiments. In the example shown in FIG. 29C, the user's head is incorrectly positioned such that it is half in the first zone 546 and half in the second zone 548 (i.e., rather than entirely in the first zone 546). Accordingly, the graphical workflow 544 displays an indication 554 (for example, a red "X") indicating that the user is not positioned correctly. In the illustration of FIG. 29C, the user is too close to the camera and is instructed to move away from the camera.

Figure 29D:
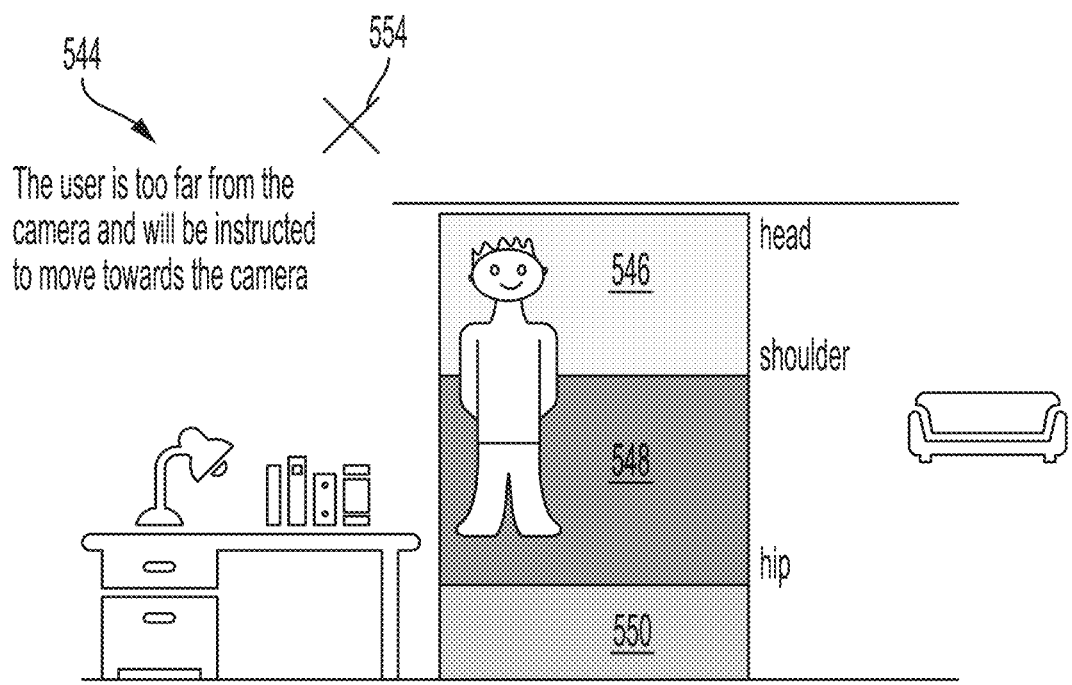
FIG. 29D illustrates a graphical workflow for helping a user to navigate a process of correctly positioning themselves relative to a camera, according to aspects of the present embodiments.

FIG. 29D illustrates a graphical workflow 544 for helping a user to navigate a process of correctly positioning themselves relative to a camera, according to aspects of the present embodiments. In the example shown in FIG. 29D, the user's head and half of the user's torso are incorrectly positioned in the first zone 546, the user's lower body is entirely in the second zone 548, and no part of the user's body is positioned in the third zone 550. Accordingly, the graphical workflow 544 again displays an indication 554 (for example, a red "X") indicating that the user is not positioned correctly. In the illustration of FIG. 29D, the user is too far from the camera and is instructed to move towards the camera.

Figure 29E:
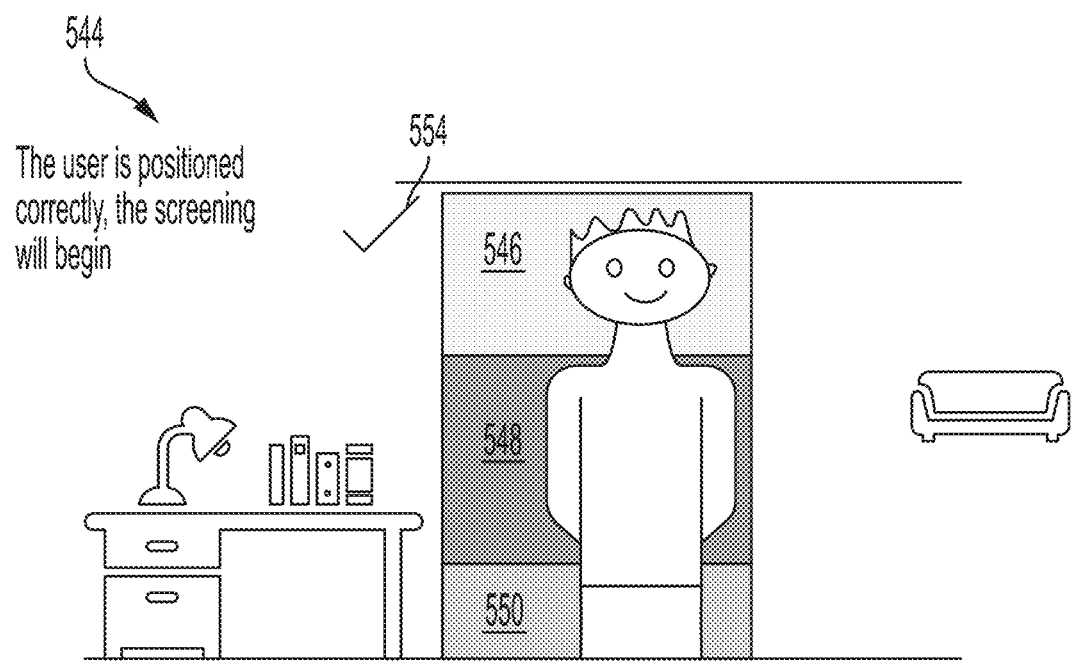
FIG. 29E illustrates a graphical workflow for helping a user to navigate a process of correctly positioning themselves relative to a camera, according to aspects of the present embodiments.

FIG. 29E illustrates a graphical workflow 544 for helping a user to navigate a process of correctly positioning themselves relative to a camera, according to aspects of the present embodiments. In the example shown in FIG. 29E, the user's head is entirely in the first zone 546, the user's torso is entirely in the second zone 548, and the user's lower body is entirely in the third zone 550. Accordingly, the graphical workflow 544 displays an indication 554 (for example, a green checkmark) indicating that the user is positioned correctly, and that the screening will begin.

Computational Framework

Figure 30:
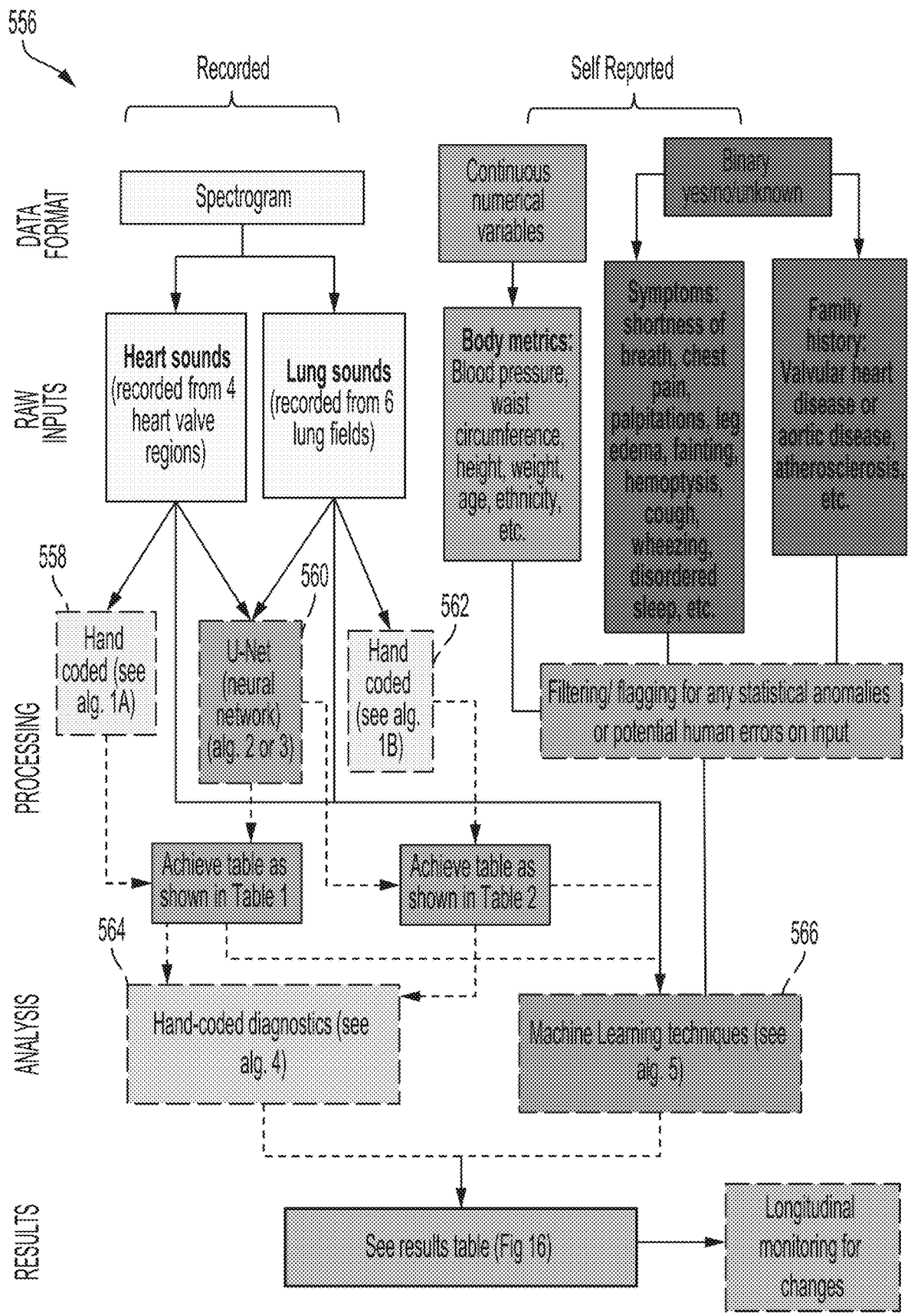
FIG. 30 illustrates a computational framework, according to aspects of the present embodiments.

FIG. 30 illustrates a computational framework, according to aspects of the present embodiments. The computational framework 556 generally combines two different data sources (recorded data and self-reported information) and follows a two-step process for assessing a heart recording. Step one includes converting the recording into a feature vector with entries denoting the presence or absence of various signs of heart disease that can be heard by humans in an audio recording: specifically aortic stenosis, mitral regurgitation, tricuspid regurgitation, mitral valve prolapse, ventricular septal defect, aortic regurgitation, mitral stenosis, and/or patient ductus arteriosus, among others. This is immediately interpretable, as a medical provider can listen to a recording and validate that, for example, a murmur with qualities indicating aortic stenosis is present between S1 and S2. Step two includes combining this feature vector with self-reported symptoms and patient demographics to compute the likelihood of our target diagnoses.

Referring still to FIG. 30, the present embodiments include processing and analyzing heart and lung sounds etc. for diagnosis. Dashed lines indicate a decision point at which we will assess the accuracy of each method and then choose one, the results of which are passed on to the next point. Solid borders on certain boxes indicate an actionable output. Dashed borders indicate an algorithm applied to the input to generate the output. Heart sounds and lung sounds are auscultated from the standard auscultation posts as described in the Bates textbook (*Bates' Guide To Physical Examination and History Taking*, 13th Edition, by Lynn S. Bickley MD FACP, Peter G. Szilagyi MD MPH, Richard M. Hoffman MD MPH FACP, Rainier P. Soriano MD). For heart sounds, the patient holds their breath; if the algorithm detects breath sounds, the patient will be asked to re-record their heart sounds while holding their breath.

Still referring to FIG. 30, the computational framework 556 may use both hand coded algorithms and a U-Net neural network to process heart and lung sounds. For example, at 558, the computational framework 556 may include a first hand-coded algorithm (i.e. algorithm 1) for processing heart sounds, and a second hand-coded algorithm at 562 (i.e., algorithm 1B) for processing lung sounds. The computational framework 556 may also use a U-Net neural network at 560 to process heart sounds using a third algorithm (i.e., algorithm 2) and a fourth algorithm to process lung sounds (i.e. algorithm 3). The results from each of these first 4 algorithms (algorithms 1A, 1B, 2, and 3) may all be used as inputs in both a hand-coded diagnostics algorithm at 564 (i.e., algorithm 4) and a machine learning techniques/algorithm at 566 (i.e., algorithm 5). The various algorithms are further described herein.

Referring still to FIG. 30, the initial sound processing and generation of tables may be carried out as followed. A feature vector may be computed in the "processing" steps of FIG. 30, according to the following: Steps 558 and 562 describes algorithms 1A and 1B, the hand-coded algorithms for segmenting audio features. At step 558, heart sounds segmentation is feasible once the framework 556 has access to 20 to 30 recordings covering the diseases of interest (i.e., to be detected), which would be used for testing and validation. The hand code 558 detects S1, S2, murmurs, and clicks using hand-coded heuristics such as frequency, amplitude, and duration. Note: S1 refers to the "lub" of "lub-dub," i.e., the sound of the closure of the mitral and tricuspid valves. S2 refers to the "dub" of "lub-dub," i.e., the sound of the closure of the aortic and pulmonic valves.

Example 1: Pseudo-Code/Algorithm 1A for Processing Heart Sounds

---
1) Identify S1 and S2 through the sound peaks.
2) Differentiate between S1 and S2 by calculating distance (distance from S1 to S2 should be shorter than the next S2 to S1)
3) Calculate % chance of systolic murmur through the following:
    a.   x = average sound intensity (Hz) of S1 and S2
    b.   y = average sound intensity of baseline (just stethoscope on bare skin from neutral area like palm)
    c.   z = average sound intensity of S1 to S2
        i.   If there is a peak that is an outlier in intensity, remove it from the calculation and count it as a "click"
    d.   % chance of murmur = z/(x−y)
4) Repeat step 3 but for diastolic murmur (step 3c is the average sound intensity of S2 to S1 instead)

---

Referring still to FIG. 30, the present disclosed embodiments may also include additional steps and refinements, for example to also look at the temporal quality of murmurs (whether they are crescendoing, decrescendoing, or both) and whether the S1 and S2 sounds are together or separated. The S1 refers to the closure of the mitral and tricuspid valves, and S2 refers to the closure of the aortic and pulmonic valves; normally these happen together, but if they are split, they may indicate a heart valve issue (for example, such as right bundle branch block, pulmonary stenosis, atrial septal defect, left bundle branch block, and or advanced aortic stenosis, as described commonly in the literature).

Example 2: Lung Sound Segmentation—Algorithm 1B

For lung sounds, the present embodiments look for types of sounds and whether those sounds are heard in abnormal locations. The present embodiments also characterize the rate and rhythm of breathing. These are described in the below table, and are further characterized below. Lung sounds are categorized using if-then statements based on the first three columns of Table 1, and then the location(s) where sounds are heard are recorded. With heart sounds, rather than recording a binary (present/not present) result, the algorithm (1B) records a probability of that lung sound being there. In the event that any abnormal sounds are heard, the patient is asked to then perform a few extra lung recordings while doing a physical motion, such as saying "ee" or speaking out loud, as is standard in clinical practice, and the results of those additional tests are used to also record the probability of egophony, bronchophony, and whispered pectoriloquy being present. Based on the audio spectrogram, the system also records whether adventitious lung sounds such as crackles (defined as fine or coarse), wheezes, rhonchi, stridor, or pleural rub, or mediastinal crunch are present. Abnormalities in rate and rhythm of breathing may also be recorded.

Example 3: Segment Audio Features with a U-Net—Algorithm 2

This option is feasible once there is access to 500 to 2000 recordings, and requires labor intensive-segmentation of each training, testing, and validation recording e.g., (i.e., using, e.g., Praat (https://www.fon.hum.uva.nl/praat/)). In some embodiments, Algorithm 1A may be able to be used to segment the majority of the training data, and then hand segment any data accordingly, (i.e., where it makes mistakes). In some embodiments, collected heart recordings can be manually segmented, resulting in timelines of when the indicative sounds of S1, S2, aortic stenosis, mitral regurgitation, tricuspid regurgitations, Mitral valve prolapse, Ventricular septal defect, Aortic regurgitation, Mitral stenosis, and patent ductus arteriosus occur. The U-Net may then be constructed such that it takes as input a recording (preprocessed into a spectrogram for frequency equivariance) and outputs a corrected segmentation (the segmentation being a (time×11 classes) one hot encoded tensor). The U-Net can then be trained via a categorical cross entropy loss. The resulting segmentations are interpretable and should follow a structure that can be checked. At evaluation time, if the algorithm indicates that, for example, Aortic Stenosis is present between S2 and S1, the algorithm (i.e., Algorithm 2) can raise a warning that it is malfunctioning.

Option 1 and option 2 have the same output: a timeline indicating when each type of feature is present in each recording. This can be converted to a standard feature vector via hand-coded logic, such as "If there is a murmur between S1 and S2 in the recording taken from position A (of APTM) then set the feature to TRUE."

Example 4: Segment Audio Features with a U-Net—Algorithm 3

Algorithm 3 is substantially similar in approach (i.e., segmenting audio features with a U-Net) however, as applied to lung recordings rather than heart recordings.

Example 5: Data Collection Tables

The goal of the previously mentioned algorithms is ultimately to generate a table for heart and lung sounds which can be used for further diagnostic analysis. The tables are shown below:

TABLE 1

Heart sound segmentation output

| | Opening Snap | Crescendo-Decrescendo murmur | Crescendo murmur | Decrescendo murmur | Continuous murmur |
|---|---|---|---|---|---|
| Systolic (S1-S2) | | | | | |
| Diastolic (S2-S1) | | | | | |

Referring to Table 1 above, each cell contains a probability of whether the feature was heard, on a scale from 0.00 to 1.00. In some embodiments, for each recording, the present embodiments include four copies total (one for aortic, pulmonic, tricuspid, and mitral valve regions).

TABLE 2

| | | Lung sound segmentation output | | | | | | | | | |
|---|---|---|---|---|---|---|---|---|---|---|---|
| | Time to | Normal (usually) lung sounds | | | | Adventitious lung sounds | | | | | |
| Length | peak flow | Vesicular | Bronchovesicular | Bronchial | Tracheal | Fine crackles | Coarse crackles | Wheezes | Rhonchi | Stridor | Pleural Rub | Mediastinal Crunch |
| Inhalation | | | | | | | | | | | | |
| Exhalation | | | | | | | | | | | | |

Referring to Table 2 above, the first and second columns ("length" and "time to peak flow"), are given as a time in seconds. Lung sounds are also given as probabilities of whether they are present from 0.00 to 1.00. In some embodiments, a separate table may be used for each lung region auscultated.

Example 6: Hand-Coded Diagnostic Approaches—Algorithm 4

Referring still to FIG. 30, at step 564, the computational framework 556 may include a series of if-then statements are used based on clinical practice guidelines. For example, a systolic murmur in the aortic area frequently means aortic stenosis. If there's a 0.6 probability that such a murmur was heard (according to Table 1 above), then the algorithm starts with that base probability. If a murmur is heard elsewhere at lower probabilities, the algorithm assumes that it's just reflected sound from the aortic valve and drops those from the dataset, or significantly reduces their probabilities, because the odds of two valvular issues at the same time is very unlikely. According to the present embodiments, the probability of the examination finding being true (i.e., probabilities from Tables 1 and 2) may be interpreted in the context of the patient-entered demographic and symptom data to generate a positive predictive value and render a probable diagnosis. For example, if the patient is 70 and being over 65 increases the odds of having aortic stenosis by 0.2, and they also have shortness of breath, which increases the odds of having aortic stenosis by about 0.3, then the algorithm calculates the "one minus" odds (i.e., 1-odds of them having the condition). In the instant example, the odds would then become $1-(1-0.6)(1-0.2)(1-0.3)=1-0.224 \leq 0.776$. According to aspects of the present embodiments, these standards (i.e., weighting factors) may be set based on clinical reasoning, and may be updated as new literature and data becomes available.

Example 7: Modern Machine Learning Approaches—Algorithm 5

Referring still to FIG. 30, at step 566, a large dataset of stethoscope readings taken with the self-guided processes of the present embodiments may be collected, paired with echocardiograms. With approximately 20,000 such pairs, a pair of networks is trained such that an echocardiogram and a stethoscope reading respectively may be converted into a feature vector of around 100 dimensions, with the values of those dimensions learned from data instead of specified by hand. This training may be accomplished by feeding batches of matched pairs to the two networks, and requiring that matching vectors have large dot product and non-matching vectors have small dot product, (for example, in accordance with OpenAI CLIP). The result may be fine-tuned to directly produce values as shown in the End Results Presentation (FIG. 16). This more modern, semi-unsupervised approach serves to improve the robustness of the final results. The present embodiments provide a presentation of data to patients and doctors that is interpretable, accurate, and engaging.

Example 8: Longitudinal Monitoring of Recorded Heart and Lung Sounds

According to aspects of the present embodiments, heart and lung sounds may be monitored longitudinally such that changing symptoms and other potentially concerning conditions may be flagged. In some aspects, the present embodiments incorporate an algorithm that automatically monitors changes in heart and lung sounds over time, and flags anything that sounds concerning. This may be computed through hard code—each time Table 1 or 2 is computed, any probabilities that increased by more than 0.1 (10%) are flagged such that the algorithm asks the user to record sounds again. If the second recording still reflects the 0.1 increase, then the algorithm flags the user to see a doctor. This aspect of the present embodiments aids in detecting potentially dangerous changes to each patient's baseline; not all murmurs are harmful, but keeping track of them over time aids in early identification of those murmurs that may be harmful. For example, aortic stenosis often changes over time; facilitating home exams of aortic stenosis can reduce the need for specialized/expensive tests such as echocardiography for serial monitoring.

Figure 31:
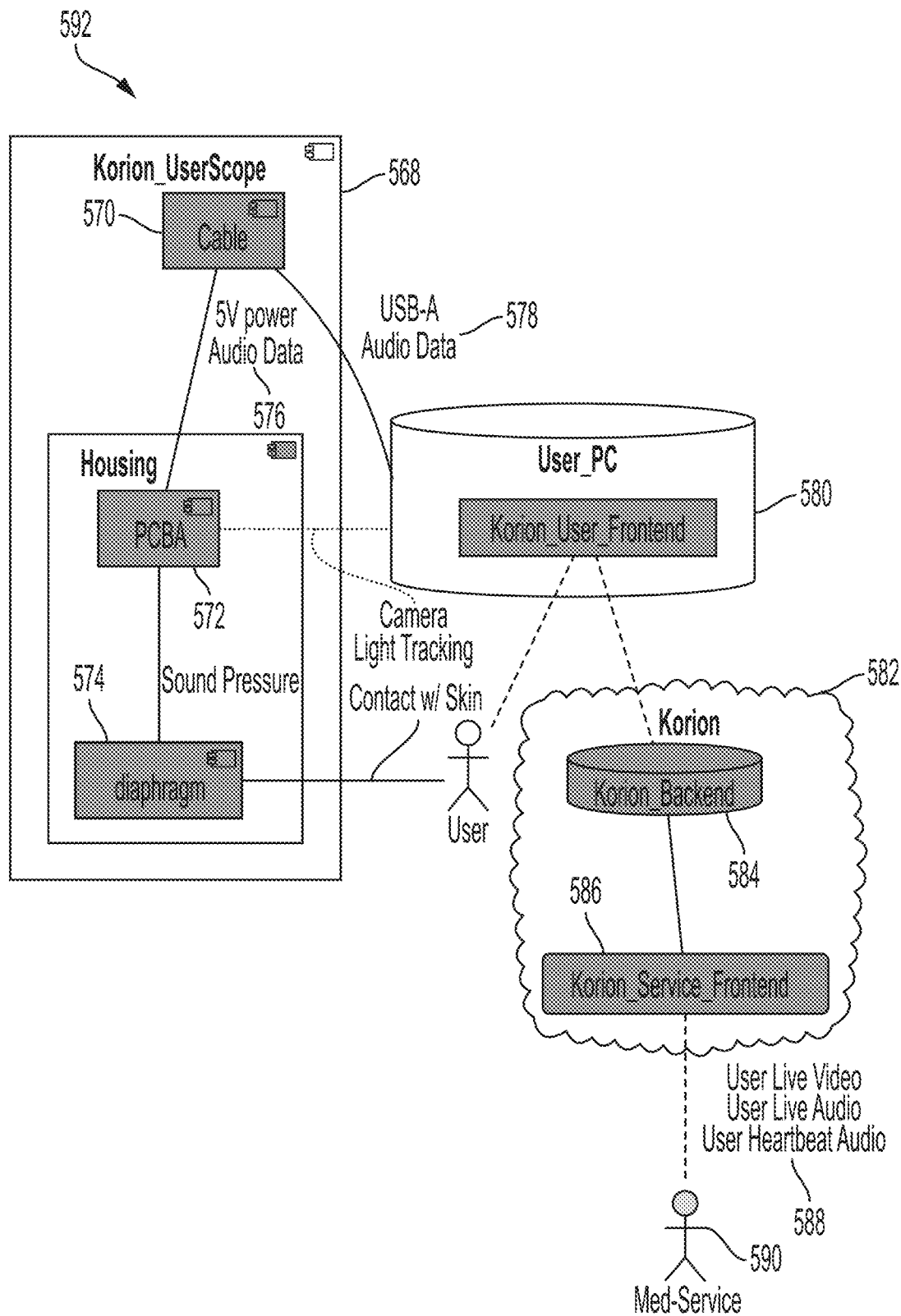
FIG. 31 illustrates a diagnostic ecosystem using the electronic stethoscope, according to aspects of the present embodiments.

FIG. 31 illustrates a diagnostic ecosystem 592 using the electronic stethoscope, according to aspects of the present embodiments. In some embodiments, the diagnostic ecosystem 592 may include 1) the stethoscope 568 including a cable 570 (including the ability to be powered at 5V and to carry audio data 576 (for example, via USB-A audio data 578), housing containing PCBA 572 used for camera light tracking, and diaphragm 574 in contact with the patient's skin, 2) the user PC, laptop, tablet, personal device 580, and 3) the web-based ecosystem/backend 582 including the service frontend 586, Korion backend (for example, including the computational framework 556 of FIG. 30), live user video/audio 588, and connected professional medical services.

The present embodiments describe both software and hardware that are used in connection with each other such that the hardware may be obtained at or around the cost of production (around $30 in 2023 dollars), which disrupts the market for electronic stethoscopes (which currently sell for around $300). Multiple factors influence the low cost of the present stethoscope. The type of microphone being used includes a piezoelectric contact microphone, which is much lower cost than most other electronic stethoscopes, which use a unidirectional microphone. The use of a piezoelectric contact microphone in the present embodiments in enabled via software-based acoustic processing to amplify the sound and convert it into a form ready for human ears. By passing on the amplification and processing to the software, the stethoscope of the present embodiments bypasses costs that would accumulate if it needed to include an integrated physical amplifier.

The electronic stethoscope and ecosystem of the present embodiments include (a) the guided interface which teaches anyone to record their own heart and lung sounds from home, (b) the data that is collected at scale by empowering anyone to collect sounds from home, (c) the machine learning-based diagnostics that empower people to get on-demand feedback, and (d) additional educational tools that people can use to understand why they are getting the results they are, and what to do next.

EQUIVALENTS

Those skilled in the art will recognize, or be able to ascertain using no more than routine experimentation, many equivalents to the specific embodiments of the disclosures described herein. The scope of the present disclosures are not intended to be limited to the above Description, but rather is as set forth in the following claims:

What is claimed is:

1. A method of positioning a stethoscope at one or more heart and/or lung listening locations, the method comprising:
   (a) providing a live video feed of a user's torso;
   (b) determining, by a listening location estimation algorithm, the one or more heart and/or lung listening locations based on the live video feed;
   (c) displaying the live video feed on a video screen with the one or more heart and/or lung listening locations overlaid thereon;
   (d) providing an electronic stethoscope in a field of view of the live video feed, the electronic stethoscope comprising a visual indicator comprising a variably switching light-emitting device;
   (e) moving the electronic stethoscope within a field of view of the live video feed such that the visual indicator is in the vicinity of the one or more heart and/or lung listening locations;
   (f) placing the electronic stethoscope under an article of clothing of the user against the user's bare skin with the variably switching light-emitting device facing away from the user such that light transmitted by the variably switching light-emitting device passes through the article of clothing and is visible on the live video feed; and
   (g) rendering, on the live video feed displayed on the video screen, a shape overlapping with a live location of the visual indicator of the electronic stethoscope, the shape changing in color and/or shape to indicate when the electronic stethoscope is positioned correctly at one of the one or more heart and/or lung listening locations.

2. The method of claim 1, wherein determining, by the listening location estimation algorithm, the one or more heart and/or lung listening locations based on the live video feed comprises using a pose estimation algorithm, the pose estimation algorithm outputting key points of a pose of the user, the key points comprising the locations of at least the left shoulder, the hips, and the right shoulder of the user, and
   wherein determining the one or more heart and/or lung listening locations further comprises:
      determining vertical locations using a fixed percentage of a shoulder-to-hip distance, and
      determining horizontal locations using a fixed percentage of a shoulder-to-shoulder distance.

3. The method of claim 1, the method after step (g) further comprising prompting the user, by the listening location estimation algorithm, to move the stethoscope to align the shape overlapping with the visual indicator with the overlaid one or more heart and/or lung listening locations.

4. The method of claim 3, wherein prompting the user comprises at least one of: displaying a message prompt, displaying an arrow pointing in the direction the user should move the stethoscope, and changing a color of the shape overlapping with the visual indicator when the user is in the wrong location to a different color than when the user is in correct location.

5. The method of claim 1, wherein the method further comprises:
   (h) recording a duration of heart and/or lung sounds at each of the heart valve and/or lung listening locations;
   (i) providing the sound recordings to a trained audio classification algorithm;
   (j) repeating steps (a) through (j) until a sound recording at each of the heart valve and/or lung listening locations has been recorded; and
   (k) outputting, by the trained audio classification algorithm, a classification of each of the sound recordings corresponding to at least one of normal heart function, normal lung function, one or more of a plurality of heart conditions, or one or more of a plurality of lung conditions.

6. The method of claim 5, wherein the plurality of heart conditions comprises innocent murmur, aortic stenosis, and mitral valve prolapse, and
   wherein the plurality of lung conditions are associated with abnormal lung sounds comprising crackles, wheezes, rhonchi, stridor, rales, and pleural friction rubs.

7. The method of claim 1, wherein the one or more variably switching light-emitting devices comprise one or more light-emitting diodes each emitting light of a visible wavelength or a near-infrared wavelength,
   wherein the one or more light-emitting diodes each follow a controlled switching program that switches the one or more light-emitting diodes on and off in an ordered pattern at a controllable repetition frequency of between about 2 Hz and about 30 Hz,
   wherein the light-emitting device emits light at a wavelength between about 400 nm and about 1000 nm, and
   wherein rendering, on the live video feed displayed on the video screen, a shape overlapping with a live location of the visual indicator comprises using a light tracking algorithm that uses multiple frames captured over time to determine the number of frames in a light blink cycle of the visual indicator, thereby identifying the location of the visual indicator based on the controllable repetition frequency.

8. The method of claim 1, wherein the one or more heart and/or lung listening locations comprise one or more of an aortic valve area, a pulmonic valve area, a tricuspid valve area, and a mitral valve area, and
   wherein the lung listening locations comprise locations one or more locations near apexes of lungs, upper lobes of lungs, middle lobes of lungs, and lower lobes of lungs, on left and right sides of the user's front and back torso.

9. The method of claim 1 further comprising, after step (a) and before step (b):

superimposing, in real time, multiple zones comprising multiple color masks on the video screen, the multiple zones comprising a first region, a second region, and a third region, thereby indicating to the user if the user's body as a whole is too close or too far from the video screen, or alternatively, if the user's body as a whole is positioned correctly relative to the video screen.

10. The method of claim 9, wherein the first region corresponds to a first zone in which the user's head is expected to be located,
   wherein the second region corresponds to a second zone in which the user's torso is expected to be located, and
   wherein the third region corresponds to a third zone in which the user's lower body is expected to be located.

11. The method of claim 10 further comprising:
   displaying a first indication on the video screen if the user's body is incorrectly positioned within each of the first, second, and third regions, and
   displaying a second indication on the video screen if the user's body is correctly positioned within each of the first, second, and third regions.

12. An electronic stethoscope comprising:
   a chest piece comprising:
      a hollow bell portion;
      a membrane portion covering an end of the bell portion;
      a stem portion attached to an outer circumferential wall of the hollow bell portion;
      a shoulder portion attached to the stem portion; and
      a microphone compartment attached to the shoulder portion;
   a microphone disposed in the microphone compartment;
   a visual indicator disposed on an exterior of the chest piece; and
   an electronic data connection from the microphone,
   wherein at least a portion of each of the hollow bell portion, the stem portion, the shoulder portion, and the microphone compartment form a single, continuous component composed of a polymer material and formed via a single manufacturing process.

13. The electronic stethoscope of claim 12, wherein the electronic stethoscope further comprises a microprocessor and an analog-to-digital converter,
   wherein the visual indicator comprises one or more light-emitting devices, and
   wherein the microphone comprises a pulse density modulation (PDM) micro-electromechanical systems (MEMS) microphone and/or a lavalier microphone.

14. The electronic stethoscope of claim 12, wherein the membrane comprises a flexible polymer sheet composed of a material elected from the group consisting of acetate, polyester, polyethylene terephthalate (PET), polyethylene, polypropylene, polystyrene, epoxy fiberglass, resin, thermoset plastic, polyvinyl chloride (PVC), and polytetrafluoroethylene (PTFE), and
   wherein the membrane comprises a thickness in a range from about 0.01 inches to about 0.05 inches.

15. The electronic stethoscope of claim 12, wherein the hollow bell portion, the stem portion, the shoulder portion, and the microphone compartment are composed of a plastic material selected from the group consisting of polylactic acid (PLA), acrylonitrile butadiene styrene (ABS), and polyethylene terephthalate glycol-modified (PET-G),
   wherein the hollow bell portion comprises a concave face comprising an inverted conical portion, and
   wherein the chest piece further comprises an internal bore disposed within the concave face of the hollow bell portion and extending to the microphone compartment.

16. The electronic stethoscope of claim 12, comprising a microphone seal disposed circumferentially around, and in contact with, an interior wall of a lumen of the microphone compartment, the microphone seal further in contact with an exterior surface of the microphone such that air does not pass between the interior wall of the lumen of the microphone compartment and the exterior surface of the microphone.

17. The electronic stethoscope of claim 16, wherein the microphone seal is composed of at least one of silicone, rubber, adhesive, resin, epoxy, polymer, wax, acrylic, rubber cement, thermoplastic adhesive, hot-melt adhesive, polytetrafluoroethylene, polyurethane, polycarbonate, polypropylene, nylon, nitrile, neoprene, polyvinyl chloride, fluorocarbon, and fluorosilicone.

18. A method of training a machine learning algorithm to identify heart and/or lung sounds comprising:
   obtaining heart and/or sound recordings corresponding to known heart and/or lung conditions and corresponding to normal healthy heart and/or lung function;
   obtaining non-heart-and/or-lung sound recordings of sounds;
   providing the heart and/or lung sound recordings and non-heart-and/or-lung sound recordings to an audio classifier model;
   segmenting the recordings via at least one of frequency, amplitude, and duration;
   inputting the segmented recordings into a U-Net neural network;
   preprocessing the segmented recordings, via the U-Net neural network, into a spectrogram for frequency equivariance, thereby producing corrected segmentation recordings;
   outputting the corrected segmentation recordings; and
   using the audio classifier model to train the machine learning algorithm to distinguish between the heart and/or lung sound recordings and non-heart-and/or-lung sound recordings,
   wherein the heart and/or lung sound recordings are obtained from recordings performed by an electronic stethoscope and/or a microphone, and
   wherein the audio classifier model comprises a pre-trained audio neural network (PANN), a dataset of known audio recordings, information regarding health conditions and demographics of patients with known heart and/or lung conditions, and information regarding healthy patients.

19. The method of claim 18, wherein non-heart-and/or-lung sound recordings comprises sounds such as speech, vehicle traffic, dogs barking, children crying, noise, and music, and
   wherein providing sound recordings to the audio classifier model occurs on a regular repeating schedule and comprises providing new sound recordings and new known health information.

20. The method of claim 18, wherein segmenting the recordings via at least one of frequency, amplitude, and duration comprises identifying at least two portions of each recording, the method further comprising identifying any other indicative sound within each recording,
   wherein the corrected segmentation recordings comprise a timeline indicating when each type of feature is present in each recording.

21. The method of claim 20, wherein the at least two portions of each recording comprise:

for heart recordings, a first portion corresponding to a systolic portion of a heartbeat, and a second portion corresponding to diastolic portion of a heartbeat, and for lung recordings, a first portion corresponding to an inhalation, and a second portion corresponding to an exhalation.

\* \* \* \* \*